(12) United States Patent
Quan et al.

(10) Patent No.: US 12,140,520 B2
(45) Date of Patent: Nov. 12, 2024

(54) NANOSENSORS AND USE THEREOF

(71) Applicant: NanoMosaic Inc., Waltham, MA (US)

(72) Inventors: Qimin Quan, Newton, MA (US); Joseph Wilkinson, Windham, NH (US); Joshua A. Ritchey, Melrose, MA (US); John Boyce, Boston, MA (US)

(73) Assignee: NanoMosaic Inc., Waltham, MA (US)

( * ) Notice: Subject to any disclaimer, the term of this patent is extended or adjusted under 35 U.S.C. 154(b) by 510 days.

(21) Appl. No.: 17/434,287

(22) PCT Filed: Feb. 27, 2020

(86) PCT No.: PCT/US2020/020204
§ 371 (c)(1),
(2) Date: Aug. 26, 2021

(87) PCT Pub. No.: WO2020/176793
PCT Pub. Date: Sep. 3, 2020

(65) Prior Publication Data
US 2022/0128446 A1    Apr. 28, 2022

Related U.S. Application Data

(60) Provisional application No. 62/811,543, filed on Feb. 28, 2019, provisional application No. 62/811,559, (Continued)

(51) Int. Cl.
*G01N 15/06* (2024.01)
*B82Y 15/00* (2011.01)
(Continued)

(52) U.S. Cl.
CPC ......... *G01N 15/0612* (2013.01); *G01N 21/25* (2013.01); *G01N 21/554* (2013.01);
(Continued)

(58) Field of Classification Search
None
See application file for complete search history.

(56) References Cited

U.S. PATENT DOCUMENTS 3,779,628 A    12/1973   Kapron et al.
6,645,757 B1   11/2003   Okandan et al.
(Continued)

FOREIGN PATENT DOCUMENTS

CN    104487824 A    4/2015
CN    205679617      11/2016
(Continued)

OTHER PUBLICATIONS

Lei, Highly ordered nanostructures with tunable size shape and properties, Progress in materials science, 52, 2007 (Year: 2007).*
(Continued)

*Primary Examiner* — Uzma Alam
*Assistant Examiner* — Justin J Van Cleave
(74) *Attorney, Agent, or Firm* — Goodwin Procter LLP

(57) ABSTRACT

Provided is a nanosensor having a high dynamic range and sensitivity for detecting the presence, and/or quantifying the amount, of an analyte in a sample of interest. Also provided is a cartridge incorporating the nanosensor, and a method and system for detecting the presence, and/or quantifying the amount, of the analyte in the sample of interest.

30 Claims, 38 Drawing Sheets

Related U.S. Application Data filed on Feb. 28, 2019, provisional application No. 62/811,579, filed on Feb. 28, 2019, provisional application No. 62/811,041, filed on Feb. 27, 2019.

(51) Int. Cl.
  *G01N 15/01* (2024.01)
  *G01N 21/25* (2006.01)
  *G01N 21/552* (2014.01)
  *G01N 33/68* (2006.01)

(52) U.S. Cl.
  CPC .............. *B82Y 15/00* (2013.01); *G01N 15/01* (2024.01); *G01N 33/6863* (2013.01); *G01N 2333/4737* (2013.01); *G01N 2333/525* (2013.01); *G01N 2333/5412* (2013.01)

(56) References Cited

U.S. PATENT DOCUMENTS

| | | | |
|---|---|---|---|
| 9,624,532 | B2 | 4/2017 | Gordon |
| 9,675,288 | B2* | 6/2017 | Yamakawa .......... G01N 21/658 |
| 2002/0028457 | A1 | 3/2002 | Empedocles et al. |
| 2002/0028519 | A1 | 3/2002 | Yguerabide et al. |
| 2003/0112443 | A1 | 6/2003 | Hjelme et al. |
| 2003/0190652 | A1 | 10/2003 | De La Vega et al. |
| 2004/0012062 | A1 | 1/2004 | Miyajima et al. |
| 2004/0059229 | A1 | 3/2004 | Lurie |
| 2004/0134884 | A1 | 7/2004 | Wei et al. |
| 2004/0183176 | A1 | 9/2004 | Naya et al. |
| 2005/0117157 | A1 | 6/2005 | Tarsa |
| 2005/0161594 | A1 | 7/2005 | Hollingsworth et al. |
| 2007/0090836 | A1 | 4/2007 | Xiang et al. |
| 2009/0117168 | A1 | 5/2009 | Keenan |
| 2010/0124824 | A1 | 5/2010 | Eilmsteiner et al. |
| 2011/0053794 | A1 | 3/2011 | Zhang |
| 2011/0109364 | A1 | 5/2011 | Yamasaki et al. |
| 2011/0207237 | A1 | 8/2011 | Sai et al. |
| 2011/0208031 | A1 | 8/2011 | Wolfe et al. |
| 2011/0212848 | A1* | 9/2011 | Duffy ............... G01N 33/54313 506/15 |
| 2011/0237445 | A1 | 9/2011 | Andersson Svahn et al. |
| 2011/0277249 | A1 | 11/2011 | Abuzaina et al. |
| 2012/0045748 | A1 | 2/2012 | Willson et al. |
| 2013/0137129 | A1 | 5/2013 | Yu et al. |
| 2013/0286467 | A1 | 10/2013 | Vlasko-Vlasov et al. |
| 2013/0338627 | A1 | 12/2013 | Rylander et al. |
| 2014/0024131 | A1 | 1/2014 | Kim et al. |
| 2014/0154668 | A1 | 6/2014 | Chou et al. |
| 2014/0218727 | A1 | 8/2014 | Li et al. |
| 2014/0322729 | A1 | 10/2014 | Fan et al. |
| 2014/0334005 | A1 | 11/2014 | Omenetto et al. |
| 2014/0357529 | A1* | 12/2014 | Choi .................... B01J 19/0046 506/32 |
| 2014/0358128 | A1 | 12/2014 | Montazeri et al. |
| 2015/0092191 | A1 | 4/2015 | Jung et al. |
| 2015/0226738 | A1 | 8/2015 | Dai et al. |
| 2016/0003744 | A1 | 1/2016 | Chou et al. |
| 2016/0312275 | A1 | 10/2016 | Blainey et al. |
| 2016/0355869 | A1 | 12/2016 | Blair et al. |
| 2017/0168048 | A1 | 6/2017 | Szmacinski et al. |
| 2017/0265788 | A1 | 9/2017 | Quan et al. |
| 2017/0284935 | A1 | 10/2017 | Ndukaife et al. |
| 2017/0370836 | A1* | 12/2017 | Gerion ................... G01N 21/82 |
| 2021/0001330 | A1 | 1/2021 | Quan et al. |

FOREIGN PATENT DOCUMENTS

| | | |
|---|---|---|
| CN | 106233140 A | 12/2016 |
| CN | 106841188 A | 6/2017 |
| JP | 2010526316 A | 7/2010 |
| JP | 2011152108 A | 8/2011 |
| JP | 2013521500 A | 6/2013 |
| JP | 2014-531043 A | 11/2014 |
| JP | 2015-514225 A | 5/2015 |
| JP | 2015523100 A | 8/2015 |
| JP | 2016-29400 A | 3/2016 |
| JP | 2017-503483 A | 2/2017 |
| WO | WO-2008116093 | 9/2008 |
| WO | WO-2008136734 A1 | 11/2008 |
| WO | WO-2009117168 A2 | 9/2009 |
| WO | WO-2011109364 A2 | 9/2011 |
| WO | WO-2011109379 A1 | 9/2011 |
| WO | WO-201362540 A1 | 5/2013 |
| WO | WO-2013154770 A1 | 10/2013 |
| WO | WO-2014021809 A1 | 2/2014 |
| WO | WO-2014022581 A1 | 2/2014 |
| WO | WO-2015100373 A2 | 7/2015 |
| WO | WO-2015130980 A1 | 9/2015 |
| WO | WO-2015175398 A1 | 11/2015 |
| WO | WO-2016105548 A1 | 6/2016 |
| WO | WO-2016168386 A1 | 10/2016 |
| WO | WO-2017124101 A2 | 7/2017 |
| WO | WO-2019186416 A1 | 10/2019 |
| WO | WO-2020176793 A1 | 9/2020 |

OTHER PUBLICATIONS

Dhara et al., "Highly Sensitive and Wide-range Nonenzymatic Disposable Glucose Sensor Based on a Screen Printed Carbon Electrode Modified with Reduced Graphene Oxide and Pd—CuO Nanoparticles," Microchim Acta 182:2183-2192 (2015).
International Search Report and Written Opinion for Application No. PCT/US2020/020204, dated Apr. 23, 2020 (11 pages).
Liu et al., "Highly Selective and Ultrasensitive Detection of Nitrite Based Fluorescent Gold Nanoclusters," Talanta 104:135-139 (2013).
International Search Report and Written Opinion for Application No. PCT/US2018/13313, mailed Jun. 1, 2018.
International Search Report and Written Opinion for Application No. PCT/US2018/49883, mailed Jan. 29, 2019.
International Search Report and Written Opinion for Application No. PCT/US2015/030125, mailed Aug. 7, 2015.
Goncalves et al., "Self-Assembled Hydrogel Nanoparticles for Drug Delivery Applications," Materials 3:1420-1460 (2010).
European Extended Search Report for EP 18854207.0, mailed Jun. 18, 2021.
Soo et al., "A Simple Gold Nanoparticle Probes Assay for Identification of *Mycobacterium tuberculosis* and *Mycobacterium tuberculosis* Complex from Clinical Specimens, "Molecular and Cellular Probes 23:240-246 (2009).
European Extended Search Report for EP 20763144.1, mailed Oct. 10, 2022.
Gautam et al., "Absorption Kinetics of Ammonia Sensing by Graphene Films Decorated with Platinum Nanoparticles," Journal of Applied Physics 111:094317 (2012).
Hsieh et al., "Localized Surface Plasom Coupled Fluorescence Fiber-Optic Biosensor with Gold Nanoparticles," Anal. Chem. 79(9):3487-3493 (2007).
Kundu et al., "Development of Evanescent Wave Absorbance-based Fibre-optic Biosensor," Pramana- J. Phys. 75:1099 (2010).
Lepinay et al., "Improved Detection Limits of Protein Optical Fiber Biosensors Coated with Gold Nanoparticles," Elsevier: Biosensors and Bioelectronics 52:337-344 (2014).
Lin et al., "Tapered Optical Fiber Sensor Based on Localized Surface Plasmon Resonance," Opt. Express 20(19):21693-21701 (2012).
Saunerits et al., "Sensing Using Localized Surface Plasom Resonance Sensors," Chem. Commun. (Camb). Sep. 18:48(72):8999-9010 (2012).
Wei et al., "Sensitive Plasmonic Biosensor Using Gold Nanoparticles on a Nano Fiber Tip," Proc. SPIE 6099. Plasomics in Biology and Medicine III (2006).
Bian et al., "Tracking the Antibody Immunome in Type 1 Diabetes Using Protein Arrays," J. Proteome Res. 16:195-203 (2017).
Brofelth et al., "Multiplex Profiling of Serum Proteins in Solution using Barcoded Antibody Fragments and Next Generation Sequencing," Communications Biology 339(3):1-6 (2020).
Hosokawa et al., Nanoparticle Technology Handbook Elsevier Science 644:365 (2017).

(56) References Cited

OTHER PUBLICATIONS

Lo et al., "Comprehensive Profiling of the Rheumatoid Arthritis Antibody Repertoire," Arthritis Rheumatol. 72(2):242-250 (2020).
Petersoon et al., "Multiplexing of Miniturized Planar Antibody Arrays for Serum Protein Profiling—Biomarker Discovery in SLE Nephritis," Lab Chip 14(11):1931-1942 (2014).
Singh et al., "Salinomycin Inhibits Epigenetic Modulator EZH2 to Enhance Death Receptors in Colon Cancer Stem Cells," Spigenetics 16(2):144-161 (2021).
Zandian et al., "Whole-Proteome Peptide Microcarrays for Profiling Autoantibody Repertoires within Multiple Sclerosis and Narcolepsy," J. of Proteome Res. 16:1300-1314 (2017).
Zuo et al., "Whole-exome SNP Array Identifies 15 New Susceptiblity Loci for Psoriasis," Nature Communications 6:6793 (2015).

\* cited by examiner

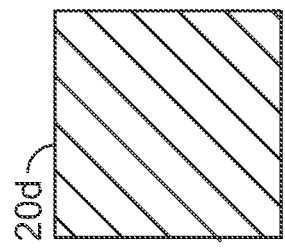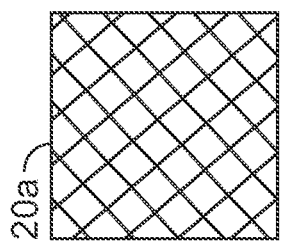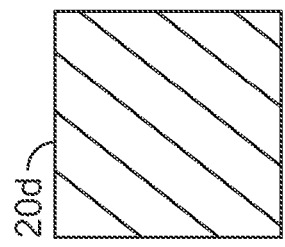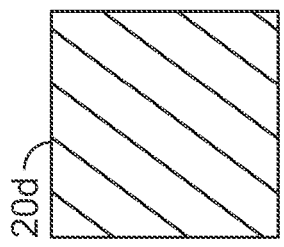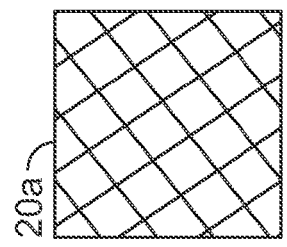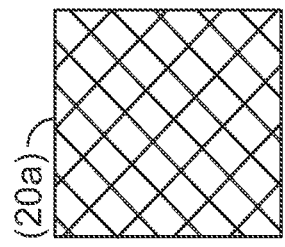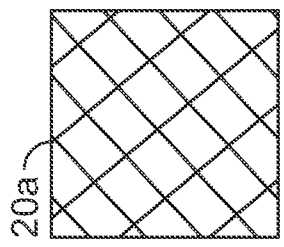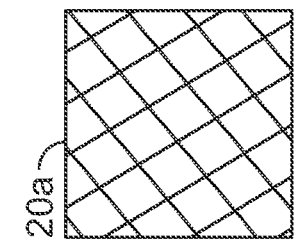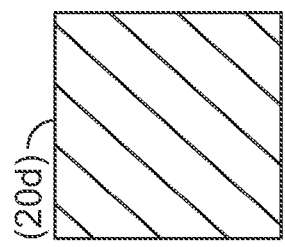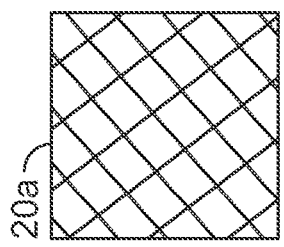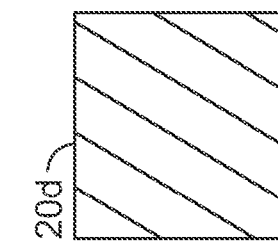
FIG. 2A

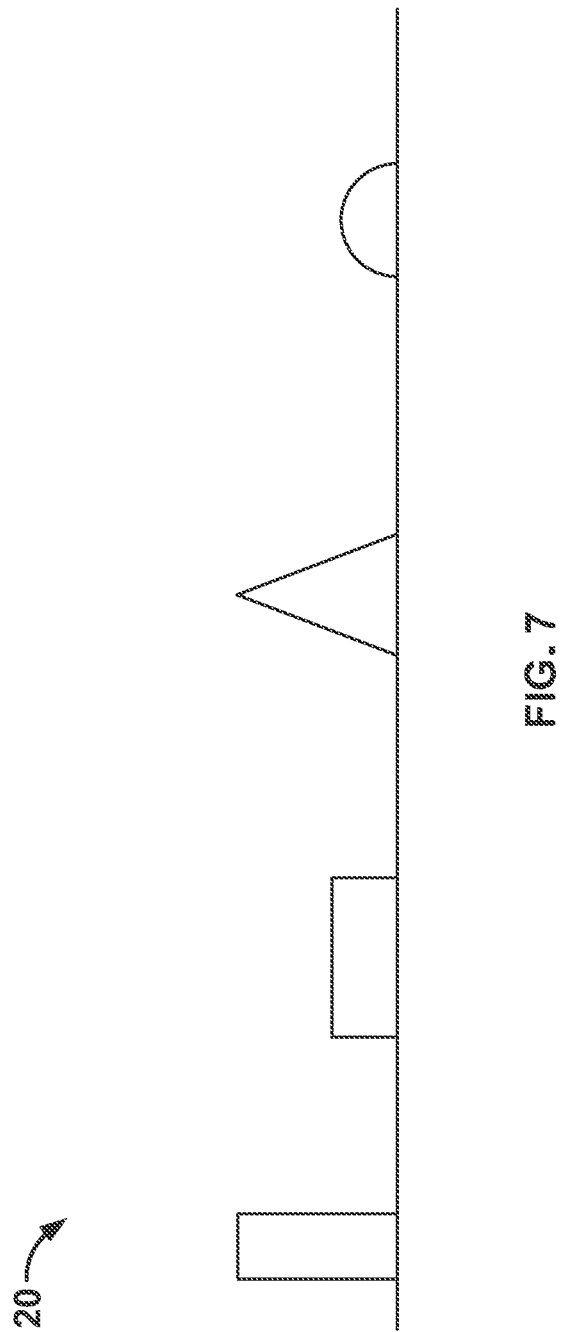

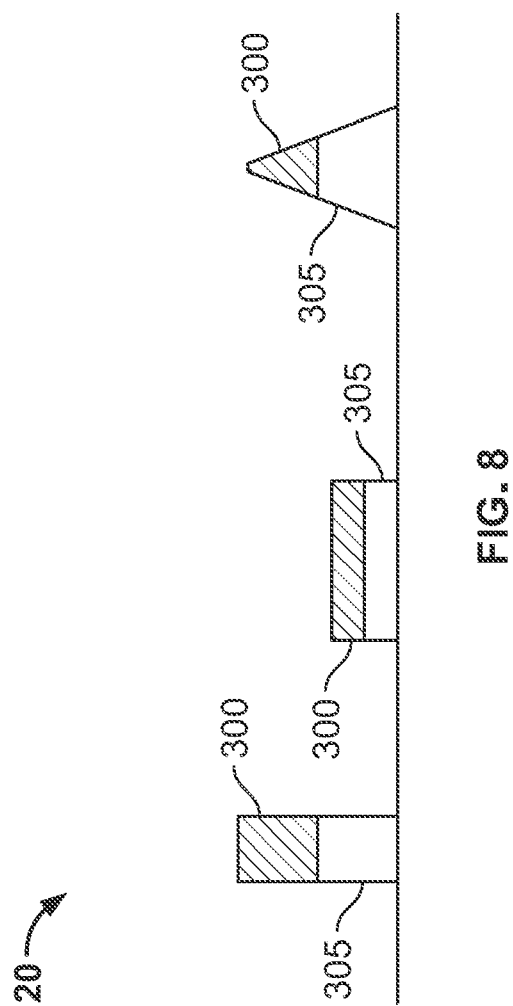

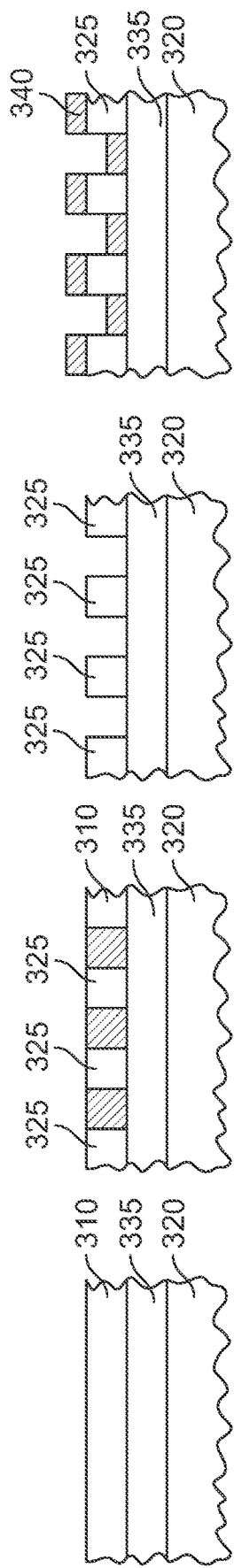
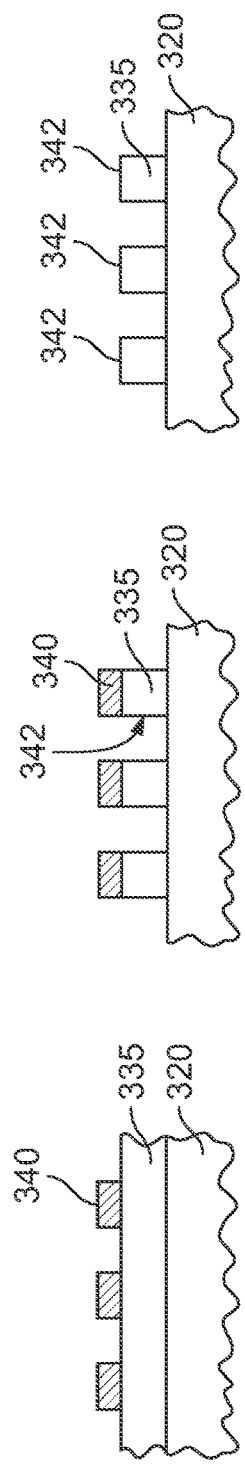
FIG. 10A FIG. 10B FIG. 10C FIG. 10D FIG. 10E FIG. 10F FIG. 10G

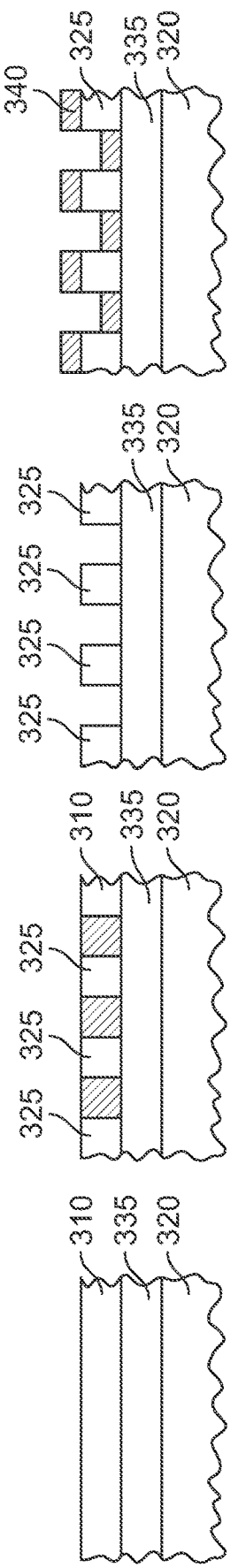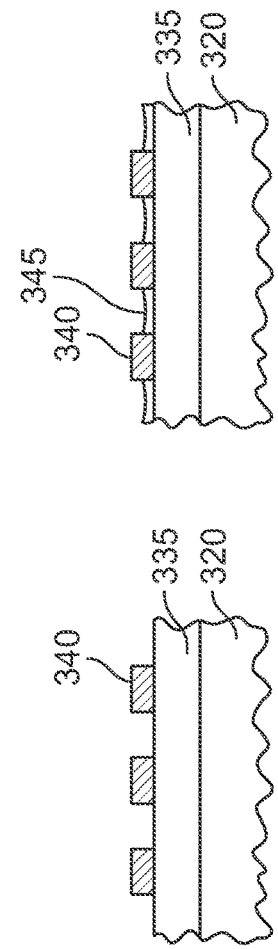

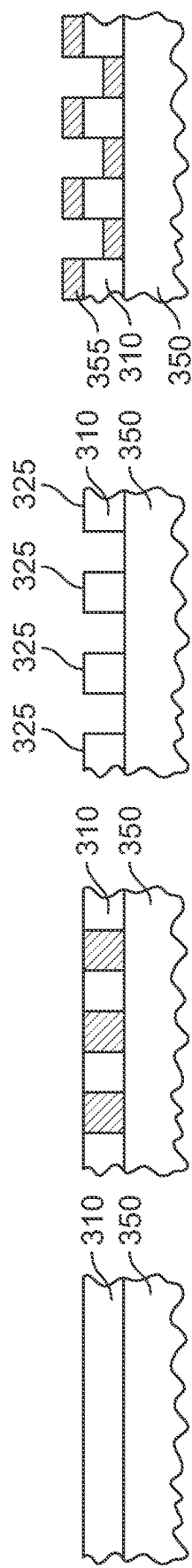
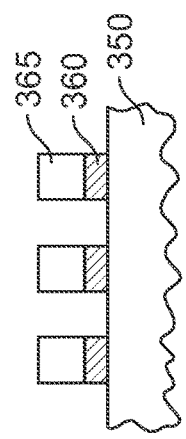
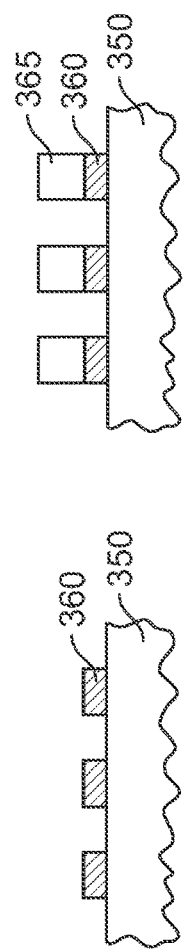
FIG. 12A
FIG. 12B
FIG. 12C
FIG. 12D
FIG. 12E
FIG. 12F

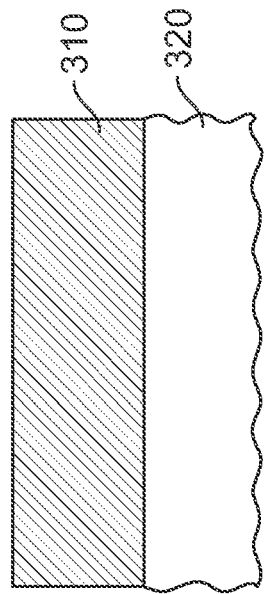
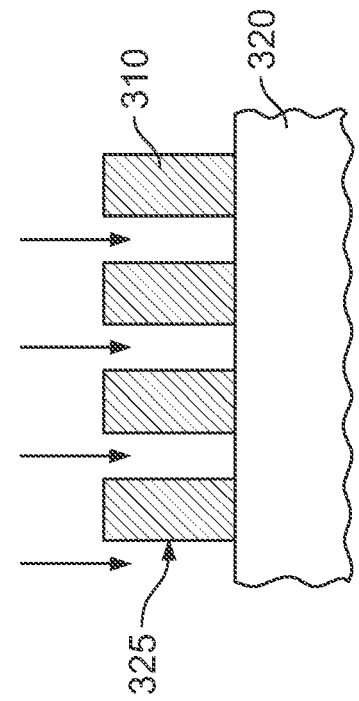
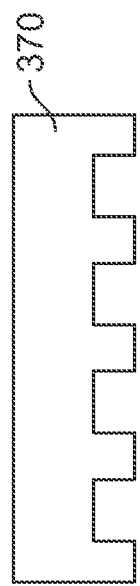
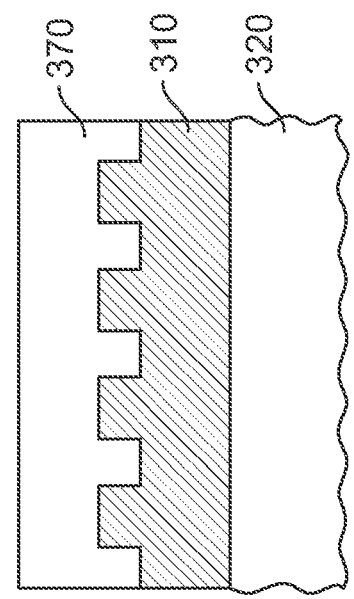
FIG. 13A
FIG. 13B
FIG. 13C
FIG. 13D

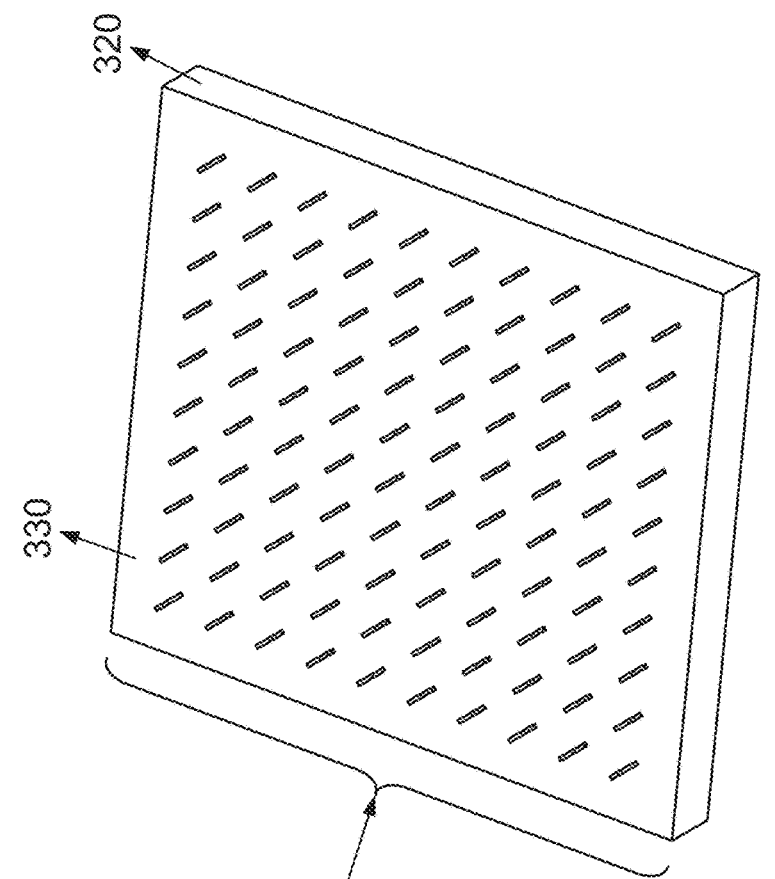
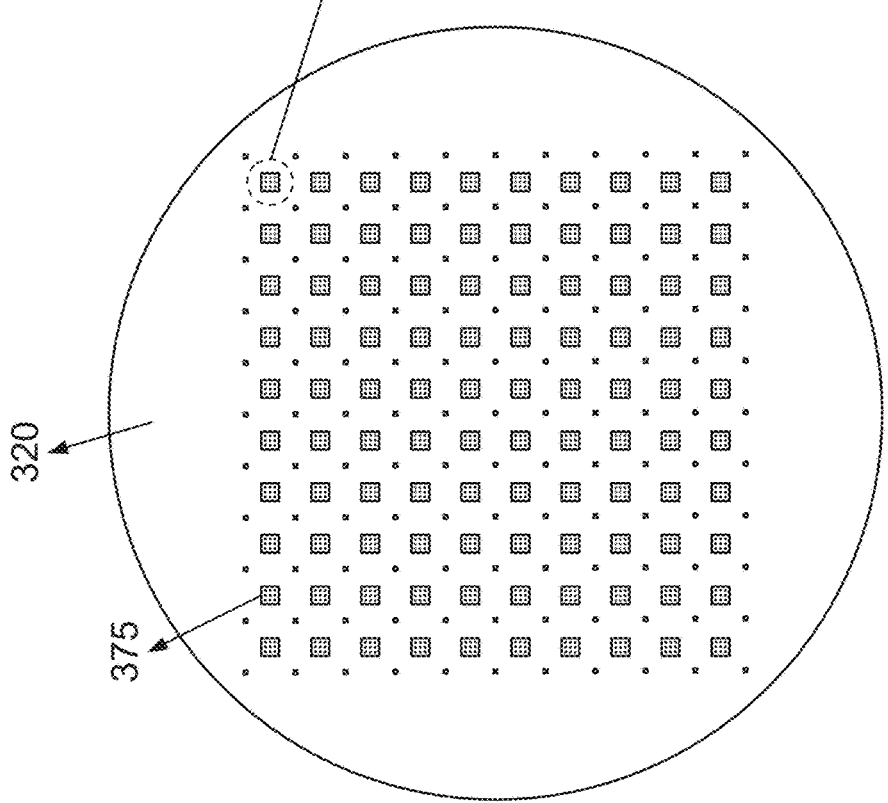
FIG. 14B
FIG. 14A

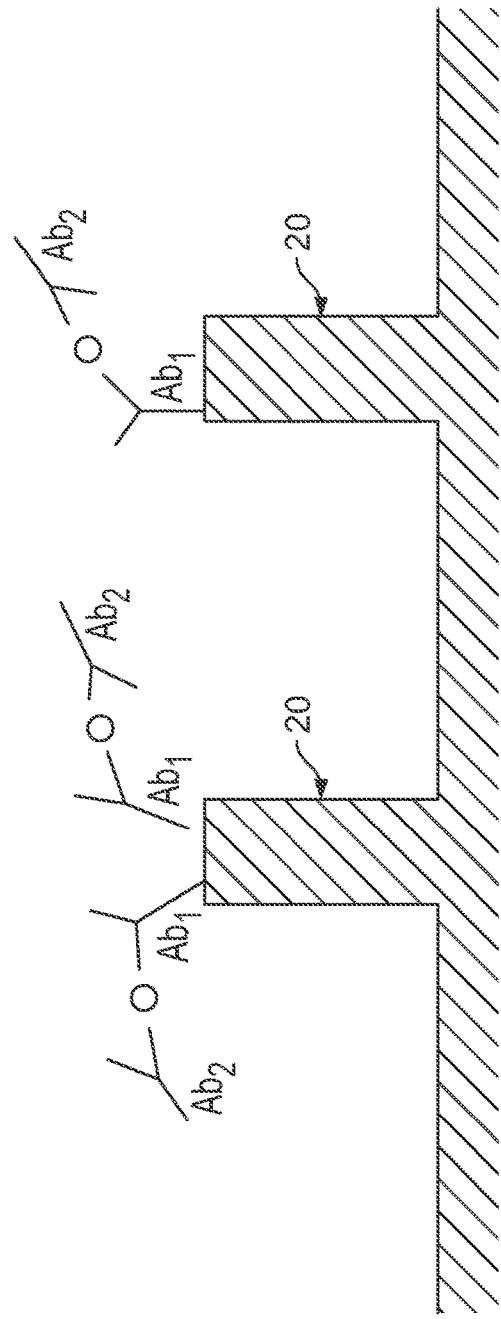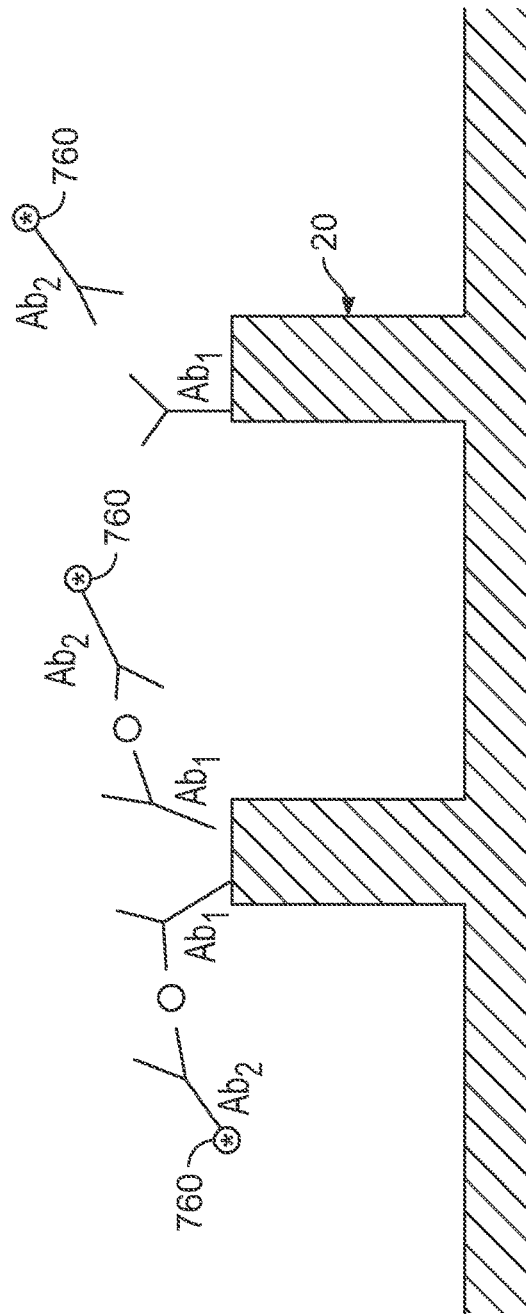

Beads pre-coated with antibodies

Antibodies are linked with oligo through a cleavable unit

An example of 2x5 nanoneedle array, different spot is printed with complementary oligos to the oligos linked with antibodies Cleave off, hybridize on chip and read signal on chip

NANOSENSORS AND USE THEREOF

CROSS-REFERENCE TO RELATED APPLICATIONS

This application is the national stage of International (PCT) Patent Application No. PCT/US2020/020204, filed on Feb. 27, 2020, which claims the benefit of, and priority to, U.S. Provisional Application Ser. No. 62/811,543, filed Feb. 28, 2019, U.S. Provisional Application Ser. No. 62/811,559, filed Feb. 28, 2019, U.S. Provisional Application Ser. No. 62/811,579, filed Feb. 28, 2019, and U.S. Provisional Application Ser. No. 62/811,041, filed Feb. 27, 2019, the entire disclosures of which are incorporated herein by reference.

FIELD OF THE INVENTION

The present invention relates generally to nanostructure-based analyte detection and/or quantification systems and, more specifically, relates to nanostructure-based analyte detection and/or quantification systems that facilitate quantification of analytes with high sensitivity over a large dynamic range.

BACKGROUND

Over the years, the detection and quantification of analytes has been critical in the diagnosis and treatment of numerous diseases or disorders, as well as the development of new therapies and treatment modalities. Significant progress has been made in the development of analyte detection and quantification systems, including solid or solution based assays, such as blotting-based technologies such as Western blots, enzyme linked immunoassays (ELISAs), digital ELISAs, micro-fluidic-based ELISA technologies, and automated bead-based assays. However, challenges remain.

For example, although certain analytes act as biomarkers for certain diseases or disorders, their concentrations may vary significantly between subjects or even between different samples, for example, tissue or fluid samples, harvested from the same subject. Furthermore, the existence of quantification systems for measuring ultra-low concentrations of certain analytes in certain body fluids has particularly hindered the efforts of discovering and validating biomarkers. For example, the quantitation range of commercial assays such as an ELISA is typically at or above 100 pg/mL. However, in Alzheimer's disease, for example, various proteins such as amyloid β (Aβ) protein and Tau protein, which have become recognized biomarkers for the disease, are typically present in peripheral blood (versus cerebrospinal fluid) at levels at or below 1 pg/mL due to the blood-brain-barrier. As a result, these levels are one or two orders of magnitude below the detection limit of a standard ELISA. Although digital ELISA assays may facilitate the quantification of sub-pg/mL levels of various biomarkers, these assays are typically optimized for low concentration measurements and do not have a large dynamic range. In other words, digital ELISAs typically can measure concentrations from 0.01-0.1 pg/mL to 10-100 pg/mL, representing a dynamic range of about 3-4 orders of magnitude.

Similarly, cytokine release syndrome (CRS), a systemic inflammatory response observed with monoclonal antibody-based therapies and adoptive T cell treatments (e.g., CAR-T therapies), has become a major issue. CRS can present as a mild reaction requiring minimally invasive supportive care up to a severe systemic response potentially resulting in the death of the subject undergoing treatment. Monitoring a CRS response during these therapies can be challenging given the wide range of biomarker concentrations, small sample volumes, and long assay times. Current analytical methods are unable to address these needs, limiting the precision of CAR-T therapies and effective management of its side effects. Emerging studies have identified a panel of predictive biomarkers (including C-reactive protein (CRP) and ferritin, and various cytokines, such as IFNγ, IL-6, and TNFα), that may be used to manage dosing regimens and identify the need for early intervention. However, CRP and ferritin may vary in concentration from 10 ng/mL to 10 mg/mL (6 orders of magnitude) whereas IL-6, and IFNγ, may vary in concentration from 1 pg/mL to 0.1 μg/mL (7 orders of magnitude). Cumulatively, these analytes can span a concentration range (1 pg/mL-10 mg/mL) representing a dynamic range of 10 orders of magnitude (10 logs). At present, no known detection and quantification system can provide a dynamic range of 6 or more orders of magnitude, with the requisite lower limit of detection and high multiplexability for measuring different analytes, in a rapid single test and that can differentiate between low, medium or high grade responses.

Accordingly there is an ongoing need for a detection and quantification system that facilitates the quantification of one of more analytes over a large dynamic range with the requisite sensitivity.

SUMMARY OF THE INVENTION

The invention provides a sensor for detecting the presence of and/or for quantifying, with high sensitivity over a large dynamic range, the amount of an analyte in a sample of interest, a cartridge incorporating one or more such sensors, a detection system, and methods of using such a sensor, cartridge and system, to quantify the amount of analyte in a sample.

In one aspect, the invention provides a sensor for detecting the presence, or quantifying the amount, of an analyte in a sample of interest. The sensor comprises a first region and a second region. The first region comprises a first series of nanostructures capable of binding the analyte and producing a detectable signal indicative of a concentration of the analyte in the sample within a first concentration range. The second region comprises a second series of different nanostructures capable of binding the analyte and producing a detectable signal indicative of a concentration of the analyte in the sample within a second, different concentration range, wherein the sensor is capable of quantifying the amount of analyte in a sample across both the first concentration range and the second concentration range.

In another aspect, the invention provides a sensor for detecting the presence, or quantifying the amount, of an analyte in a sample of interest. The sensor comprises a first region and a second region. The first region comprises a first series of nanostructures capable of binding the analyte and producing a detectable signal indicative of a concentration of the analyte in the sample within a first concentration range, wherein individual nanostructures of the first series that bind the analyte are optically detected upon binding the analyte, whereupon the concentration of analyte in the sample, if within the first concentration range, is determined from a number of individual nanostructures in the first series that have bound one or more molecules of analyte. The second region comprises a second series of different nanostructures capable of binding the analyte and producing a detectable signal indicative of a concentration of the analyte in the sample within a second, different concentration range, wherein the concentration of analyte in the sample, if within the second concentration range, is determined by detection of a substantially uniform change in an optically detectable property of the nanostructures in the second region as a function of the concentration of the analyte, wherein the sensor is capable of quantifying the amount of analyte in a sample across both the first concentration range and the second concentration range.

In each of the foregoing aspects, the first concentration range has a lower detectable value than that of the second concentration range and/or the second concentration range has a higher detectable value than that of the first concentration range. It is contemplated that the first concentration range can overlap the second concentration range.

In another aspect, the invention provides a sensor for detecting the presence, or quantifying the amount, of an analyte in a sample of interest. The sensor comprises a first region comprising a first series of nanostructures capable of binding the analyte and producing a detectable signal indicative of a concentration of the analyte in the sample within a first concentration range, wherein individual nanostructures of the first series that bind the analyte are optically detected upon binding the analyte, whereupon the concentration of analyte in the sample, if within the first concentration range, is determined from a number of individual nanostructures in the first series that have bound molecules of analyte.

In each of the foregoing aspects, the first region of the sensor comprises one or more of: (i) center-to-center spacing of adjacent nanostructures of at least 1 μm; (ii) a minimum cross-sectional dimension or diameter of each nanostructure of at least 10 nm; (iii) a maximum cross-sectional dimension or diameter of each nanostructure of no more than 200 nm; or (iv) a height of each nanostructure in a range of 50 nm to 1000 nm. The sensor optionally further comprises one or more of a (i) a fiducial marker or (ii) a nanostructure fabrication control feature.

In another aspect, the invention provides a sensor for detecting presence, or quantifying an amount, of an analyte in a sample of interest. The sensor comprises a first region comprising a first series of nanostructures capable of binding the analyte and producing a detectable signal indicative of a concentration of the analyte in the sample within a first concentration range, wherein the concentration of analyte in the sample, if within the first concentration range, is determined by analog detection of a substantially uniform change in an optically detectable property of the nanostructures in the first region as a function of the concentration of the analyte. The first region further comprises one or more of: (i) center-to-center spacing of adjacent nanostructures of at least 1 μm; (ii) a minimum cross-sectional dimension or diameter of each nanostructure of at least 100 nm; (iii) a maximum cross-sectional dimension or diameter of each nanostructure of no more than 300 nm; or (iv) a height of each nanostructure in a range of 50 nm to 1,000 nm. The sensor optionally further comprises a second region comprising one or more of (i) a fiducial marker or (ii) a nanostructure fabrication control feature.

It is contemplated that the sensor of any of the foregoing aspects of the invention may comprises one or more of the following features. For example, it is contemplated that the sensor may further comprise a third region comprising a third series of further different nanostructures capable of binding the analyte and producing a detectable signal indicative of the concentration of the analyte in the sample within a third concentration range, wherein the sensor is capable of quantifying the amount of the analyte in the sample across the first, second and/or third concentration ranges. It is also contemplated that the sensor may also include additional series of nanostructures operative to detect and/or quantify analyte in additional concentration ranges.

Similarly, the nanostructures in any second series can comprise one of more of (i) an average height, (ii) an average volume, (iii) an average surface area, (iv) an average mass, and (v) an average number of analyte binding sites, that is greater than that of the nanostructures in the first series.

Furthermore, whenever the sensor comprises a third series, the nanostructures of the third series can comprise one of more of (i) an average height, (ii) an average volume, (iii) an average surface area, (iv) an average mass, and (v) an average number of analyte binding sites, that is greater than that of the nanostructures in any second series.

The nanostructures in the first series, and where applicable, the second and third series (and other additional series), are functionalized with a binding agent that binds the analyte, for example, a biological binding agent that binds the analyte. The biological binding agent can be, for example, an antibody, an aptamer, a member of a ligand-receptor pair, an enzyme, or a nucleic acid. Under certain circumstances, it may be advantageous to use a binding agent in the first series that has a higher binding affinity for the analyte than the binding agent in a second, third or subsequent series.

The sensor may be designed to detect and/or quantify any analyte of interest in a sample. For example, the analyte may be a biological molecule, for example, a protein, peptide, carbohydrate, glycoprotein, glycopeptide, lipid, lipoprotein, nucleic acid, or nucleoprotein. Furthermore, a nanostructure or series of nanostructures in a given sensor may be configured to bind, detect and/or quantify a plurality of different analytes simultaneously or sequentially. For example, the sensor can comprise a plurality of different binding agents for detecting a corresponding plurality of different analytes in the test sample to facilitate multiplex analysis of multiple analytes, simultaneously in the same well on a sensor.

It is understood that any of the foregoing sensors is capable of detecting the concentration of analyte in the sample across a concentration range (also referred to as dynamic range) spanning at least 3, 4, 5, 6, 7, 8, 9, 10, 11 or 12 orders of magnitude (or 3, 4, 5, 6, 7, 8, 9, 10, 11 or 12 logs) avoiding the need to dilute or concentrate analytes in a sample of interest. In certain embodiments, the sensor is capable of detecting the concentration of analyte in the sample across a range spanning at least 5, 6, 7, 8 or 9 orders of magnitude (or 5, 6, 7, 8 or 9 logs). The sensor may be configured to measure the concentration of a given analyte in the range from less than 1 pg/mL to greater than 100 ng/mL, less than 0.1 pg/mL to greater than 1 μg/mL, from less than 0.01 pg/mL to greater than 100 μg/mL, from less than 1 fg/mL to greater than 0.1 mg/mL, or from less than 0.1 fg/mL to greater than 1 mg/mL, where, for example, the sample does not need to be diluted prior to application to the sensor.

The sensor may detect the analyte in a variety of samples, for example, a body fluid, a tissue extract, and/or a cell supernatant. Exemplary body fluids include, for example, blood, serum, plasma, urine, cerebrospinal fluid, or interstitial fluid.

The sensor can be configured to detect the binding of an analyte via a change in an optically detectable property (for example, color, light scattering, refraction, or resonance (for example, surface plasmonic resonance, electric resonance, electromagnetic resonance, and magnetic resonance)) of at least one series of nanostructures.

It is contemplated that the sensors may be configured in a variety of different ways. For example, at least one of the first, second or third series of nanostructures can comprise an array. Alternatively, each of the first, second and third series of nanostructures can comprise an array. It is contemplated that the sensor may comprise a single series of nanostructures or a plurality of series of nanostructures, for example, a plurality of series of nanostructures operative to detect analyte within different concentration ranges. When the sensor comprises a plurality of series of nanostructures, the different series of nanostructures may operate (i) in the same manner (for example, by digital detection where single nanostructures are detected and/or quantified, or by analog detection where a substantially uniform change in an optical property of the nanostructures within a given series as a function of concentration is detected) or (ii) in a different manner, for example by a combination of digital detection and analog detection. Furthermore, it is contemplated that the sensor may comprise a plurality of different series that operate by digital detection and/or analog detection. For example, the sensor may comprise a plurality of series that operate to detect an analyte by digital detection within the same concentration range and/or a plurality of series that operate to detect an analyte by analog detection over different concentration ranges.

For example, during digital detection, in the first series of nanostructures, individual nanostructures that bind the analyte are detected upon binding either a single molecule of analyte or less than a predetermined number of molecules of the analyte, whereupon the concentration of analyte in the sample, if present in the first concentration range, is determined from a number of individual nanostructures in the first series that have bound molecules of the analyte. For example, the concentration of analyte in the sample is determined by digital counting of the number of individual nanostructures in the first series that have bound the analyte relative to, for example, either (i) a remaining number of individual nanostructures that have not bound analyte or (ii) a total number of nanostructures in the first series.

Similarly, the concentration of analyte, if within the second range or the third range, can be determined by digital counting of the number of individual nanostructures in the second and/or third series that have bound the analyte relative to, for example, either (i) a remaining number of individual nanostructures in the appropriate series that have not bound analyte or (ii) a total number of nanostructures in the corresponding second and/or third series. In other words, the concentration of analyte in a sample across both the first concentration range, the second concentration range, and the optional third (or more) concentration range is determined from a number of individual nanostructures in each of the first series, the second series, and/or the optional third (or more) series that have bound molecules of the analyte. It is contemplated that the sensor also further comprises additional series (for example, four, five, six series, etc.) of nanostructures depending upon the dynamic range and/or sensitivity desired for a given assay.

Alternatively or in addition, the concentration of analyte, if within the second concentration range or the optional third concentration range, can be determined by analog detection of a substantially uniform change in an optically detectable property of the nanostructures in the second region and/or the third region as a function of the concentration of the analyte. For example, the change in the optically detectable property can be a color change created by the second series in the second region and/or the optional third series in the third region as a function of the concentration of the analyte. In other words, the concentration of analyte in a sample across both the second concentration range and optional third (or more) concentration range(s) is determined by analog detection of a substantially uniform change in an optically detectable property of the nanostructures in each of the second region and/or the third region. It is contemplated that the sensor also further comprises additional series (for example, four, five, six series, etc.) of nanostructures depending upon the dynamic range and/or sensitivity desired for a given assay.

It is contemplated that the nanostructures in a given series can be planar-faced and/or curve-faced nanostructures. The nanostructures can be disposed upon a planar support and/or a flexible substrate, where the nanostructures can be integral with the planar support and/or the flexible substrate. The nanostructures can fabricated from a semi-conductive material (for example, silicon) or a metal.

It is contemplated that the sensor may further comprise a fiducial marker, for example, a fiducial marker that is optically detectable by light field microscopy and/or dark field microscopy. The fiducial marker can be used to calibrate the location of the sensors within the field of detection by the detection system.

In another aspect, the invention provides a cartridge for detecting the presence, or quantifying the amount, of an analyte in a sample of interest, the cartridge comprising a housing defining at least one well comprising any one or more of the foregoing sensors. The housing may define a plurality of wells, each well comprising any one or more of the foregoing sensors.

In another aspect, the invention provides a system for detecting the presence, or quantifying the amount, of an analyte in a sample of interest. The system comprises (a) a receiving chamber for receiving any one or more of the foregoing sensors any one or more of the foregoing cartridges; (b) an energy source for interrogating (for example, a light source for illuminating) at least the first series and/or any second series and/or any third series of nanostructures; (c) a detector for detecting a change in a property (for example, an optical property) in at least the first series and/or any second series and/or any third series of nanostructures; and optionally (d) a computer processor implementing a computer algorithm that identifies an interface between the first concentration range and any second concentration range and optionally an interface between any second concentration range and optionally any third concentration range.

In the case of an optical detection system, when an algorithm determines whether to transition a concentration curve between digital and analog detection, it is contemplated that the algorithm comprises the steps of: (a) measuring the nanostructures that have changed (flipped) from one state to another relative to the nanostructures in the first series upon application of the solution to be tested; (b) measuring the color space changes of nanostructures in the second series upon application of the solution to be tested; and (c) if the color space change of the second series is greater than a preselected threshold value then use the analog measurements identified in step (b) and if the color space changes of the second series is less than the preselected threshold value, then use the digital measurements identified in step (a).

In another aspect, the invention provides a method of detecting the presence, or quantifying the amount, of an analyte in a sample of interest, for example, a body fluid, tissue extract, or a cell supernatant. The method comprises:

(a) applying at least a portion of the sample to any one or more of the foregoing sensors; and (b) detecting a change in a property (for example, an optical property) of the first series and/or any second series and/or any third series of nanostructures thereby to detect the presence, or quantify the amount, of the analyte in the sample.

It is contemplated that the method may include one or more or the following features. For example, the method may be capable of detecting an analyte with a concentration range of at least 3, 4, 5, 6, 7, 8, 9, 10, 11, or 12 logs, e.g., a concentration range of at least 5, 6, 7, 8, or 9 logs. The sensor may be capable of detecting analyte in a concentration range from less than 1 fg/mL to greater than 1 mg/mL. As a result, the sample may not need to be diluted prior to application to the sensor.

In another aspect, the invention provides a method of detecting presence, or quantifying an amount, of an analyte in a sample of interest, for example, a body fluid, tissue extract, or a cell supernatant. The method includes applying a portion of the sample to a sensor comprising a first region and a second region. The first region comprises a first series of nanostructures capable of binding the analyte and producing a detectable signal indicative of a concentration of the analyte in the sample within a first concentration range. The second region comprises a second series of different nanostructures capable of binding the analyte and producing a detectable signal indicative of a concentration of the analyte in the sample within a second, different concentration range. The regions are interrogated, for example, using electromagnetic radiation to detect detectable signals from the first and second series of nanostructures, the signals being indicative of the presence and/or amount of analyte in the sample. The presence and/or amount of the analyte can then be determined from the detectable signals thereby to detect the presence, or to quantify the amount of, the analyte in the sample across both the first concentration range and the second concentration range.

In another aspect, the invention provides a method of detecting presence, or quantifying an amount, of an analyte in a sample of interest, for example, a body fluid, tissue extract, or a cell supernatant. The method includes applying a portion of the sample to a sensor comprising a first region and a second region. The first region comprises a first series of nanostructures capable of binding the analyte and producing a detectable signal indicative of a concentration of the analyte in the sample within a first concentration range, wherein individual nanostructures of the first series that bind the analyte are optically detected upon binding the analyte, whereupon the concentration of analyte in the sample, if within the first concentration range, is determined from a number of individual nanostructures in the first series that have bound molecules of analyte. The second region comprises a second series of different nanostructures capable of binding the analyte and producing a detectable signal indicative of a concentration of the analyte in the sample within a second, different concentration range, wherein the concentration of analyte in the sample, if within the second concentration range, is determined by analog detection of a substantially uniform change in an optically detectable property of the nanostructures in the second region as a function of the concentration of the analyte. The regions are interrogated, for example, using electromagnetic radiation to detect detectable signals from the first and second series of nanostructures, the signals being indicative of the presence and/or amount of analyte in the sample. The presence and/or amount of the analyte can then be determined from the detectable signals thereby to detect the presence, or to quantify the amount of, the analyte in the sample across both the first concentration range and the second concentration range.

It is contemplated that, in each of the foregoing methods, the nanostructures in any second series comprise one of more of (i) an average height, (ii) an average volume, (iii) an average surface area, (iv) an average mass, and (v) an average number of analyte binding sites, that is greater than that of the nanostructures in the first series.

Other advantages and novel features of the present invention will become apparent from the following detailed description of various non-limiting embodiments of the invention when considered in conjunction with the accompanying figures.

DESCRIPTION OF THE DRAWINGS

FIG. 2A is a schematic representation of different formats of series of nanostructures in a sensor of interest.

FIG. 3A is a schematic illustration depicting a sensor containing both digital and analog (color shifting) nanostructure arrays, in accordance with an embodiment of the invention. FIG. 3B is a pictorial representation depicting the quantification of Tau protein over a 6 log dynamic range by a combination of digital single molecule quantification (left hand panel) and by analog quantification (right hand panel).

FIG. 3C is an image depicting the operability of a digital sensor as function of analyte concentration.

FIG. 7 is a schematic illustration depicting cross-sectional views of exemplary nanostructures, in accordance with embodiments of the invention.

FIG. 8 is a schematic illustration depicting cross-sectional views of exemplary nanostructures composed of two different materials, in accordance with embodiments of the invention.

FIGS. 10A-10G are a series of cross-sectional schematic diagrams illustrating the fabrication of a series of exemplary nanostructures by deposition of a layer on a substrate, spin coating a photoresist on the deposited layer, patterning and developing the resist, evaporating metal on the resist, removal of the resist in a solution, etching the substrate, and removing the photoresist, in accordance with an embodiment of the invention.

FIGS. 11A-11F are a series of cross-sectional schematic diagrams illustrating the fabrication of a series of exemplary nanostructures by coating two layers on a substrate, patterning the top layer resist, developing the resist, evaporating materials on the patterned resist, lift-off and spin additional low viscosity materials to achieve a particular surface condition, in accordance with an embodiment of the invention.

FIG. 12A-12F are a series of cross-sectional schematic diagrams illustrating the fabrication of a series of exemplary nanostructures by patterning photoresist on an oxide substrate, developing the resist, depositing silicon on the resist, lift-off, and growth of silicon to grow additional structures on the patterned substrate, in accordance with an embodiment of the invention.

FIGS. 13A-13D are a series of cross-sectional schematic diagrams illustrating the patterning of photoresist with a mold, in accordance with an embodiment of the invention.

FIG. 14A is a schematic illustration showing a silicon wafer with multiple series of nanostructures and FIG. 14B is a schematic illustration showing an enlarged image of a single series of nanostructures, in accordance with an embodiment of the invention.

FIG. 28 is schematic representation depicting an exemplary label-free immunoassay.

FIG. 29 is a schematic representation depicting an exemplary label-based immunoassay.

DETAILED DESCRIPTION

The invention is based in part upon the discovery that it is possible to create a sensor for detecting the presence and/or quantifying, with high sensitivity over a large dynamic range, the amount of an analyte in a sample of interest, a cartridge incorporating such a sensor, a detection system, and methods of using such a sensor, cartridge and system, to detect and/or quantify the amount of analyte in a sample.

Figure 1:
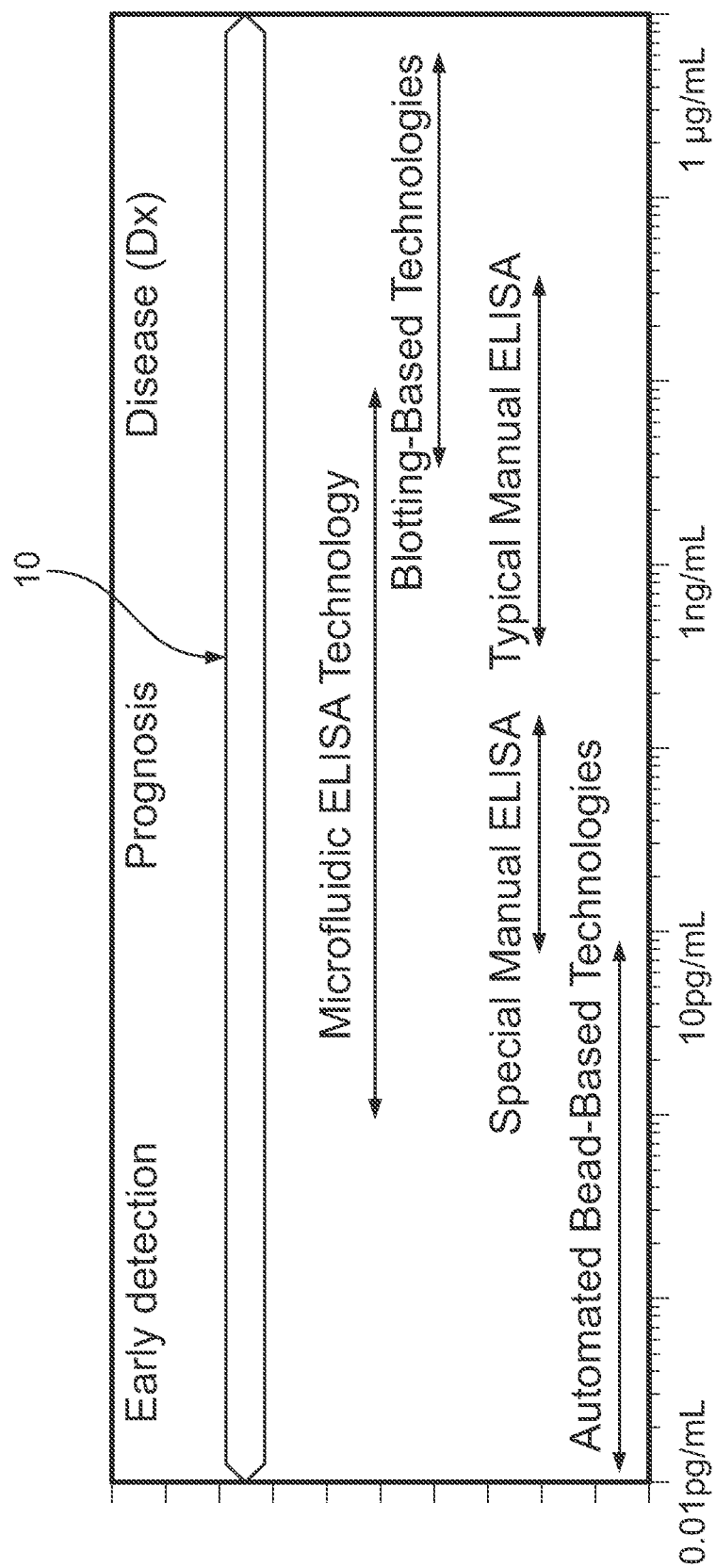
FIG. 1 is a schematic illustration showing the dynamic range of a sensor in accordance with an embodiment of the invention in comparison to prior art assays.

FIG. 1 illustrates the dynamic range 10 achievable with a sensor of the invention that can detect analytes in a sample within a concentration range between less than 0.01 pg/mL (10 fg/mL) and 1 μg/mL or greater (at least 8 logs). In general, other commercially available assay systems (for example, typical manual ELISA, special manual ELISA, microfluidic-based ELISA assays, blotting-based technologies (for example, Western blotting and dot blotting technologies) and automated bead-based technologies) can measure analytes in samples of interest but cannot measure analytes over the entire dynamic range achievable with a sensor disclosed herein. As a result, use of the sensor of the invention may facilitate the measurement of concentrations of analyte over a concentration range that heretofore could only be achieved using a combination of prior art assay systems.

I. Sensor Considerations (A) Sensor Configurations

It is contemplated that the sensor may comprise nanostructures in a variety of configurations. For example, as shown in FIG. 2A, the sensor may comprise a first series of nanostructures 20d, for example, a series of nanostructures configured for digital quantification (FIG. 2A(i)); a second series of nanostructures 20a, for example, a series of nanostructures configured for analog quantification (FIG. 2A(ii)); two series of nanostructures 20d (FIG. 2A(iii)); two series of nanostructures 20a (FIG. 2A(iv)); two series of nanostructures one of 20d and one of 20a (FIG. 2A(v)); and three series of nanostructures one of 20d and two of 20a (FIG. 2A(vi)). It is contemplated that the sensor may comprise other series of nanostructures in different configurations depending upon the analyte to be detected and the dynamic range desired.

As used herein, the term "nanostructure" is understood to mean any structure, for example, a nanosensor, that has at least one dimension having a length in the range of at least 1 nm to less than 1,000 nm. As used herein, the term "digital quantification" is understood to mean a quantification process whereby individual nanostructures in a series of nanostructures are detected (for example, optically detected) that flip from one state to another upon binding one or more analytes. A "digital series" or "digital array" is understood to mean a respective series or array of nanostructures configured to permit digital quantification.

As used herein, the term "analog quantification" is understood to mean a quantification process whereby a substantially uniform change in a detectable property (for example, optically detectable property, for example, a color) of nanostructures in a series of nanostructures is detected, when the nanostructures bind a plurality of analytes. In certain embodiments, changes in the detectable property (for example, color changes) occur as a function of the concentration of analyte in a sample of interest across a precalibrated concentration range of the analyte to be detected. The term "substantially uniform" is understood to mean that, at least 60%, 70%, 80%, 90% or 95% of the nanostructures share the same detectable property, for example, color. An "analog series" or "analog array" is understood to mean a respective series or array of nanostructures configured to permit analog detection.

In one exemplary sensor for detecting the presence, or quantifying the amount, of an analyte in a sample of interest, the sensor comprises a first region and a second region. The first region comprises a first series of nanostructures capable of binding the analyte and producing a detectable signal indicative of a concentration of the analyte in the sample within a first concentration range. The second region comprises a second series of different nanostructures capable of binding the analyte and producing a detectable signal indicative of a concentration of the analyte in the sample within a second, different concentration range, wherein the sensor is capable of quantifying the amount of analyte in a sample across both the first concentration range and the second concentration range. The first concentration range can have a lower detectable value than that of the second concentration range and/or the second concentration range can have a higher detectable value than that of the first concentration range. It is contemplated that the first concentration range can overlap the second concentration range.

It is understood that the sensors described herein are capable of detecting the concentration of analyte in the sample across a range (also referred to as dynamic range) spanning at least 3, 4, 5, 6, 7, 8, 9, 10, 11 or 12 orders of magnitude (or 3, 4, 5, 6, 7, 8, 9, 10, 11 or 12 logs). In certain embodiments, the sensor is capable of detecting the concentration of analyte in the sample across a concentration range spanning at least 5, 6, 7, 8 or 9 orders of magnitude (or 5, 6, 7, 8 or 9 logs). The sensor may be configured to measure the concentration of a given analyte in the range from less than 1 pg/mL to greater than 100 ng/mL, from less than 0.1 pg/mL to greater than 1 μg/mL, or from less than 0.01 pg/mL to greater than 100 μg/mL, or from less than 1 fg/mL to greater than 1 mg/mL, where, for example, the sample does not need to be diluted prior to application to the sensor.

In one exemplary sensor, the first region comprises a first series of nanostructures capable of binding the analyte and producing a detectable signal indicative of a concentration of the analyte in the sample within a first concentration range, wherein individual nanostructures of the first series that bind the analyte are detected (for example, optically detected) upon binding the analyte, whereupon the concentration of analyte in the sample, if within the first concentration range, is determined from a number of individual nanostructures in the first series that have bound molecules of analyte. The second region comprises a second series of different nanostructures capable of binding the analyte and producing a detectable signal indicative of a concentration of the analyte in the sample within a second, different concentration range, wherein the concentration of analyte in the sample, if within the second concentration range, is determined by analog detection of a substantially uniform change in a detectable property (for example, an optically detectable property, such as color) of the nanostructures in the second region as a function of the concentration of the analyte, wherein the sensor is capable of quantifying the amount of analyte in a sample across both the first concentration range and the second concentration range.

The first concentration range has a lower detectable value than that of the second concentration range and/or the second concentration range has a higher detectable value than that of the first concentration range. It is contemplated that the first concentration range can overlap the second concentration range.

In each of the foregoing sensors, the first region of the sensor optionally comprises one or more of: (i) center-to-center spacing of adjacent nanostructures of at least 1 μm; (ii) a minimum cross-sectional dimension or diameter of each nanostructure of at least 10 nm; (iii) a maximum cross-sectional dimension or diameter of each nanostructure of no more than 200 nm; or (iv) a height of each nanostructure in a range of 50 nm to 1000 nm. The sensor optionally further comprises one or more of a (i) a fiducial marker or (ii) a nanostructure fabrication control feature.

It is contemplated that any of the sensors may comprises one or more of the following features. For example, it is contemplated that the sensor may further comprise a third region comprising a third series of further different nanostructures capable of binding the analyte and producing a detectable signal indicative of the concentration of the analyte in the sample within a third concentration range, wherein the sensor is capable of quantifying the amount of the analyte in the sample across the first, second and/or third concentration ranges.

Similarly, the nanostructures in any second series can comprise one of more of (i) an average height, (ii) an average volume, (iii) an average surface area, (iv) an average mass, and (v) an average number of analyte binding sites, that is greater than that of the nanostructures in the first series.

Furthermore, whenever the sensor comprises a third series, the nanostructures of the third series can comprise one of more of (i) an average height, (ii) an average volume, (iii) an average surface area, (iv) an average mass, and (v) an average number of analyte binding sites, that is greater than that of the nanostructures in any second series.

The nanostructures in the first series, and where applicable, the second and third series, are functionalized with a binding agent that binds the analyte, for example, binding agent, for example, a biological binding agent, that binds the analyte. The biological binding agent can be, for example, an antibody, an aptamer, a member of a ligand-receptor pair, an enzyme, or a nucleic acid. Under certain circumstances, it may be advantageous to use a binding agent in the first series that has a higher binding affinity for the analyte than the binding agent in a second, third or subsequent series.

The sensor may be designed to detect and/or quantify any analyte of interest in a sample. For example, the analyte may be a biological molecule, for example, a protein, peptide, carbohydrate, glycoprotein, glycopeptide, lipid, lipoprotein, nucleic acid, or nucleoprotein. Furthermore, a nanostructure or series of nanostructures in a given sensor may be configured to bind, detect and/or quantify a plurality of different analytes simultaneously or sequentially. For example, the sensor can comprise a plurality of different binding agents for detecting a corresponding plurality of different analytes in the test sample.

The sensor can be configured to detect the binding of an analyte via change in an optical property, electrical property, or mechanical property. For example, sensor can be configured to detect the binding of an analyte via a change in an optically detectable property (for example, color, light scattering, refraction, or resonance (for example, surface plasmonic resonance, electric resonance, electromagnetic resonance, and magnetic resonance)) of at least one series of nanostructures.

It is contemplated that the sensors may be configured in a variety of different ways. For example, at least one of the first, second or third series of nanostructures can comprise an array of nanostructures. Alternatively, each of the first, second and third series of nanostructures can comprise an array of nanostructures. It is contemplated that sensor may comprise a single series of nanostructures or a plurality of series of nanostructures, for example, a plurality of series of nanostructures operative to detect analyte within different concentration ranges. When the sensor comprises a plurality of series of nanostructures, the different series of nanostructures may operate (i) in the same manner (for example, via digital detection where single nanostructures are detected or quantified, or via analog detection where a cumulative change in an optical property of the nanostructures within a given series is detected as a function of concentration) or (ii) in a different manner, for example by a combination of digital detection and analog detection. Furthermore, it is contemplated that the sensor may comprise a plurality of different series that operate by digital detection and/or analog detection. For example, the sensor may comprise a plurality of series that operate to detect an analyte by digital detection within the same concentration range and/or a plurality of series that operate to detect an analyte by analog detection over different concentration ranges.

For example, during digital detection, in the first series of nanostructures, individual nanostructures that bind the analyte are detected upon binding either a single molecule of analyte or less than a predetermined number of molecules of the analyte, whereupon the concentration of analyte in the sample, if present in the first concentration range, is determined from a number of individual nanostructures in the first series that have bound molecules of the analyte. For example, the concentration of analyte in the sample is determined by digital counting of the number of individual nanostructures in the first series that have bound the analyte relative to either (i) a remaining number of individual nanostructures that have not bound analyte or (ii) a total number of nanostructures in the first series.

In this approach, a large number of nanostructures typically are densely patterned in a region of a sensor. When the number of the nanostructures is greater than the number of analytes to be detected, each nanostructure typically captures at most a single analyte, for example, based on mass transfer and Poisson distribution effects. Each nanostructure can have one of two states (for example, denoted as 1 or 0) depending upon whether analyte is bound or not. Accordingly, the number of nanostructures with state 1 after exposure to a sample with analytes can equal to the number of analytes. In certain embodiments, each individual nanostructure may have only a limited number of binding sites to capture one or a few (for example, less than 10) analytes, for example, proteins. Each nanostructure has a corresponding signal scale from 1 to a few (<10), and thus counting the number of molecules can be equivalent to counting the discrete signals of each nanostructure. The different signal level of the series of nanostructures forms a nanomosaic pattern, which can be detected.

Similarly, the concentration of analyte, if within the second range, as depicted in FIG. 2A(iii), or the third range, can be determined by digital counting of the number of individual nanostructures in the second and/or third series that have bound the analyte relative to either (i) a remaining number of individual nanostructures in the appropriate series that have not bound analyte or (ii) a total number of nanostructures in the corresponding second and/or third series. In other words, the concentration of analyte in a sample across both the first concentration range, the second concentration range, and the optional third (or more) concentration range is determined from a number of individual nanostructures in each of the first series, the second series, and/or the optional third (or more) series that have bound molecules of the analyte.

Alternatively or in addition, the concentration of analyte, if within the second concentration range or the optional third concentration range, can be determined by analog detection of a substantially uniform change in an optically detectable property of the nanostructures in the second region and/or the third region as a function of the concentration of the analyte. For example, the change in the optically detectable property can be a substantially uniform color change created by the second series and/or the optional third series as a function of the concentration of the analyte. In other words, the concentration of analyte in a sample across both the second concentration range and optional third (or more) concentration range(s) is determined by analog detection of a substantially uniform change in an optically detectable property of the nanostructures in each of the second region and/or the third region.

Each individual series (or region) of nanostructures may comprise binding sites for up to 10,000 molecules of the analyte of interest. Each region has a precalibrated continuous signal scale (analog scale) that relates to the number of proteins captured by the region. The analog scale for each region corresponds to a gradual change of physical signal for readout. Different scales may correspond to, for example, different colors from each region under a detector (for example, an optical detector). The region defines a nano-mosaic that has a continuum of a property change (for example, color change) as a function of analyte concentration. In the case of optical detection, for example, the different scales may relate to one or more of (i) a light intensity of the region under a microscope which has a continuum of intensity change as a function of concentration or (ii) an electronic measurement, e.g., a current or voltage signal of each region, which has a continuum of current or voltage signal as a function of concentration.

It is contemplated that the nanostructures in a given series can be planar-faced and/or curve-faced nanostructures. The nanostructures can be disposed upon a planar support and/or a flexible substrate, where the nanostructures can be integral with the planar support and/or the flexible substrate. The nanostructures can be fabricated from a semi-conductive material (for example, silicon) or a metal.

It is contemplated that the sensor may further comprise a fiducial marker, for example, a fiducial marker that is optically detectable by light field microscopy and/or dark field microscopy. The fiducial marker can be used to calibrate the location of the sensors within the field of detection by the detection system. The sensor may also contain one or more nanostructure fabrication controls that demonstrate, for example, that the nanostructures fabricated show a change in color as a function of the diameter of the nanostructures.

In another exemplary sensor, as depicted in FIG. 2A(i), the sensor comprises a first region comprising a first series of nanostructures capable of binding the analyte and producing a detectable signal indicative of a concentration of the analyte in the sample within a first concentration range, wherein individual nanostructures of the first series that bind the analyte are optically detected upon binding the analyte, whereupon the concentration of analyte in the sample, if within the first concentration range, is determined from a number of individual nanostructures in the first series that have bound molecules of analyte. The first region of the sensor optionally comprises one or more of: (i) center-to-center spacing of adjacent nanostructures of at least 1 μm; (ii) a minimum cross-sectional dimension or diameter of each nanostructure of at least 10 nm; (iii) a maximum cross-sectional dimension or diameter of each nanostructure of no more than 200 nm; or (iv) a height of each nanostructure in a range of 50 nm to 1000 nm. The sensor optionally further comprises a second region comprising one or more of a (i) a fiducial marker or (ii) a nanostructure fabrication control feature.

In another exemplary sensor, as depicted in FIG. 2A(ii), the sensor comprises a first region comprising a first series of nanostructures capable of binding the analyte and producing a detectable signal indicative of a concentration of the analyte in the sample within a first concentration range, wherein the concentration of analyte in the sample, if within the first concentration range, is determined by analog detection of a substantially uniform change in an optically detectable property of the nanostructures in the first region as a function of the concentration of the analyte. The first region further comprises one or more of: (i) center-to-center spacing of adjacent nanostructures of at least 1 μm; (ii) a minimum cross-sectional dimension or diameter of each nanostructure of at least 100 nm; (iii) a maximum cross-sectional dimension or diameter of each nanostructure of no more than 300 nm; or (iv) a height of each nanostructure in a range of 50 nm to 1000 nm. The sensor optionally further comprises a second region comprising one or more of (i) a fiducial marker or (ii) a nanostructure fabrication control feature.

The sensing region of the disclosed sensors is the physical spot that interacts with biological analytes. In certain embodiments, the sensing region is divided into different parts, with each part targeting a specific concentration range. At very low concentrations, an array of single molecule nanostructures can be used. If analytes are captured by the single molecule sensor, the sensor produces a digital "yes" signal, and thus, the concentration of molecules can be related to the counts of digital sensors. At low-to-medium concentration ranges, a larger nanostructure that has a certain dynamic range to produce an analog signal is used to measure the concentration of analytes. The read-out signal can be resonance spectrum associated with the nanostructure, or scattering intensity, etc. To improve the detection accuracy, an array of these sensors may be used to achieve a statistical average.

Figure 2B:
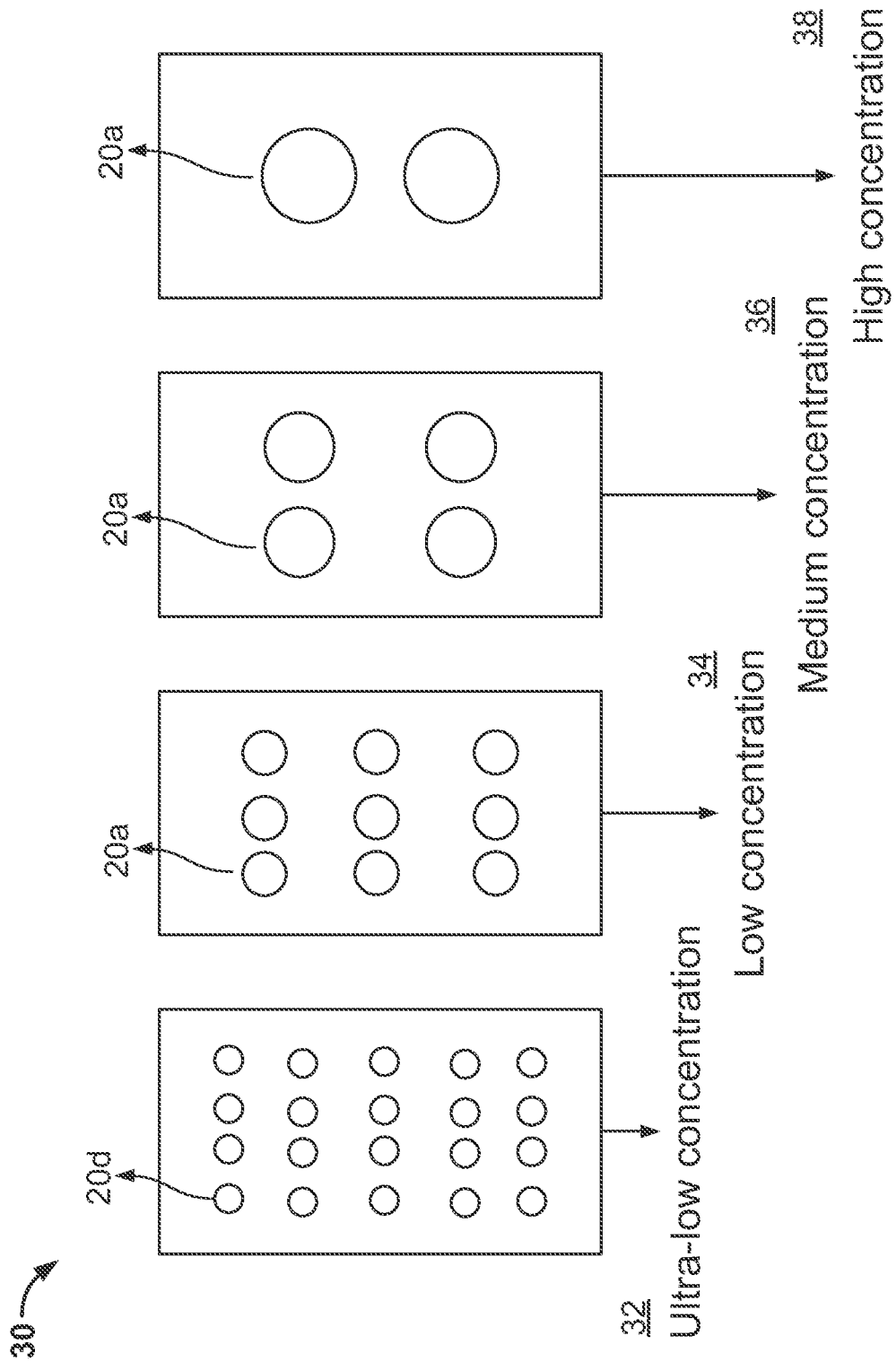
FIG. 2B is a schematic illustration depicting a series of exemplary sensors for measuring ultra-low, low, medium, and high concentrations of analytes.

As a non-limiting example, the sensing area of a sensor may be divided into multiple regions. By way of example, FIG. 2B is a schematic illustration of a sensor 30 with four sensor regions 32, 34, 36, 38. Each region comprises a series of nanostructures 20. In one embodiment, the series of nanostructures 20d of the ultra-low concentration sensor region 32 define a single molecule sensitivity. As a result, the concentration of analytes correlates with the number of single molecule nanostructures 20d that flip to produce a detectable signal, for example, a "yes" digital signal. The nanostructures 20a of the low, medium and high concentration sensor regions 34, 36, 38 have increasing size and, therefore, lower sensitivities but increasingly larger dynamic ranges. Each of the regions 32, 34 36, 38 are optimized for a specific dynamic range. Together, the results obtained from each region can be aggregated to provide a dynamic range that results from an aggregation of the dynamic ranges achievable by regions 32, 34, 36, 38.

Figure 3A:
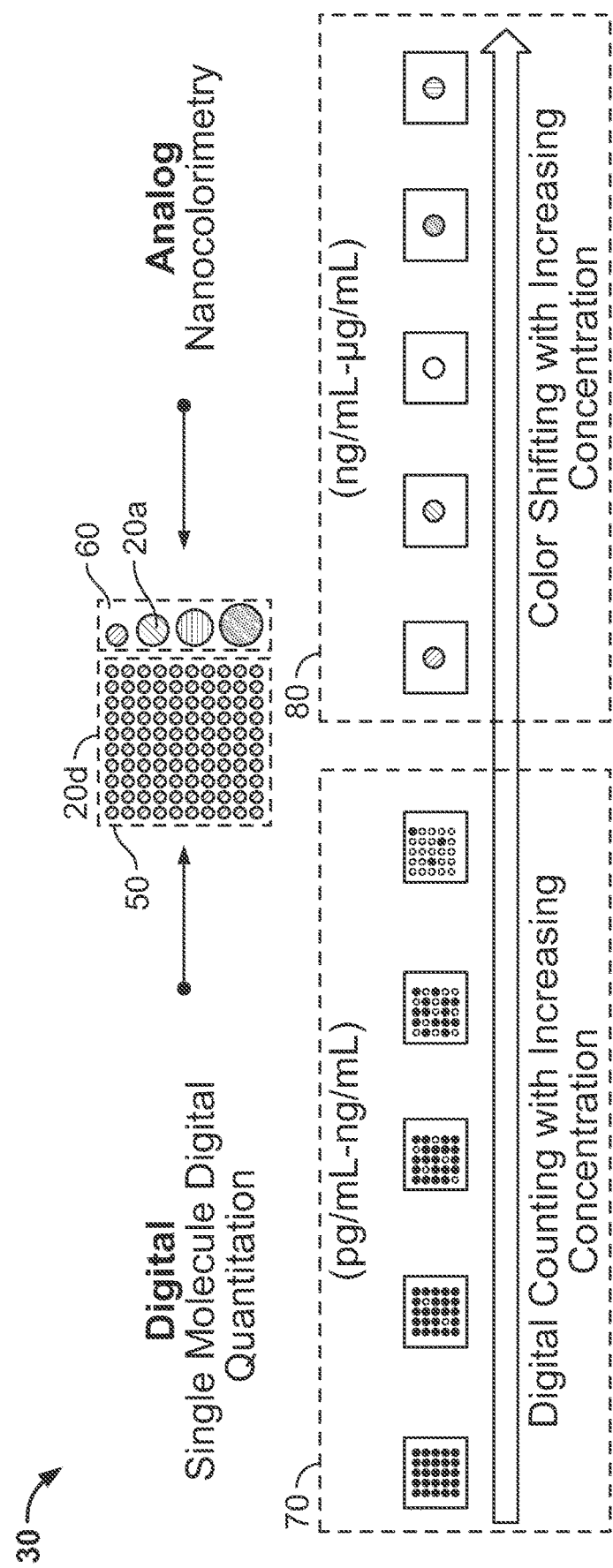
FIGS. 3A-3C show the operability of exemplary sensors of the invention in measuring analyte over a large dynamic range.

FIG. 3A depicts a schematic representation of an exemplary sensor and the quantification of an analyte of interested achieved using such a sensor. This sensor 30 includes a first region 50 with a series of nanostructures 20d configured for digital quantification and a second region 60 with a series of nanostructures 20a configured for analog quantification where shifts in color indicate different concentrations. In this example, digital quantification 70 is performed for analyte concentrations ranging from pg/mL to ng/mL, and analog quantification 80 is performed for analyte concentration ranging from ng/mL to μg/mL. When concentrations of analyte are in the range of pg/mL to ng/mL, the analyte concentration can be measured based on the number of nanostructures in the series in region 50 that change state (e.g., flip from one state to another). However, as the concentrations of analyte reach the upper limits of the detectable range, the sensor in region 50 becomes saturated and the sensor cannot quantify higher concentrations of analyte. Saturation of the first series may occur when at least 60%, 70%, 80%, 90%, 95%, or greater of the binding sites have bound an analyte. As a result, this sensor 30 also includes a plurality of series of nanostructures that change their optical properties (for example, detected as a color change) when the concentration of analyte in the sample falls within the range of analyte concentrations that is detectable by a given series of nanostructures. In this embodiment, the series of nanostructures in region 60 are calibrated to change their optical properties (for example, color) in adjacent or overlapping concentration ranges.

Figure 3B:
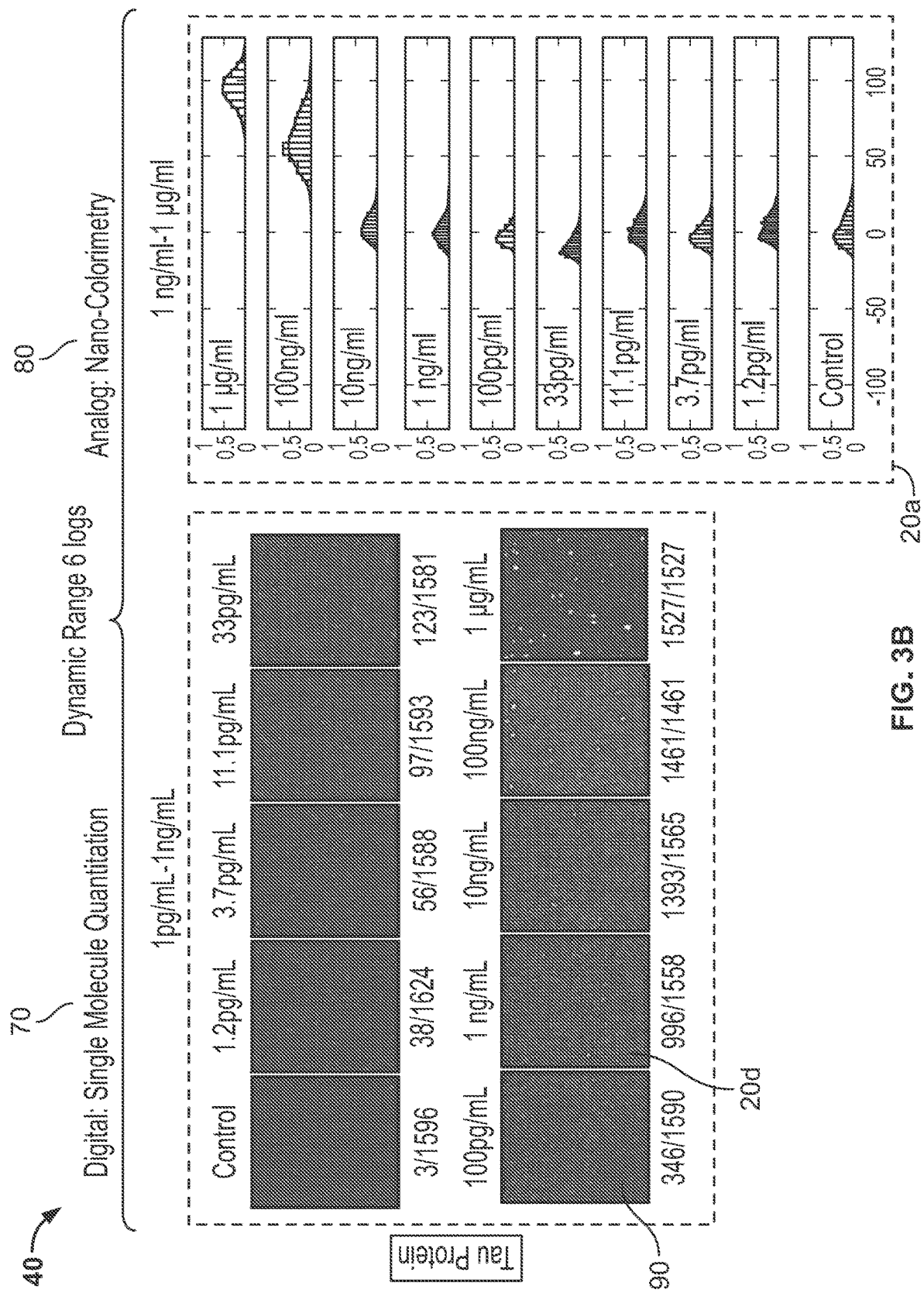

In FIG. 3B, sensor 40 includes a series of nanostructures for digital detection/quantification 70 and a series of nanostructures for analog detection/quantification 80. In particular, the series of nanostructures for digital detection 70 comprises nanostructures 20d in the form of an array. As the concentration of analyte (e.g., Tau protein) increases from 1.2 pg/mL to 10 ng/mL, the number of nanostructures that have flipped from one state another increases, as indicated by the ration under each panel 90. At analyte concentrations at or above 10 ng/mL, the series of nanostructures saturates as all or substantially all of the nanostructures (for example, at least 60%, 70%, 80%, 90%, 95% of the binding sites have bound analytes) have flipped from one state to the other. The right-hand side box illustrates the change in optical properties (e.g., colorimetric change) in a series of nanostructures 20a configured for analog detection 80. For example, as the concentration of analyte increases up to 10 ng/mL, the change in optical property (for example, color hue) of the series of nanostructures does not shift. However, as the concentration of analyte is greater than 10 ng/mL, a change in an optical property of the series of nanostructures becomes detectable, for example, as a change in color as a function of analyte concentration. Greater dynamic ranges can be achieved by including in a sensor additional series of nanostructures (for example, digital arrays and/or analog arrays) calibrated to detect and quantify analyte in other concentration ranges.

Figure 3C:
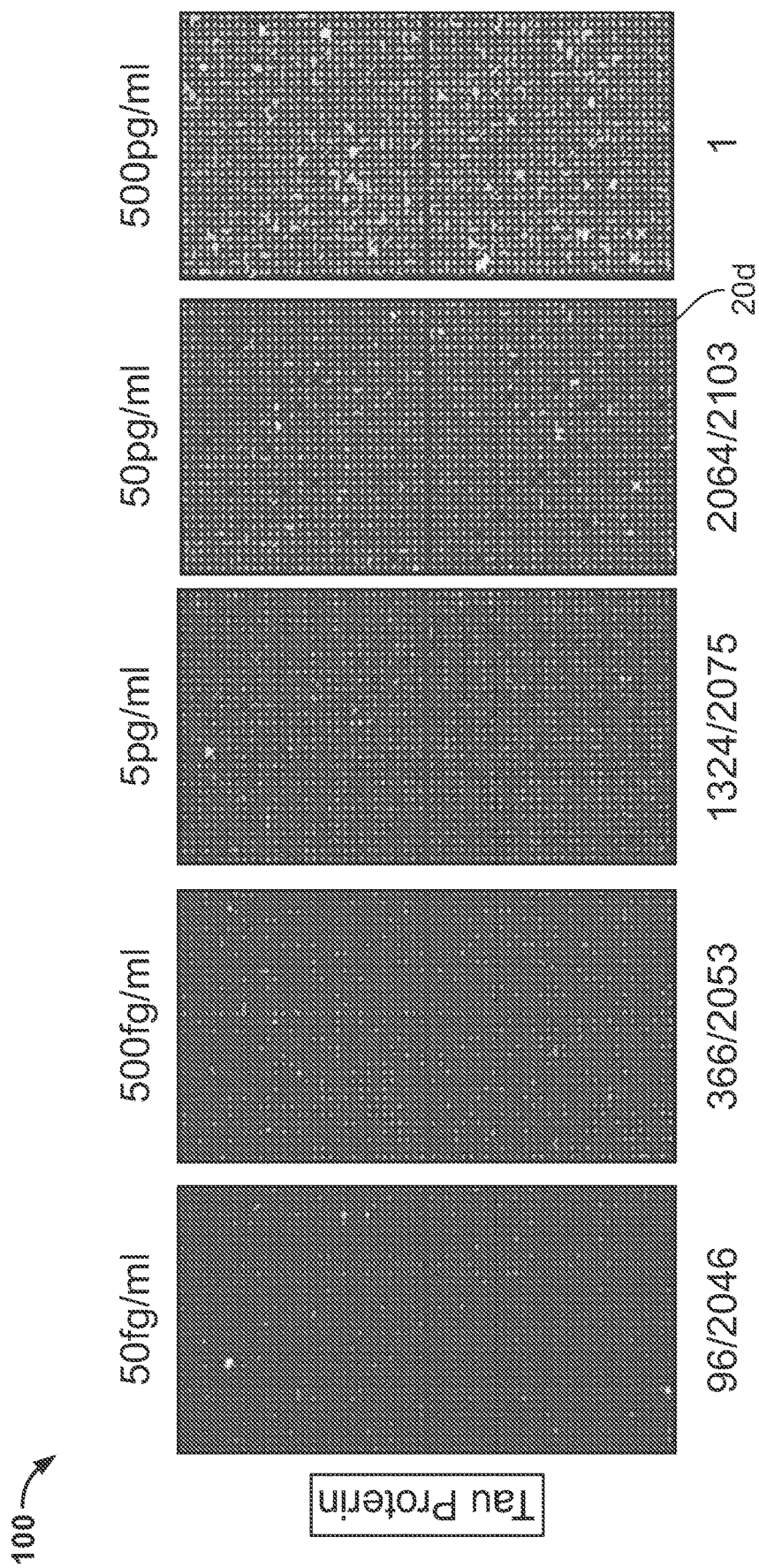

FIG. 3C illustrates digital quantification performed by a sensor 100 in accordance with an embodiment of the invention. As illustrated, the sensor is able to detect analyte molecules (molecules of Tau protein) at a concentration 50 fg/mL, with 96 out of 2046 digital nanostructures (20d) being flipped from one optical property to another that is detectable by a detector. In this particular embodiment, the sensor 100 becomes saturated at molecule concentrations at about 50 pg/mL, when all or substantially all of the nanostructures are flipped from one optical state to the other.

Figure 4:
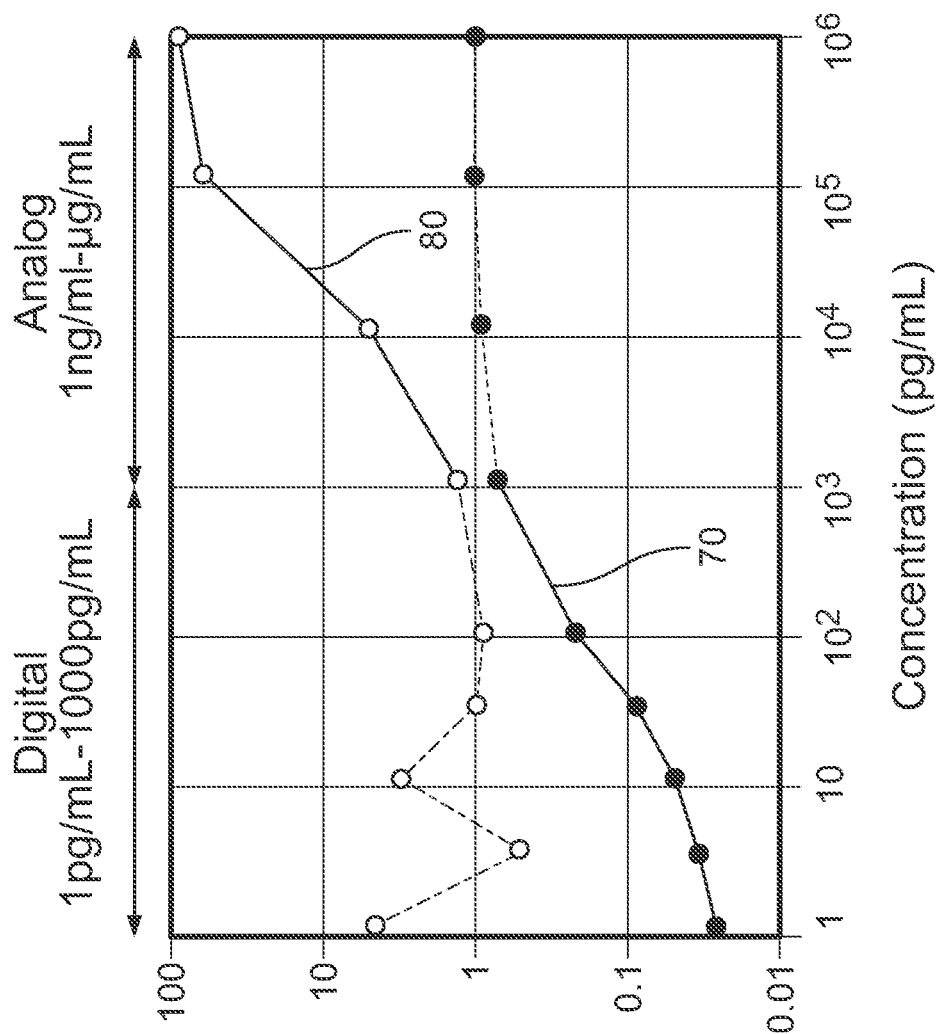
FIG. 4 is a graph showing the digital and analog measurements of exemplary data generated by a sensor exemplified in FIG. 3B.

FIG. 4 is a graph depicting data compiled from measurements obtained by the exemplary sensor 40 of FIG. 3B. In the analyte concentration range of 1 pg/mL to 1 ng/mL, the digital quantification mode 70 provides high sensitivity and a dynamic range of 3 logs. In the analyte concentration range of 1 ng/mL to 1 µg/mL, the analog colorimetric measurement 80 extends the detectable concentration range by an additional 3 logs. The transition between the digital quantification measurements and analog quantification measurements to form a continuous curve spanning the entire dynamic range can be automated using an algorithm of the type described herein. In this example, a 6 log dynamic range is achieved using a combination of a series of nanostructures configured for digital quantification with a series of nanostructures configured for analog quantification. It has been discovered that the sensors of embodiments of the invention can achieve large dynamic ranges (for example, 6 logs or more) with high sensitivity (for example, 50 fg/mL) using small volumes of sample (for example, less than 100 µL, 50 µL, 25 µL, 10 µL or 5 µL).

The nanostructure may have any suitable shape and/or size. In some cases, for example, the nanostructure may be a nanoneedle, a nanowire, a nanorod, a nanocone, or the like. Other shapes are also possible, e.g., nanoribbons, nanofilaments, nanotubes, or the like. In certain embodiments, the nanostructures are vertically aligned, although other angles or alignments are also possible. Nanostructures such as nanoneedles, nanodots, nanodisks, nanopillars, etc. have single molecule level sensitivity due to their ability to confine electromagnetic energy through coupling to surface polaritons.

The physical form of a sensor may be an array or matrix of nanostructures, for example, nanoneedles, nanowires, nanopillars, nanodots, etc., fabricated on a surface by bottom-up and/or top-down methods. The surface can be a flat surface, such as a top surface of a wafer. Alternatively, the surface may also be curved or flexible, or part of a three dimensional structure such as a fiber or a wire or the like.

The functional form of the sensor can comprise nano-optical structures, nanomechanical structures or nano-electrical structures. Accordingly, the read-out signal includes but is not limited to optical signals, electrical signals and mechanical signals. Accordingly, the concentration of the analytes may be determined by changes in optical, electrical or nanomechanical properties of the nanostructures. The optical features include, for example, surface plasmonic resonance, nanophotonic resonance, electric resonance, magnetic resonance, scattering, absorption, fluorescence, color changes, or the like. The electrical features include, for example, resistance, capacitance, current, voltage, or the like. The nanomechanical features include, for example, vibrational resonance, vibration magnitude, mechanical mass, or the like.

The foregoing structures may also be used to detect high concentration of analytes by observing changes in their optical properties, for example, surface plasmon resonances, scattering intensities, or absorptions. Sensitivity and detection ranges of these structures are closely related to the sizes of the structures. Planar fabrication technology enables scalable and flexible integration of differently sized and shaped nanostructures in one device. Embodiments of the present invention relate to using different nanostructures to achieve high sensitivity and a high dynamic range for the determination of molecules and analytes in a biological sample.

In certain embodiments, the surface properties of different structures can be designed such that the nanostructures in a first series of nanostructures may have higher binding affinities for binding the analyte than that of the second and/or third series of nanostructures. This can be achieved using binding agents having different binding affinities to a given analyte. As a result, at low concentrations, analytes are preferentially captured and detected by the single molecule nanostructures. As the concentration increases, the nanostructures of the first series saturate and signals from other series of nanostructures can be used to extend the dynamic range.

Figure 5:
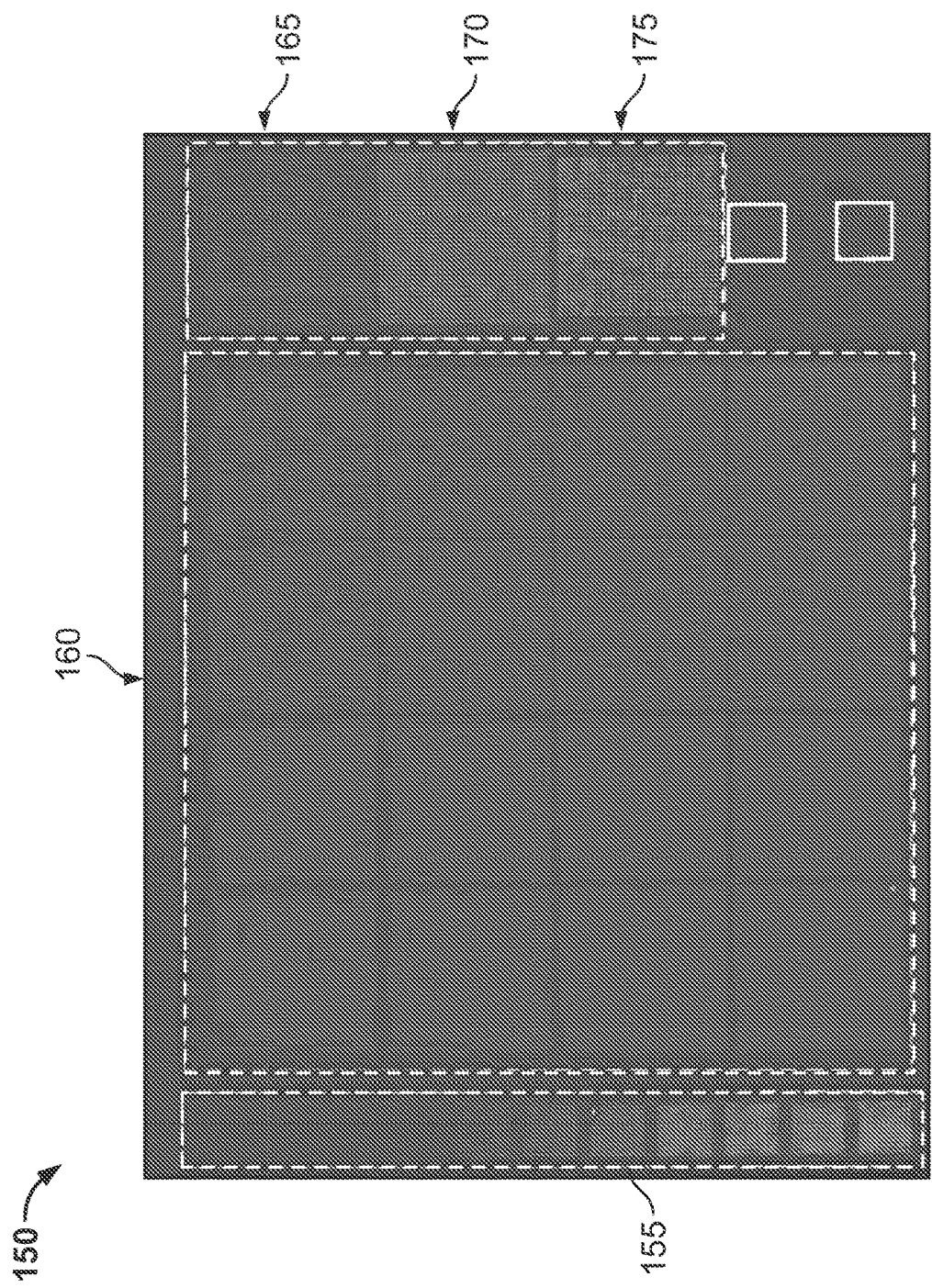
FIG. 5 is a pictorial representation of an exemplary silicon wafer-based sensor containing both a series of digital nanostructures (25,600) and three series of analog nanostructures (1,000 per series), in accordance with an embodiment of the invention.

FIG. 5 is a pictorial representation of an exemplary sensor (for example, nanomosaic chip) 150 which includes multiple series of nanostructures. In the column on the left hand side of sensor 150, the separate regions represent fabrication control structures 155 which demonstrate that the nanostructures change color as the diameter of the nanostructures is increased. The middle region 160 represents multiple separate arrays (i.e., 16 arrays) each defining a corresponding series of nanostructures (collectively comprising 25,600 nanostructures that each define single molecule nanostructures) configured for digital quantification for measuring ultra-low concentration levels of analytes. The region on the right hand side comprises three series of nanostructures (for example, a second, third, and fourth series of nanostructures) depicted as regions 165, 170, 175, for analog quantification. Each of the regions 165, 170, 175 are calibrated to measure analyte concentrations within three separate adjacent or overlapping concentration ranges. In certain embodiments, the three regions may each comprise 1,000 nanostructures.

Figure 6:
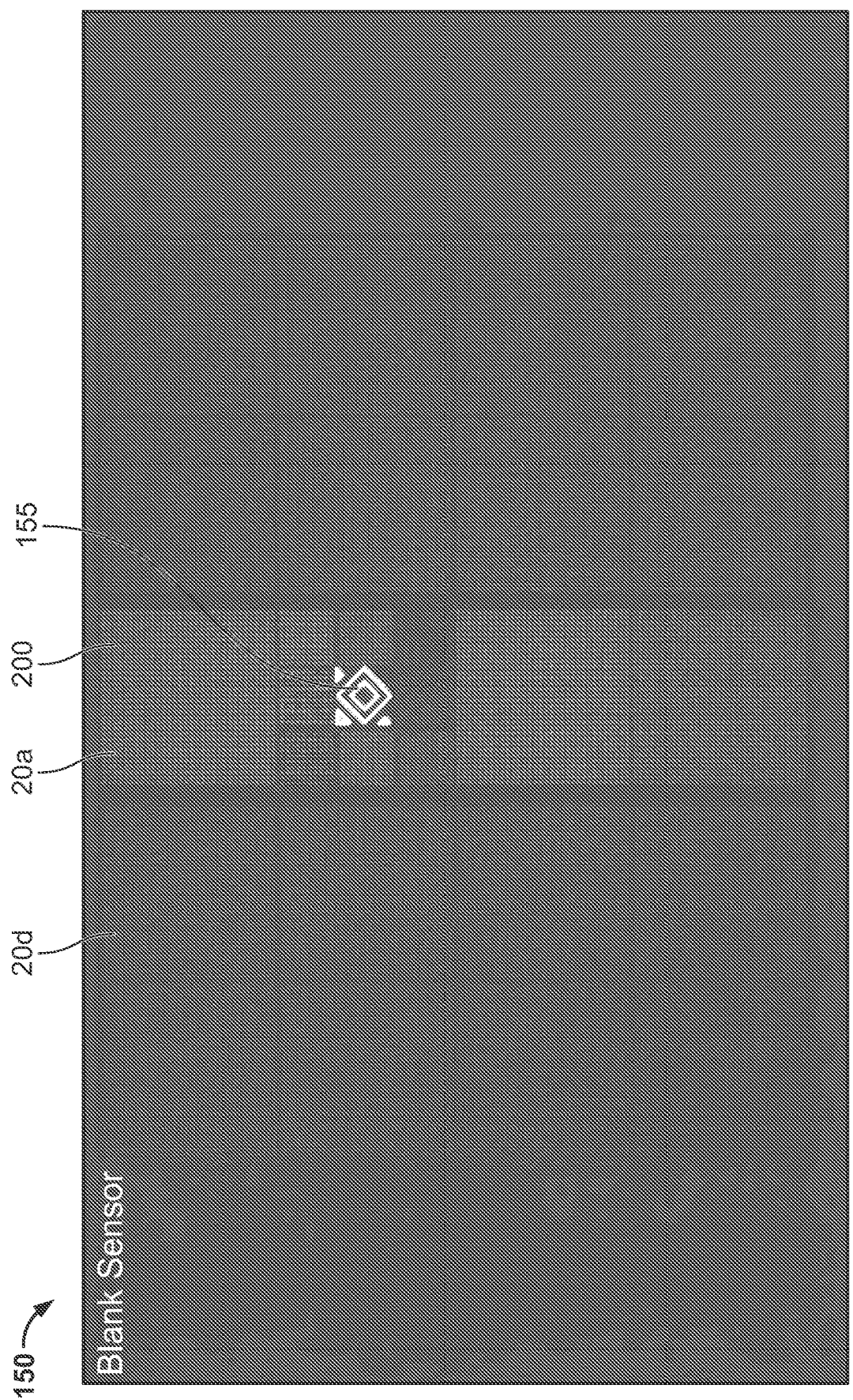
FIG. 6 is a pictorial representation of another exemplary silicon wafer-based sensor comprising a plurality of series of digital nanostructures and three series of analog nanostructures, in accordance with an embodiment of the invention.

In an alternative embodiment, as shown pictorially in FIG. 6, another exemplary sensor (for example, a nanomosaic chip) 150 comprises numerous series (regions) of nanostructures. In the center, a fiducial marker 200 is located to assist in aligning the sensor with an optical detection system. The fiducial marker can be any desired design. For example, as shown in FIG. 6, the fiducial marker 200 comprises a diamond pattern and three triangular patterns arranged in a way that does not have rotational symmetry to provide location and rotational orientation information. As a result, the fiducial marker can be used to (i) locate the sensor position, and (ii) align the horizontal and vertical planes of the nanostructures. Fabrication control structures 155 are disposed around the fiducial. Arrays of digital single molecule nanostructures 20d are disposed on the left and the right regions of the sensor, and arrays of analog molecule nanostructures 20a are disposed in the center row surrounding the fiducial and fabrication control structures. The fabrication control shown in FIG. 6 comprises 8 blocks of nanostructures (e.g., nanoneedles) whose diameters range from 80 nm to 150 nm. The color of the nanostructures (nanoneedles) under dark field imaging changes as the diameter increases.

The above represents various non-limiting examples of certain embodiments of the invention. However, other embodiments are also possible.

In certain embodiments, the nanostructure has a length, determined from an end or a point of attachment with a substrate, of less than about 500 nm, 450 nm, 350 nm, 300 nm, 250 nm, 200 nm, 150 nm, 100 nm, 50 nm, 30 nm, 20 nm, 10 nm, 5 nm, 3 nm, or 2 nm. In certain embodiments, the length of the nanostructure may be at least about 2 nm, 3 nm, 4 nm, 5 nm, 6 nm, 6 nm, 7 nm, 8 nm, 9 nm, 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, or 500 nm.

The nanostructure may have any suitable cross-sectional shape, for example, square, circular, triangular, ellipsoidal, polygonal, star, irregular shape, etc. The nanostructure may maintain the same cross-sectional shape throughout its length, or may have different cross-sectional shapes in different portions of the nanostructure. In addition, the nanostructures may have any suitable cross-sectional diameter. The cross-sectional diameter may be constant (for example, as in a nanoneedle or a nanorod), or varying (for example, as in a nanocone). The average cross-sectional diameter may be, for example, less than about 1,000 nm, 750 nm, 500 nm, 400 nm, 300 nm, 200 nm, 175 nm, 150 nm, 125 nm, 100 nm, 75 nm, 50 nm, 40 nm, 30 nm, 20 nm, or 10 nm. In certain embodiments, the cross-sectional diameter may be at least about 10 nm, 20 nm, 30 nm, 40 nm, 50 nm, 75 nm, 100 nm, 125 nm 150 nm, 175 nm, 200 nm, 300 nm, 400 nm, 500 nm, 750 nm, or 1,000 nm. Combinations are also possible in various embodiments. For example, the average diameter of the nanostructures may be between 50 nm and 300 nm, 75 nm and 250 nm, or 100 nm to 200 nm.

(B) Fabrication Considerations

The nanostructure may be formed out of any suitable material, and may be the same or different from a substrate upon which it is disposed. In certain embodiments, the nanostructures can be formed from silicon and/or other suitable semi-conductive materials (for example, germanium). Additional, non-limiting examples of materials include metals (e.g., nickel or copper), silica, glass, or the like. In certain embodiments, the nanostructure (which may be disposed on a substrate) can be formed from a unitary material.

It is contemplated that the sensors of the invention can be fabricated by a number of different approaches, for example, using semiconductor manufacturing approaches. As discussed above and in more detail below, any suitable method can be used to form the series of nanostructures useful in creating the sensors described herein. Examples include, but are not limited to, lithographic techniques such as e-beam lithography, photolithography, X-ray lithography, extreme ultraviolet lithography, ion projection lithography, etc. Alternatively or in addition, the nanostructure may be formed from one or more materials that are susceptible to etching with a suitable etchant.

For example, in certain embodiments, the nanostructures may be formed from one or more materials that are susceptible to etching with a suitable etchant. For instance, the nanostructures may comprise materials such as silica or glass, which can be etched using HF (hydrofluoric acid) or BOE (buffered oxide etch). As another example, the nanostructures may comprise a metal such as copper, iron, nickel, and/or steel, which can be etched using acids such as HCl (hydrochloric acid), $HNO_3$ (nitric acid), sulfuric acid ($H_2SO_4$), and/or other etching compounds such as such as ferric chloride ($FeCl_3$) or copper sulfate ($CuSO_4$). As yet another example, the nanostructures may comprise silicon or other semiconductor materials, which can be etched using etchants such as EDP (a solution of ethylene diamine and pyrocatechol), KOH (potassium hydroxide), and/or TMAH (tetramethylammonium hydroxide). The nanostructures may also comprise, in some cases, a plastic or a polymer, for example, polymethylmethacrylate, polystyrene, polyperfluorobutenylvinylether, etc., which can be etched using KOH (potassium hydroxide), and/or other acids such as those described herein.

(i) Nanostructure Fabrication

It is contemplated that the sensors of the invention can be fabricated by conventional semiconductor manufacturing technologies, for example, CMOS technologies, that have led to high manufacturing capacity, at high throughputs and yields in a cost-effective manner. Using such approaches it is possible to make sensors containing one of more series of nanostructures, for example, nanoneedles, nanodots, nanodisks, nanowires, and nanopillars disposed upon or integral with a substrate. Exemplary nanostructures are depicted schematically in FIGS. 7 and 8. As non-limiting examples, FIG. 7 illustrates several nanostructures 20 that can be directly formed on a substrate with current nanofabrication technologies, including electron beam lithography, photolithography, nanoimprinting, etc. For example, the nanostructure 20 can be a nanopillar, a nanodisk, a nanoneedle, or a nanodot. In addition, FIG. 8 depicts nanostructures 20 fabricated from two or more materials, for example, first and second materials 300 and 305, respectively. The compositions of each material can be used to control the binding capacity of the nanostructures for binding analyte or to achieve specific optical, electrical, or magnetic properties, as discussed below.

The fabrication of nanostructures may be performed at either at wafer scale or at chip scale with equivalent scaling capability. In this type of approach, a mask is first made for the designed nanostructure. In certain embodiments, an inverse to the design structure is used as the pattern on the mask. For example, a photoresist is coated onto the wafer or on the chip, for example, using a spin-coating or dip-coating process. The photoresist may then be exposed to electromagnetic radiation through the mask to the photoresist. Thereafter, the exposed photoresist is developed. In certain embodiments, the pattern on the photoresist can also be directly written by means of a laser beam or an electron beam. The pattern on the photoresist can then be transferred to the substrate by physical vapor deposition, including thermal evaporation, electron beam evaporation, sputter or chemical deposition, or atomic layer deposition of a desired material.

In certain embodiments, the pattern on the photoresist can be transferred to the substrate using top down etching process, including wet etching, dry etching such as reactive ion etching, sputter etching, and/or vapor phase etching. The patterning, deposition, etching, and functionalization processes can be repeated for multiple cycles. In certain embodiments, arrays of nanoneedles, nanodots, nanopillars, and/or nanowires can be fabricated using semiconductor manufacturing processes. In other embodiments, arrays of nanoneedles, nanodots, nanopillars, and/or nanowires can be fabricated using mold-stamping process.

Figures 9A, 9B, 9C, 9D:
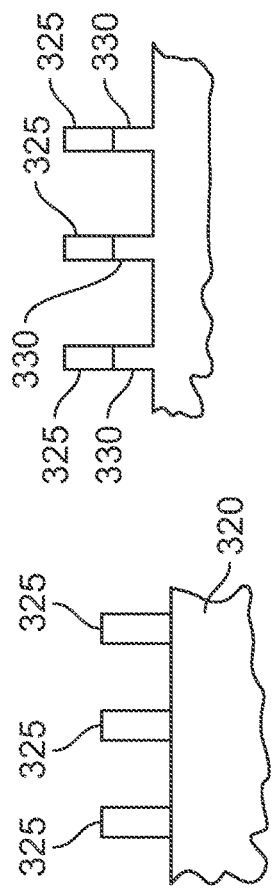
FIGS. 9A-9D are a series of cross-sectional schematic diagrams illustrating the fabrication of a series of exemplary nanostructures by photoresist patterning, development and etching processes, in accordance with an embodiment of the invention.
Figure 15B:
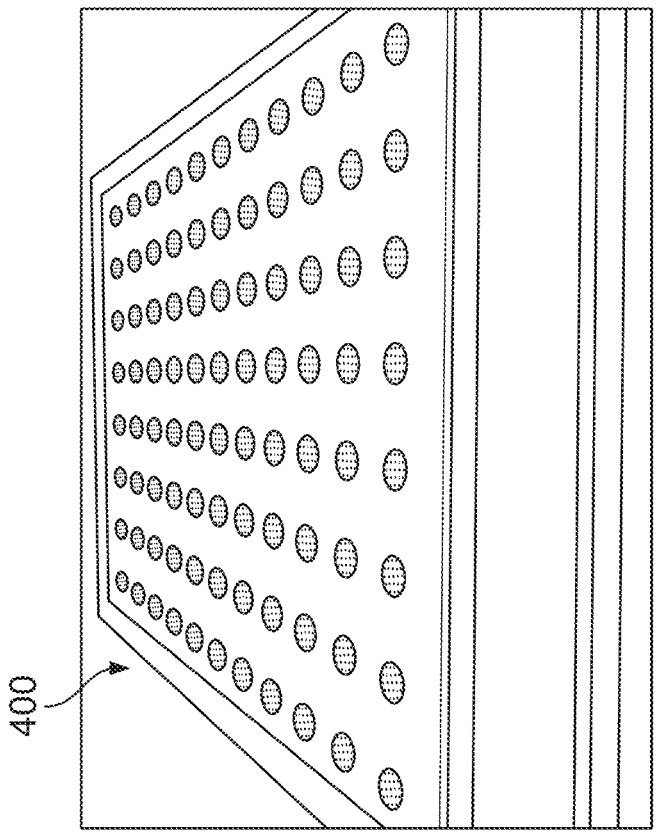
FIGS. 15A and 15B are perspective views of a nanosensor assembly (consumable) incorporating series of nanostructures in accordance with an embodiment of the invention.
Figure 15A:
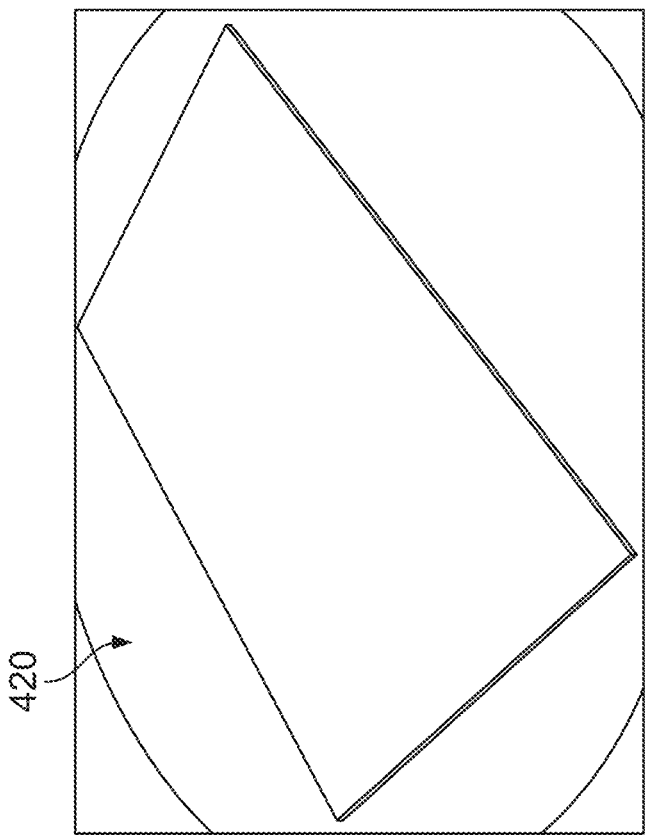
Figure 16B:
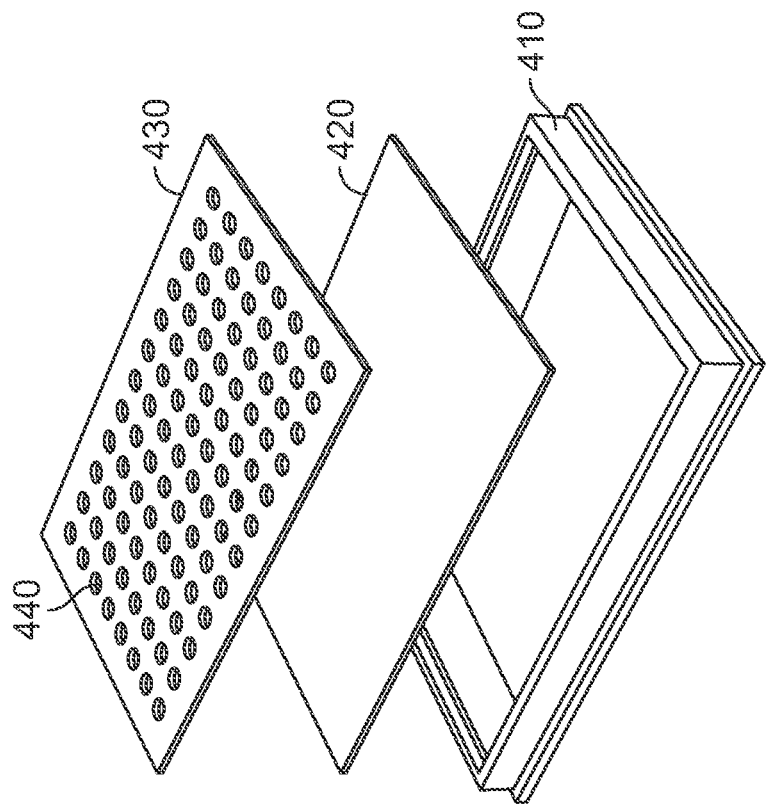
FIGS. 16A and 16B are schematic representations of a cartridge assembly comprising a wafer substrate, gasket and retaining base (FIG. 16A) and an exploded perspective view showing the components of the cartridge assembly (FIG. 16B).
Figure 16A:
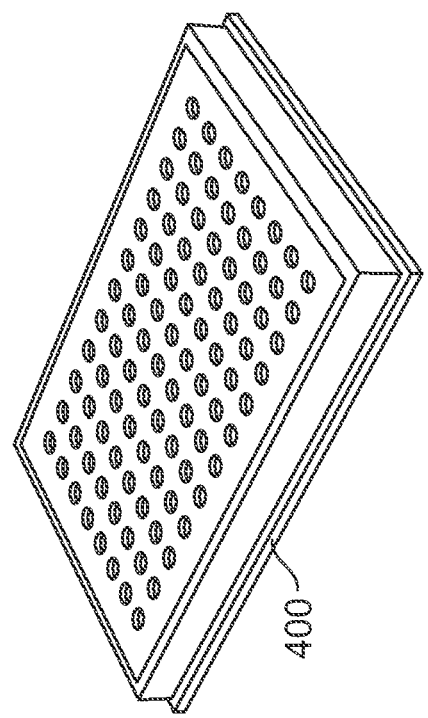

An exemplary fabrication approach is depicted in the cross-sectional views shown in FIGS. 9A-9D. Referring to FIG. 9A, more specifically, a layer of ebeam resist or photoresist 310 is coated onto a semiconductor substrate 320, such as a silicon substrate. Referring to FIG. 9B, the resist layer is then patterned by electron beam exposure or electromagnetic radiation exposure to form resist layer features 325, for example, by using an Elionix or Raith electron beam lithography system. Referring to FIG. 9C, the resist is developed in resist developer, to remove portions thereof and leaving only the resist features 325. Referring to FIG. 9D, an etching process is then performed with the patterned resist serving as a mask. The etching process may be, e.g., a wet or a dry etch. A suitable wet etch can be, for example, a solution of ethylenediamine pyrocatechol (EDP), potassium hydroxide (KOH), or tetramethylammonium hydroxide (TMAH). As a result, silicon nanoneedles 330 are created with resist 325 disposed upon the top surface of the nanoneedles. The height of the nanoneedles can range from 2 nm to 1000 nm. The diameter of the nanoneedles can range from 10 nm to 1000 nm. Resist features 325 may be removed using a conventional wet etching buffer (not shown).

The surface of the etched structure can be chemically activated using chemical vapor deposition or atomic layer deposition or a hybrid of both. This activation process can also be performed in a wet solution. The chemically activated structure is then ready to bind a biological material, a binding agent described herein via, for example, chemisorption (e.g., covalent binding) or physisorption.

A suitable silicon substrate can be, for example, a round 12" silicon wafer. In order to comply with Society of Biomolecular Screening (SBS) recommended microplate specifications, the round wafer is diced into a rectangular shape. The dicing step can be performed at the end of the fabrication process as described above. Alternatively, dicing into half of the depth of the wafer can be performed in the beginning of the fabrication process; then, after completion of all fabrication steps (including spin coating, patterning, deposition and etching), the wafers can be easily cleaved into the SBS format.

Another fabrication approach is depicted in the cross-sectional views shown in FIGS. 10A-10G. Referring to FIG. 10A, a silicon dioxide layer 335 is formed on a top surface of a silicon substrate 320 using chemical vapor deposition, atomic layer deposition or a combination of both. The thickness of the layer can range from 2 nm to 100 nm. A resist layer 310 comprising, for example, polymethyl methacrylate, is spun coated onto the silicon dioxide layer 335. Referring to FIGS. 10B and 10C, the resist layer 310 is patterned by an electron beam or electromagnetic radiation, and then developed in resist developer to form resist features 325. Referring to FIG. 10D, an aluminum layer 340 is deposited over the patterned resist layer features 325 by, e.g., thermal evaporation (or electron evaporation) with, for example, a Sharon thermal evaporator or Denton e-beam evaporator. The aluminum layer 340 is preferably 20 nm to 100 nm thick. Referring to FIG. 10E, a lift-off process is performed to remove the resist layer features 325, leaving behind an aluminum mask over the silicon dioxide layer 335. Referring to FIG. 10F, an etching process, such as a reactive ion etch with an STS ICP RIE system or an Oxford plasma RIE system is performed to etch silicon oxide nanoneedles 335. The RIE etching can further proceed into the silicon layer 320, resulting in a two layer SiO2-Si nanostructures. Referring to FIG. 10G, the aluminum mask 340 may be etched off the tops of silicon nanoneedles 342 in an aluminum etchant buffer, e.g., a mixtures of 1-5% $HNO_3$, $H_3PO_4$ and $CH_3COOH$.

Yet another fabrication approach is depicted in the cross-sectional views shown in FIGS. 11A-11F. Referring to FIG. 11A, a silicon dioxide layer 335 is grown on a top surface of a silicon substrate 320. A resist layer 310 is spun coated onto the silicon dioxide layer 335. Referring to FIGS. 11B and 11C, the resist layer 310 is patterned by electron beam or electromagnetic radiation, and then developed in resist developer to form resist features 325. Referring to FIG. 11D, a metal layer, such as an aluminum layer 340, is deposited over the patterned resist layer 310 by, for example, a thermal evaporation (or electron evaporation) process. Referring to FIG. 11E, a lift-off process is then performed to remove the resist layer 310, leaving behind aluminum nanoneedles disposed upon the oxide layer on the substrate. Referring to FIG. 11F, a coating layer 345 can be spun coated to modify the surface properties of the substrate. The coating layer can be a hydrophobic material, such as TEFLON, or a layer of polyethylene glycol molecules. The thickness of the coating layer is smaller than the height of the aluminum nanoneedles.

Another fabrication approach is depicted in the cross-sectional views shown in FIGS. 12A-12F. Referring to FIG. 12A, a resist layer 310 is spun coated on an oxide substrate 350. The oxide layer can be a thermally grown silicon oxide, or formed by chemical vapor deposition. In some embodiments, the substrate 350 may be a glass slide. Referring to FIGS. 12B and 12C, electromagnetic radiation can be used to pattern features in the resist layer 310, which is then developed in resist developer to form resist features 325. Referring to FIG. 12D, a silicon layer 355 is deposited over the patterned resist layer 310 by, for example, using chemical vapor deposition. Referring to FIG. 12E, a lift-off process is performed to remove the patterned resist layer 310, which results in a silicon nanodot 360 structure on the oxide substrate. Referring to FIG. 12F, silicon nanoneedle structures 365 may be epitaxially grown using the silicon nanodots 360 as seeds, by, e.g., VLS (vapor-liquid-solid) method.

Another fabrication approach is depicted in the cross-sectional views shown in FIGS. 13A-13D, in which a photoresist layer may be patterned by using a mold. Referring to FIG. 13A, a mold 370 is made from e.g., Si or quartz. The mold can be made by high resolution patterning technology, such as ebeam lithography. The mold has feature sizes similar to that of the target nanostructures to be replicated. Referring to FIG. 13B, a resist layer 310 is spun coated on silicon substrate 320. Referring to FIG. 13C, the features in mold 370 are then stamped into the resist by nanoimprinting or nanostamping, and then crosslinked by e.g., UV or heat. Referring to FIG. 13D, the imprinted photoresist can be used as the mask for the subsequent etching process to obtain the silicon nanostructures.

With reference to FIGS. 14A and 14B, by replicating the fabrication steps described hereinabove it is possible to produce a plurality of sensors 375 fabricated on a wafer 320, to create, for example, a 10×10 array of sensors disposed on each wafer 320. As shown in FIG. 14B, each sensor comprises an array of nanostructures, for example, nanoneedles 330 disposed upon a silicon substrate.

It should be noted that the nanostructures depicted in FIGS. 10-14 have at least one dimension in the range of 1-999 nm, 1-750 nm, 1-500 nm, 1-400 nm, 1-300 nm, 1-200 nm, 1-100 nm, 10-999 nm, 10-750 nm, 10-500 nm, 10-400 nm, 10-300 nm, 10-200 nm, 10-100 nm, 20-999 nm, 20-750 nm, 20-500 nm, 20-400 nm, 20-300 nm, 20-200 nm, 20-100 nm, 30-999 nm, 30-750 nm, 30-500 nm, 30-400 nm, 30-300 nm, 30-200 nm, 30-100 nm, 40-999 nm, 40-750 nm, 40-500 nm, 40-400 nm, 40-300 nm, 40-200 nm, 40-100 nm, 50-999 nm, 50-750 nm, 50-500 nm, 50-400 nm, 50-300 nm, 50-200 nm, or 50-100 nm. The pitch, i.e., center-to-center distance, between nanostructures, for example in FIG. 14B, is typically 1-100 µm, for example, at least 1.5 µm, 2 µm, 3 µm, 4 µm, 5 µm, 6 µm, 7 µm, 8 µm, 9 µm, 10 µm, 20 µm, 30 µm, 40 µm, 50 µm, 60 µm, 70 µm, 80 µm, or 90 µm. Other dimensions may be used for the pitches of the structures. The array of nanostructures in FIG. 14B, in its entirety, can also be arranged in an array format, as shown in FIG. 14A. For example, the pitch in between two arrays of nanostructures, shown in FIG. 14A may range from less than 100 µm to larger than a few centimeters. Furthermore, it is contemplated that the pitch and size of the nanostructures may be different in different parts of the chip, or within each series of nanostructures. Combinations of any of these are also possible in various embodiments.

Furthermore, the distance or pitch between nanostructures in a periodic structure may be controlled, for example, such that the nanostructures form a meta-surface. For example, the pitch may be set to be less than the wavelength of the incident light. For instance, the pitch may be less than 700 nm, 600 nm, 500 nm, 400 nm, 300 nm, 200 nm, 100 nm, 50 nm, 25 nm, 10 nm, 9 nm, 8 nm, 7 nm, 6 nm, 5 nm, 4 nm 3 nm or 2 nm, and/or greater than 1 nm, 2 nm, 3 nm, 4 nm, 5 nm, 6 nm, 7 nm, 8 nm, 9 nm 10 nm, 25 nm, 50 nm, 100 nm 200 nm, 300 nm, 400 nm, 500 nm, 600 nm or 700 nm. For example, under certain circumstances, the pitch may be between 400 nm and 500 nm. The nanostructures may have any of the dimensions provided herein. Under certain circumstances, the average cross-sectional diameter or minimum or maximum cross-sectional dimension of the nanostructure is less than the wavelength of the incident light. Under certain circumstances, the individual nanostructures are configured to be optically resolvable, where, for example, the pitch may be less than 100 µm, less than 10 µm, less than 5 µm, and/or greater than 1 µm, or greater than 5 µm.

Table 1 describes exemplary parameters of the nanostructures described herein for optical read-outs.

TABLE 1

| Parameter | Minimum Value | Typical Value or Range | Maximum Value | Units |
|---|---|---|---|---|
| Digital nanostructure cross-sectional dimension or diameter | 10 | 60-95 | 150 | nm |
| Analog nanostructure cross-sectional dimension or diameter | 100 | Depends on analyte concentration (e.g., can be 110-130) | 1,000 | nm |
| Center-center spacing of adjacent nanostructures | 1 | 1.5-3 | Depends on substrate size | µm |
| Height of the nanostructure | 50 | 100-250 | 1,000 | nm |

Table 2 describes exemplary parameters of the nanostructures described herein for a mechanical read-out.

TABLE 2

| Parameter | Minimum Value | Typical Value or Range | Maximum Value | Units |
|---|---|---|---|---|
| Digital nanostructure cross-sectional dimension or diameter | 0.1 | 60-95 | 100 | nm |
| Analog nanostructure cross-sectional dimension or diameter | 100 | Depends on analyte concentration | 100,000 | nm |
| Center-center spacing of adjacent nanostructures | 10 | 10-100 | Depends on substrate size | µm |
| Height of the nanostructure | 50 | 100-1,000 | 10,000 | nm |

Table 3 describes exemplary parameters of the nanostructures described herein for an electrical read-out.

TABLE 3

| Parameter | Minimum Value | Typical Value or Range | Maximum Value | Units |
|---|---|---|---|---|
| Digital nanostructure cross-sectional dimension or diameter | 5 | 10-100 | 500 | nm |
| Analog nanostructure cross-sectional dimension or diameter | 100 | Depends on analyte concentration | 1000 | nm |
| Center-center spacing of adjacent nanostructures | 10 | 100-1,000 | Depends on substrate size | µm |

TABLE 3-continued

| Parameter | Minimum Value | Typical Value or Range | Maximum Value | Units |
|---|---|---|---|---|
| Height of the nanostructure | 10 | 100-500 | 10,000 | nm |

(ii) Nanostructure Functionalization

The nanostructures in the first series and, where applicable, the second and third series, are functionalized with a binding agent that binds the analyte, for example, binding agent, for example, a biological binding agent, that binds the analyte. The biological binding agent can be, for example, an antibody, an aptamer, a member of a ligand-receptor pair, an enzyme, or a nucleic acid. Under certain circumstances, for example, when the first series is used to measure very low concentrations of analyte, it may be advantageous to use a binding agent in the first series that has a higher binding affinity for the analyte than the binding agent in a second, third or subsequent series.

The number of binding agents applied to a given nanostructure may vary depending upon the desired assay, for example, the required dynamic range, number of analytes to be detected, etc. For example, under certain circumstances, a nanostructure may be functionalized with 1, 5, 10, 20, 25, 50, 75, 100 or more binding agents. These values may range from 1-1,000, 1-500, 1-250, 1-100, 1-50, 1-25, 1-10 or 1-5 binding agents per nanostructures.

The sensor may be designed to detect and/or quantify any analyte of interest in a sample. Furthermore, a nanostructure or series of nanostructures in a given sensor may be configured to bind, detect and/or quantify plurality of different analytes simultaneously or sequentially. For example, the sensor can comprise a plurality of different binding agents for detecting a corresponding plurality of different analytes in the test sample.

Analytes may be detected and/or quantified in a variety of samples. The sample can be in any form that allows for measurement of the analyte. In other words, the sample must be permit analyte extraction or processing to permit detection of the analyte, such as preparation of thin sections. Accordingly, the sample can be fresh, preserved through suitable cryogenic techniques, or preserved through non-cryogenic techniques. In certain embodiments, the sample is a body fluid sample, such as a blood, serum, plasma, urine, cerebrospinal fluid, or interstitial fluid sample. In certain embodiments, the sample is a tissue extract obtained, for example, from a biopsy sample obtained by using conventional biopsy instruments and procedures. Endoscopic biopsy, excisional biopsy, incisional biopsy, fine needle biopsy, punch biopsy, shave biopsy and skin biopsy are examples of recognized medical procedures that can be used by one of skill in the art to obtain tissue samples. Suitable techniques for tissue preparation for subsequent analysis are well-known to those of skill in the art. In certain embodiments, the sample is a cell sample or a cell supernatant sample.

Analytes include biological molecules, for example, a protein, peptide, carbohydrate, glycoprotein, glycopeptide, lipid, lipoprotein, nucleic acid, or nucleoprotein. Exemplary analytes include, for example, cells, antibodies, antigens, virus particles, pathogenic bacteria, ions, spores, yeasts, molds, cellular metabolites, enzymes, enzyme inhibitors, receptor ligands, peptides, proteins, fatty acids, steroids, hormones, enzymes, and nucleic acids. Other non-biological analytes that can be detected can include, for example, organic compounds, synthetic molecules, metals, metal complexes, drugs, nerve agents, and narcotic agents.

In certain embodiments, the analyte is a cytokine, for example, an interferon (for example, IFNα, IFNβ, and IFNγ), interleukin (for example, IL-1, IL-2, IL-3, IL-4, IL-5, IL-6, IL-7, IL-8, IL-9, IL-10, IL-12, IL-17 and IL-20), tumor necrosis factors (for example, TNFα and TNFβ), erythropoietin (EPO), FLT-3 ligand, gIp10, TCA-3, MCP-1, MIF, MIP-1α, MIP-1β, Rantes, macrophage colony stimulating factor (M-CSF), granulocyte colony stimulating factor (G-CSF), and granulocyte-macrophage colony stimulating factor (GM-CSF), as well as functional fragments of any of the foregoing.

In certain embodiments the analyte is a hormone. Examples of hormones include, but are not limited to, epinephrine, melatonin, norepinephrine, triiodothyronine, thyroxine, dopamine, prostaglandins, leukotrienes, prostacyclin, thromboxane, amylin (or islet amyloid polypeptide), anti-mullerian hormone (or mullerian inhibiting factor or hormone), adiponectin, adrenocorticotropic hormone (or corticotropin), angiotensinogen and angiotensin, antidiuretic hormone (or vasopressin, arginine vasopressin), atrial-natriuretic peptide (or atriopeptin), brain natriuretic peptide, calcitonin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin-like growth factor (or somatomedin), leptin, lipotropin, luteinizing hormone, melanocyte stimulating hormone, motilin, orexin, osteocalcin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone (or thyrotropin), thyrotropin-releasing hormone, vasoactive intestinal peptide, guanylin, uroguanylin, testosterone, dehydroepiandrosterone, androstenedione, dihydrotestosterone, aldosterone, estradiol, estrone, estriol, cortisol, progesterone, calcitriol (1,25-dihydroxyvitamin D3), and calcidiol (25-hydroxyvitamin D3).

The nanostructures can be functionalized using standard chemistries known in the art. As an initial matter, the surfaces of the nanostructures may be activated for binding a binding agent using standard chemistries, including standard linker chemistries.

The binding agent may contain or be engineered to contain a functional group capable of reacting with the surface of the nanostructure (for example, via silanol groups present on or at the surface of the nanostructure), either directly or via a chemical linker.

In one approach, the surface silanol groups of the nanostructure may be activated with one or more activating agents, such as an alkoxy silane, a chlorosilane, or an alternative silane modality, having a reactive group (e.g., a primary amine). Exemplary alkoxy silanes having a reactive group may include, for example, an aminosilane (e.g., (3-aminopropyl)-trimethoxysilane (APTMS), (3-aminopropyl)-triethoxysilane (APTES), (3-aminopropyl)-diethoxy-methylsilane (APDEMS), 3-(2-aminoethyaminopropyl) trimethoxysilane (AEAPTM)), a glycidoxysilane (e.g., (3-glycidoxypropyl)-dimethyl-ethoxysilane (GPMES)), or a mercaptosilane (e.g., (3-mercaptopropyl)-trimethoxysilane (MPTMS) or (3-mercaptopropyl)-methyl-dimethoxysilane (MPDMS). Exemplary chlorosilanes having a reactive group include 3-(trichlorosilyl)propyl methacrylate (TPM) and 10-isocyanatodecyltrichlorosilane.

Thereafter, a functional group on the binding agent, for example, a primary amine on the side chain on a lysine residue can be attached to the reactive group added to the surface of the nanostructure using a variety of cross-linking agents. Exemplary cross-linking agents can include, for example, homobifunctional cross-linking agents (e.g., glutaraldehyde, bismaleimidohexane, bis(2-[Succinimidooxycarbonyloxy]ethyl) sulfone (BSOCOES), [bis(sulfosuccinimidyl)suberate] (BS3), (1,4-di-(3'-[2pyridyldithiol-propionamido)butane) (DPDPB), disuccinimidyl suberate (DSS), disuccinimidyl tartrate (DST), sulfodisuccinimidyl tartrate (Sulfo DST), dithiobis(succinimidyl propionate (DSP), 3,3'-dithiobis(sulfosuccinimidyl propionate (DTSSP), ethylene glycol bis(succinimidyl succinate) (EGS), bis(β[4-azidosalicylamido]-ethyl)disulfide iodinatable (BASED), homobifunctional NHS crosslinking reagents (e.g., bis N-succinimidyl-[pentaethylene gylcol] ester (Bis(NHS)PEO-5), and homobifunctional isothiocyanate derivatives of PEG or dextran polymers) and heterobifunctional cross-linking agents (e.g., succinimidyl 4-(N maleimidomethyl) cyclohexane-1-carboxylate (SMCC), succinimidyl-4-(N maleimidomethyl)-cyclohexane-1-carboxy(6-amidocaproate) (LC-SMCC), N maleimidobenzoyl-N-hydroxysuccinimide ester (MBS), succinimide 4-(p-maleimidophenyl) butyrate (SMPB), N-hydroxy-succinimide and N-ethyl-'(dimethylaminopropyl)carbodiimide (NHS/EDC), (N-E-maleimido-caproic acid)hydrazide (sulfoEMCS), N-succinimidyl-S-acetylthioacetate (SATA), monofluoro cyclooctyne (MFCO), bicyclo[6.1.0]nonyne (BCN), N-succinimidyl-S-acetylthiopropionate (SATP), maleimido and dibenzocyclooctyne ester (a DBCO ester), and 1-ethyl-3-[3-dimethylaminopropyl]carbodiimide hydrochloride (EDC)).

By way of example, the nanostructures described herein, may be activated via an alkoxy silane (for example, APTMS) to modify the free hydroxyl groups of the surface silanol groups to create a reactive group (for example, primary amines). The reactive group (for example, primary amines) created on the nanostructure then may be reacted with a cross-linking agent, for example, glutaraldehyde, that forms a covalent linkage with the free amine group present, for example, in the side chain of a lysine amino acid in a protein, for example, an antibody of interest.

It is contemplated that other activation and conjugation chemistries known in the art can be used to covalently couple one or more binding agents to the surface of the nanostructures described herein.

It is contemplated that a given nanostructure or series of nanostructures may be functionalized with a binding agent that binds an analyte of interest. The term "binding agent" as used herein refers to an agent that binds specifically to an analyte of interest. The terms "bind preferentially," or "binds specifically" as used in connection with a binding agent refers to an agent that binds and/or associates (i) more stably, (ii) more rapidly, (iii) with stronger affinity, (iv) with greater duration, or (v) a combination of any two or more of (i)-(iv), with a particular target analyte than it does with a molecule other than the target analyte. For example, a binding agent that specifically or preferentially binds a target analyte is a binding domain that binds a target analyte, e.g., with stronger affinity, avidity, more readily, and/or with greater duration than it binds a different analyte. The binding agent may be an affinity for the analyte of about 100 nM, 50 nM, 20 nM, 15 nM, 10 nM, 9 nM, 8 nM, 7 nM, 6 nM, 5 nM, 4 nM, 3 nM, 2 nM, 1 nM, 0.5 nM, 0.1 nM, or 0.01 nM, or stronger, as determined by surface plasmon resonance. For example, the binding agent may have an affinity for the analyte within the range from about 0.01 nM to about 100 nM, from about 0.1 nM to about 100 nM, or from about 1 nM to about 100 nM. It is understood that a binding agent that binds preferentially to a first target analyte may or may not preferentially bind to a second target analyte. As such, "preferential binding" does not necessarily require (although it can include) exclusive binding.

Exemplary binding agents include enzymes (for example, that bind substrates and inhibitors), antibodies (for example, that bind antigens), antigens (for example, that bind target antibodies), receptors (for example, that bind ligands), ligands (for example, that bind receptors), nucleic acid single-strand polymers (for example, that bind nucleic acid molecules to form, for example, DNA-DNA, RNA-RNA, or DNA-RNA double strands), and synthetic molecules that bind with target analytes. Natural, synthetic, semi-synthetic, and genetically-altered macromolecules may be employed as binding agents. Binding agents include biological binding agents, for example, an antibody, an aptamer, a receptor, an enzyme, or a nucleic acid.

As used herein, unless otherwise indicated, the term "antibody" is understood to mean an intact antibody (e.g., an intact monoclonal antibody) or antigen-binding fragment of an antibody (for example, an antigen-binding fragment of a monoclonal antibody), including an intact antibody or antigen-binding fragment that has been modified, engineered, or chemically conjugated. Examples of antibodies that have been modified or engineered include chimeric antibodies, humanized antibodies, and multispecific antibodies (e.g., bispecific antibodies). Examples of antigen-binding fragments include Fab, Fab', (Fab')$_2$, Fv, single chain antibodies (e.g., scFv), minibodies, and diabodies.

In certain embodiments, an antibody binds to its target with a $K_D$ of about 300 pM, 250 pM, 200 pM, 190 pM, 180 pM, 170 pM, 160 pM, 150 pM, 140 pM, 130 pM, 120 pM, 110 pM, 100 pM, 90 pM, 80 pM, 70 pM, 60 pM, 50 pM, 40 pM, 30 pM, 20 pM, or 10 pM, or lower. An antibody may have a human IgG1, IgG2, IgG3, IgG4, or IgE isotype.

Methods for producing antibodies as well as other protein binding agents are known in the art. For example, the protein binding agents may be purified from natural sources or produced using recombinant DNA technologies. For example, DNA molecules encoding, for example, a protein binding agent can be synthesized chemically or by recombinant DNA methodologies. The resulting nucleic acids encoding desired protein-based binding agents can be incorporated (ligated) into expression vectors, which can be introduced into host cells through conventional transfection or transformation techniques. The transformed host cells can be grown under conditions that permit the host cells to express the genes that encode the proteins of interest. Specific expression and purification conditions will vary depending upon the expression system employed. For example, if a gene is to be expressed in E. coli, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art. If the engineered gene is to be expressed in eukaryotic host cells, e.g., CHO cells, it is first inserted into an expression vector containing a suitable eukaryotic promoter, a secretion signal, a poly A sequence, and a stop codon. The gene construct can be introduced into eukaryotic host cells using conventional techniques. Thereafter, the host cells are cultured under conditions that permit expression of the protein based binding agent. Following expression, the polypeptide can be harvested and purified or isolated using techniques known in the art including, for example, affinity tags such as glutathione-S-transferase (GST) or histidine tags.

Exemplary nucleic acid based binding agents include aptamers and spiegelmers. Aptamers are nucleic acid-based sequences that have strong binding activity for a specific target molecule. Spiegelmers are similar to aptamers with regard to binding affinities and functionality but have a structure that prevents enzymatic degradation, which is achieved by using nuclease resistant L-oligonucleotides rather than naturally occurring, nuclease sensitive D-oligonucleotides.

Aptamers are specific nucleic acid sequences that bind to target molecules with high affinity and specificity and are identified by a method commonly known as Selective Evolution of Ligands by Evolution (SELEX), as described, for example, in U.S. Pat. Nos. 5,475,096 and 5,270,163. Each SELEX-identified nucleic acid ligand is a specific ligand of a given target compound or molecule. The SELEX process is based on the observation that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand enriched mixture of nucleic acids, then reiterating the steps of binding, partitioning, dissociating and amplifying through as many cycles as desired to yield highly specific high affinity nucleic acid ligands to the target molecule. Thus, this method allows for the screening of large random pools of nucleic acid molecules for a particular functionality, such as binding to a given target molecule.

The SELEX method also encompasses the identification of high-affinity nucleic acid ligands containing modified nucleotides conferring improved characteristics on the ligand, such as improved in vivo stability and protease resistance. Examples of such modifications include chemical substitutions at the ribose and/or phosphate and/or base positions. SELEX process-identified nucleic acid ligands containing modified nucleotides are described in U.S. Pat. Nos. 5,660,985 and 5,580,737, which include highly specific nucleic acid ligands containing one or more nucleotides modified at the 2' position with, for example, a 2'-amino, 2'-fluoro, and/or 2'-O-methyl moiety.

Instead of using aptamers, which may require additional modifications to become more resistant to nuclease activity, it is contemplated that spiegelmers, mirror image aptamers composed of L-ribose or L-2'deoxyribose units (see, U.S. Pat. Nos. 8,841,431, 8,691,784, 8,367,629, 8,193,159 and 8,314,223) can be used in the practice of the invention. The chiral inversion in spiegelmers results in an improved plasma stability compared with natural D-oligonucleotide aptamers. L-nucleic acids are enantiomers of naturally occurring D-nucleic acids that are not very stable in aqueous solutions and in biological samples due to the widespread presence of nucleases. Naturally occurring nucleases, particularly nucleases from animal cells are not capable of degrading L-nucleic acids.

Using in vitro selection, an oligonucleotide that binds to the synthetic enantiomer of a target molecule, e.g., a D-peptide, can be selected. The resulting aptamer is then resynthesized in the L-configuration to create a spiegelmer (from the German "spiegel" for mirror) that binds the physiological target with the same affinity and specificity as the original aptamer to the mirror-image target. This approach has been used to synthesize spiegelmers that bind, for example, hepcidin (see, U.S. Pat. No. 8,841,431), MCP-1 (see, U.S. Pat. Nos. 8,691,784, 8,367,629 and 8,193,159) and SDF-1 (see, U.S. Pat. No. 8,314,223).

(III) Cartridge

The sensors described herein, once fabricated, can be included in, or otherwise assembled into, a cartridge for use within a detection system. The invention also provides a cartridge for detecting the presence, or quantifying the amount, of an analyte in a sample of interest. The cartridge comprises a housing defining at least one well comprising any one or more of the foregoing sensors. The housing may define a plurality of wells, each well comprising any one or more of the foregoing sensors. The wells can be defined by (for example, integral with) the substrate or can be defined by a hole formed in a gasket disposed upon the substrate.

Referring to FIGS. 15A, 15B, 16A and 16B, the sensors described herein may be incorporated into a cartridge assembly (a consumable assembly) 400. The cartridge assembly may include a housing or base 410, a wafer substrate 420 upon which the series of nanostructures are disposed, and gasket 430. The gasket 430, when placed over wafer substrate 420, can define wells, wherein the base of each well can comprise one or more sensors. The wafer substrate interfits into housing or base 410, which is configured to hold the substrate and to be easily insertable into a detection system. The housing or base may be made from a variety of different materials, for example, a metal such as aluminum, as well as plastic or rubber. The housing or base may have a feature, such as an angled corner, to facilitate placement thereof into the sensor system and/or to confirm orientation.

Gasket 430 can be fabricated, for example, from silicone or plastic, sized and shaped to be placed over the wafer substrate, with openings 440 dimensioned to create wells with the wafer substrate containing the sensors disposed upon or within the wafer substrate. The openings 440 that define the wells may be dimensioned to contain at least a portion of the sample, for example, 2, 3, 4, 5, 6, 7, 8, 9, 10, 20, or 50 μL, to be analyzed. Typically, a well includes walls defined by the gasket 430 and a bottom portion defined by the wafer substrate 420, with a sensor being disposed on the substrate in the well. A diameter of the well may range from 600 μm to 90 mm (for example, from 1 mm to 80 mm,) and may have a thickness of 1 mm. In some embodiments, the wells may be formed integrally with the substrate during the fabrication process.

Figure 17:
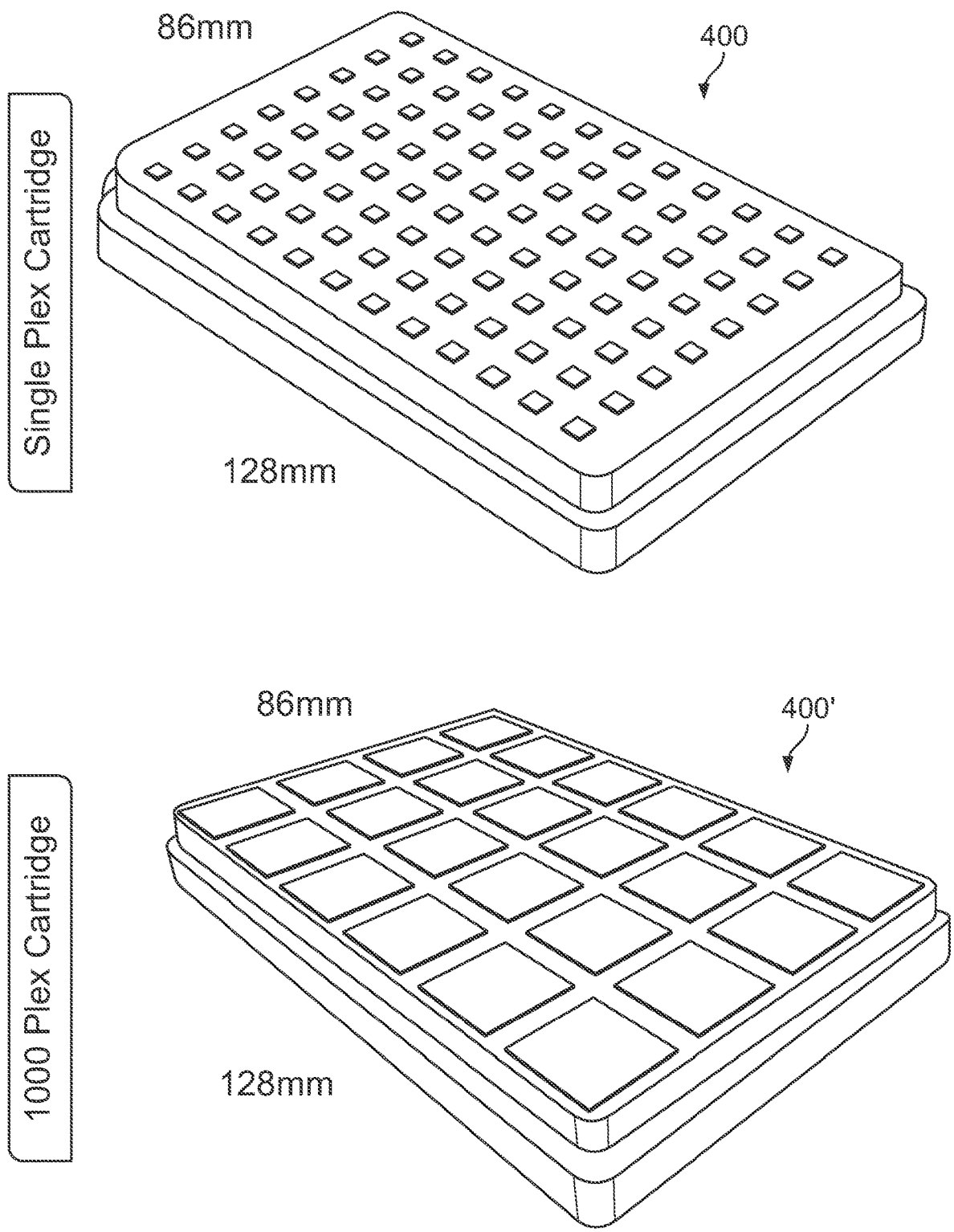
FIG. 17 is a schematic representation of a single plex cartridge and a 1,000 plex cartridge, in accordance with embodiments of the invention.

FIG. 17 shows a perspective view of a single plex consumable cartridge 400 and a 1,000 plex consumable cartridge 400', in accordance with embodiments of the invention. In these embodiments, the sensor for the single plex cartridge is configured to detect and/or quantify a single analyte, whereas the 1,000 plex cartridge is configured to simultaneously detect and/or quantify up to 1,000 different analytes. Also, the dimensions and placement of wells 440 in the gasket 430 is adjusted to accommodate the number of sensors to be included in a single well. It is understood that the technologies described herein are scalable and the cartridge may be fabricated in a wide range of shapes and sizes. In certain embodiments, the cartridge is configured to meet Society for Biomolecular Screening (SBS) dimensional standards for microplates, for example, standard 96 well microplates. Accordingly, both the wafer substrate and the base may be rectangular in shape, with the base having a length of 128 mm and a width of 86 mm, which facilitates interfacing with various liquid handling systems and ease of portability on various liquid handling platforms.

III. System Considerations

The invention also provides a system for detecting the presence, or quantifying the amount, of an analyte in a sample of interest. The system comprises (a) a receiving chamber for receiving any one or more of the foregoing sensors any one or more of the foregoing cartridges; (b) a light source for illuminating at least the first series and/or any second series and/or any third series of nanostructures; and (c) a detector for detecting a change in an optical property in at least the first series and/or any second series and/or any third series of nanostructures; and optionally (d) a computer processor implementing a computer algorithm that identifies an interface between the first concentration range and optionally any second concentration range and optionally an interface between any second concentration range and any third concentration range.

Figure 18:
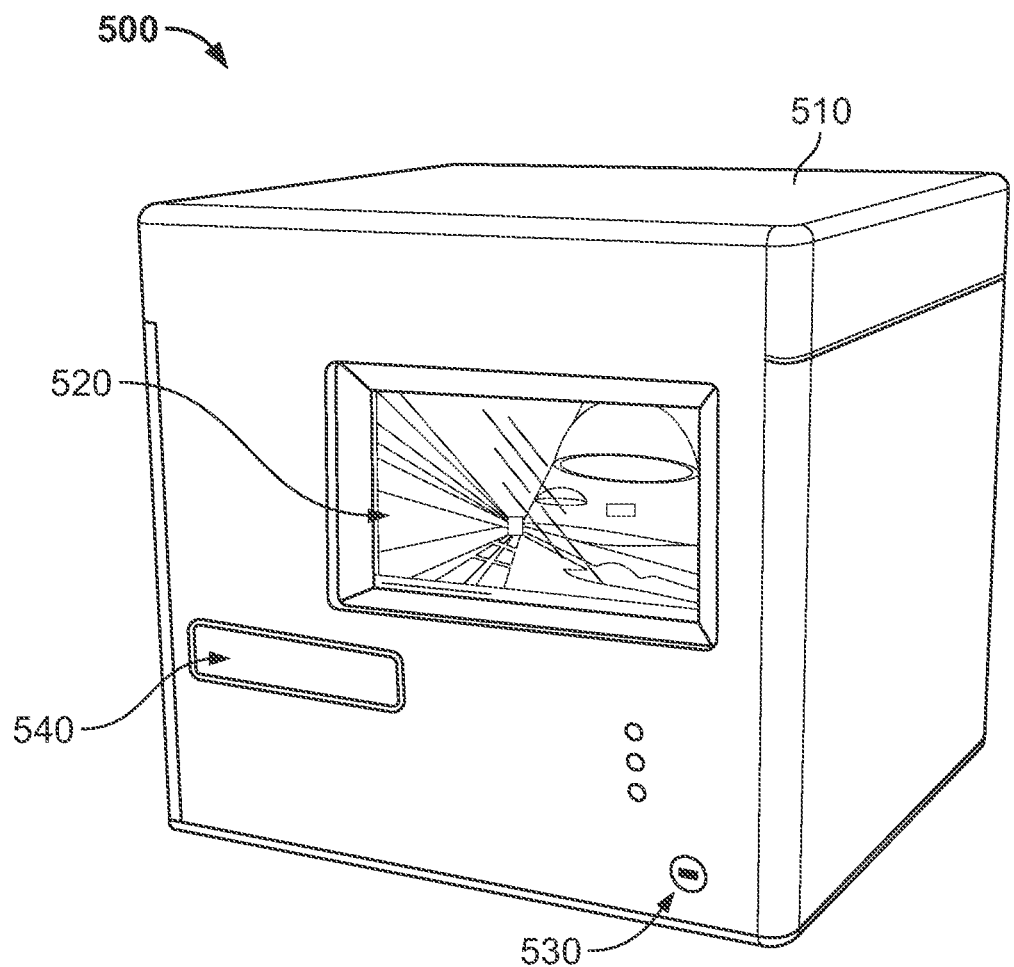
FIG. 18 is a perspective view of a detection system for use with a sensor, in accordance with an embodiment of the invention.
Figure 19:
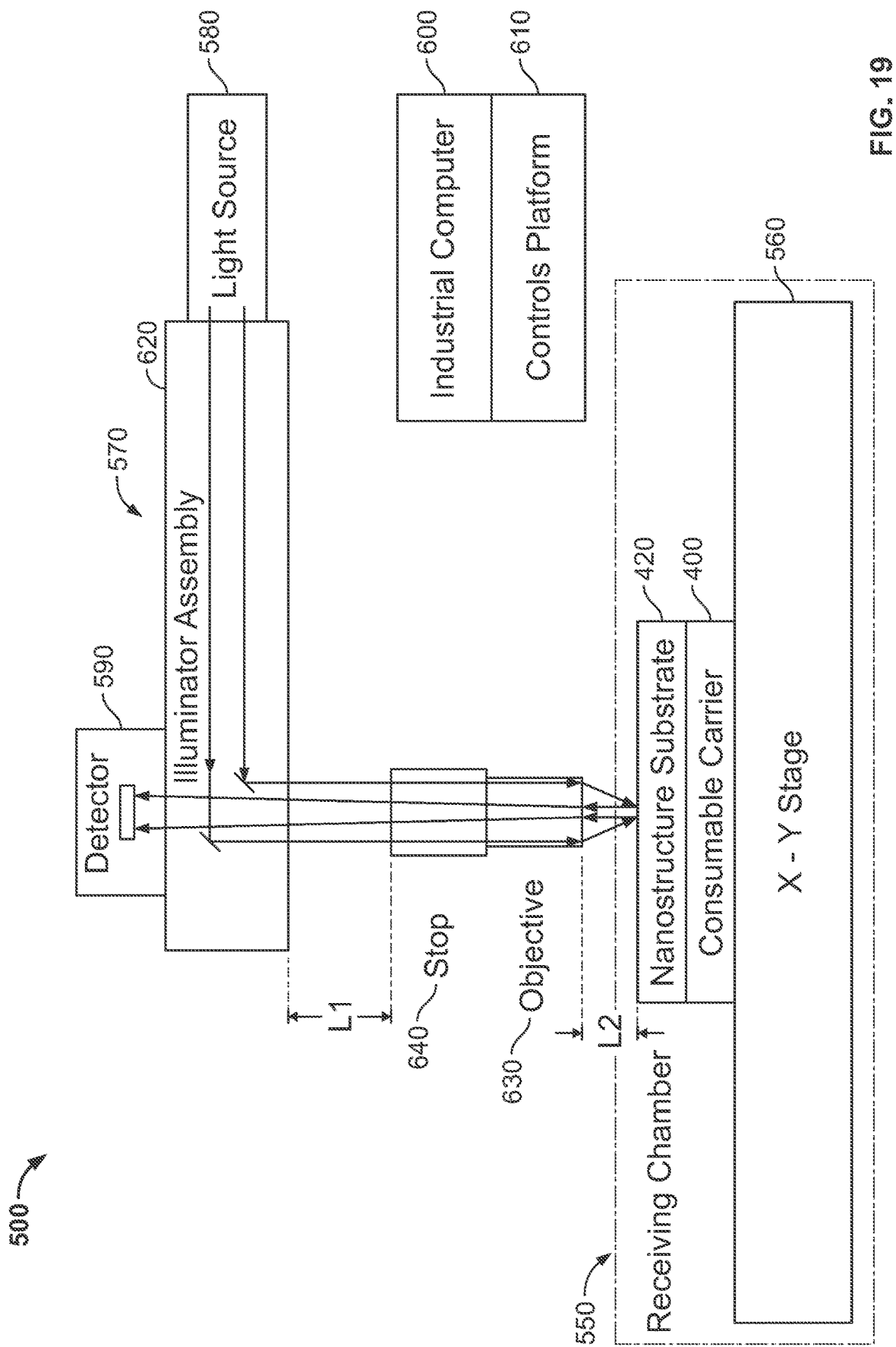
FIG. 19 is a schematic illustration depicting an exemplary optical detection system for imaging an exemplary sensor, in accordance with an embodiment of the invention.

With reference to FIGS. 18 and 19, an exemplary sensor system 500 is configured to facilitate the detection, or quantification of the amount, of an analyte in a sample of interest. The sensor system 500 can include a system housing 510 with a touch screen interface 520 and, for example, a data port 530. A load/unload door 540 in the housing may be sized and configured to enable the introduction of a cartridge 400 into a receiving chamber 550 of the sensor system that contains, for example, an X-Y stage 560 for holding and positioning the cartridge relative to an optical detection system 570. A light source 580 is configured to transmit a light through a camera/detector 590. The camera is configured to be positioned over the cartridge during use, and to detect a change in an optical property in at least a first, a second, and/or a third series of nanostructures on the substrate 420 disposed in the cartridge. The light source 580 is configured to illuminate nanostructures, for example, nanostructures disposed on the wafer substrate of a cartridge. The system can include a computer 600 including a computer processor for implementing the algorithm for identifying an interface between first concentration ranges and/or second concentration ranges and/or third concentration ranges, and for quantifying analytes in samples. The sensor system may also include a control platform 610 for controlling the system. Accordingly, the system includes three major sub-assemblies: a control system, an imaging system, and a cartridge handling system. These sub-assemblies may employ commercially available components to minimize supply chain complexity and to reduce assembly time.

The imaging system includes the optical detection system 570, in which the light source 580 is configured to direct light through an illuminator assembly 620 and an objective 630 to impinge on a plurality of nanostructures disposed upon a substrate of the sensor. After interacting with the sensor, the reflected light passes through the objective 630 and is captured by the detector 590. A stop 640 is disposed above the objective 630. The stop is a dark field light stop, which controls illumination, including how illumination reaches the substrate and how the image is transmitted to the detector. The mechanical tube length of the microscope system is indicated as L1, and may range from 10 mm to 300 mm. A working distance of the objective is designated as L2, and may range from about 2 mm to about 5 mm. In certain embodiments, L1 is greater than L2.

Figure 20:
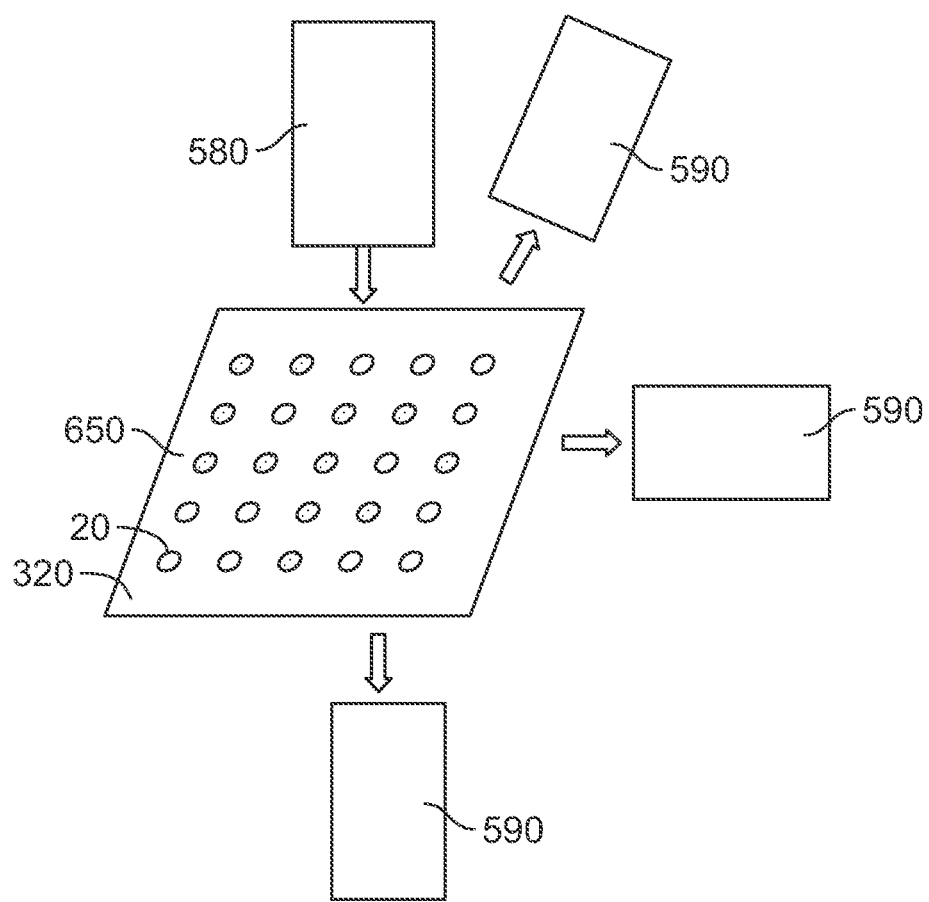
FIG. 20 is a schematic illustration depicting the interrogation of a sensor, in accordance with an embodiment of the invention. The readout signal can be optical (e.g., imaging), electrical, or mechanical.

As illustrated in FIG. 20, the measurement can be an optical measurement. For example, light source 580 can be used to irradiate substrate 320 with nanostructures 20 and analytes 650 disposed thereon, and one or more detectors 590 is/are positioned to detect the light that impinges the substrate. The light that is deflected from the substrate can be in the same direction of the light source, in the opposite direction, at orthogonal direction or at an angle to the light source. The data present in the images obtained by use of the optical detection system can be processed to provide the concentration of analyte present in a sample.

Figure 21:
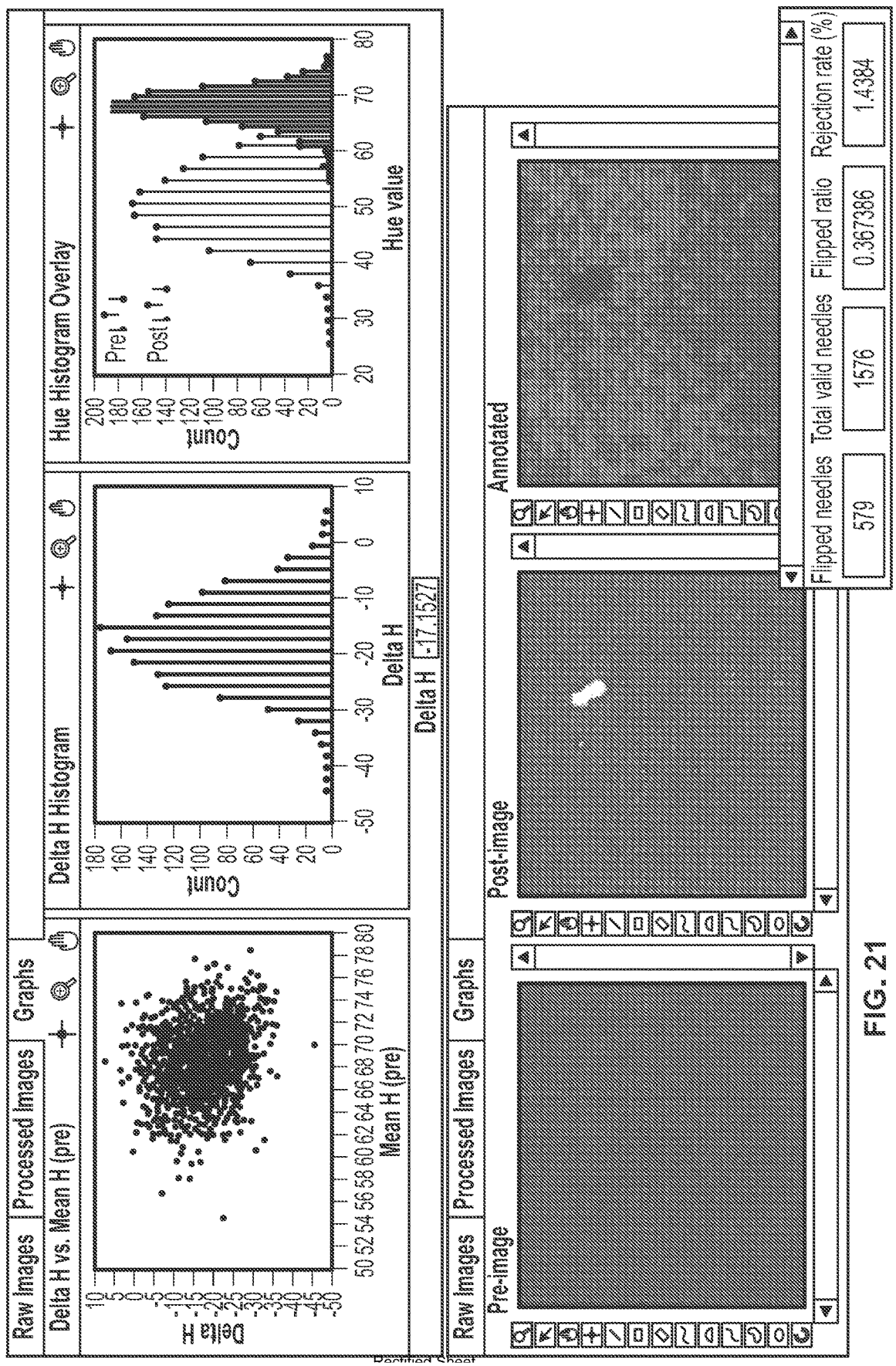
FIG. 21 is a schematic representation showing the data analysis of the output of an exemplary sensor containing digital nanostructures.

FIG. 21 shows one approach to informatics related to various embodiments of the sensor and related system. On average, all of the nanostructures in a given region are of substantially the same configuration and statistically have a substantially similar quantity or number of analyte binding sites. Accordingly, for a given concentration of analyte in the sample, each nanostructure in that region can be expected to bind the same number of molecules. In order for the sensor to have a wide dynamic range, a plurality of digital and analog regions with nanostructures of various configurations can be provided.

As the concentration of analyte in the samples range from the lowest detectable concentration to the highest detectable concentration in the digital regions of the sensor, the system is configured to detect the quantity or number of nanostructures evidencing an isolated color change corresponding to the binding of analyte above a threshold value (e.g., by flipping from one state to another). The higher the percentage of discrete nanostructures that exhibit a detectable color change or that have flipped, the higher the number of bound analytes and, accordingly, the higher the concentration of analyte in the sample. As depicted in FIG. 21, this flipping behavior can be presented visually in a variety of formats, including scatter plots that show data clustering, histograms that show data distribution, etc. Comparative images of each region can also be provided, showing a particular region of the sensor before exposure to the sample, as well as after exposure. A third annotated image can be provided depicting with greater clarity the results of the flipping determination. Numerical data is also advantageously presented, indicating absolute numbers of flipped and valid nanostructures, as well as the associated ratio value of the flipped to valid nanostructures. In particular, "flipped needles" denotes the number of sensors that have exceeded the threshold and are counted as positive. "Total valid needles" denotes the number of sensors that are counted as part of the total population. Sensors that behave outside of expected parameters are discarded and not included in subsequent analysis. Only the sensors that remain are considered "valid". The flipped ratio is the calculated value of flipped needles divided by total valid needles. The rejection rate can also be depicted, i.e., the percentage of needles that are discarded from the pre-image. This is used as a measure of sensor quality/health.

Sensors with rejection rate values of around 10% or higher are considered poor quality and generally do not provide reliable data.

At some higher threshold concentration, however, all of the digital region nanostructures have bound analyte. The digital regions of the sensor have effectively become saturated. All nanostructures have flipped and no local color change is readily evident. At this point, attention is shifted to the analog regions, that generally have larger nanostructures with more numerous binding sites.

The degree of color change of a given nanostructure can be related to the ratio of the total mass of bound molecules to the total mass of that nanostructure. Smaller analog region nanostructures that may only be able to bind less than 100 molecules can evidence a cool color hue initially (for example, in the blue/green range). Larger analog region nanostructures that may be able to bind a few hundred molecules can evidence a warmer color hue initially (for example, in the yellow/orange range). At the higher detectable concentrations in the analog regions, as more analytes bind to a given nanostructure, the detectable color hue shifts more warmly. Accordingly, an unexposed blue nanostructure exhibits a more greenish hue after binding for a particular analyte concentration in the sample. At higher analyte concentrations in the sample, the hue can shift to be more yellowish. Similarly, in an analog region with larger nanostructures and more binding sites configured to detect higher concentrations, the initial unexposed yellow nanostructure exhibits a more orange hue after binding for a particular analyte concentration in the sample. At higher analyte concentrations in the sample, the hue can shift to be more reddish.

While the color shift is detectable with solely a single analog nanostructure, regions of a series or array of similarly sized nanostructures are advantageously employed. By providing a large distribution of similarly sized nanostructures, an average readout can be provided to more reliably detect the analog region color shift and, accordingly, the detected analyte concentration.

Figure 22:
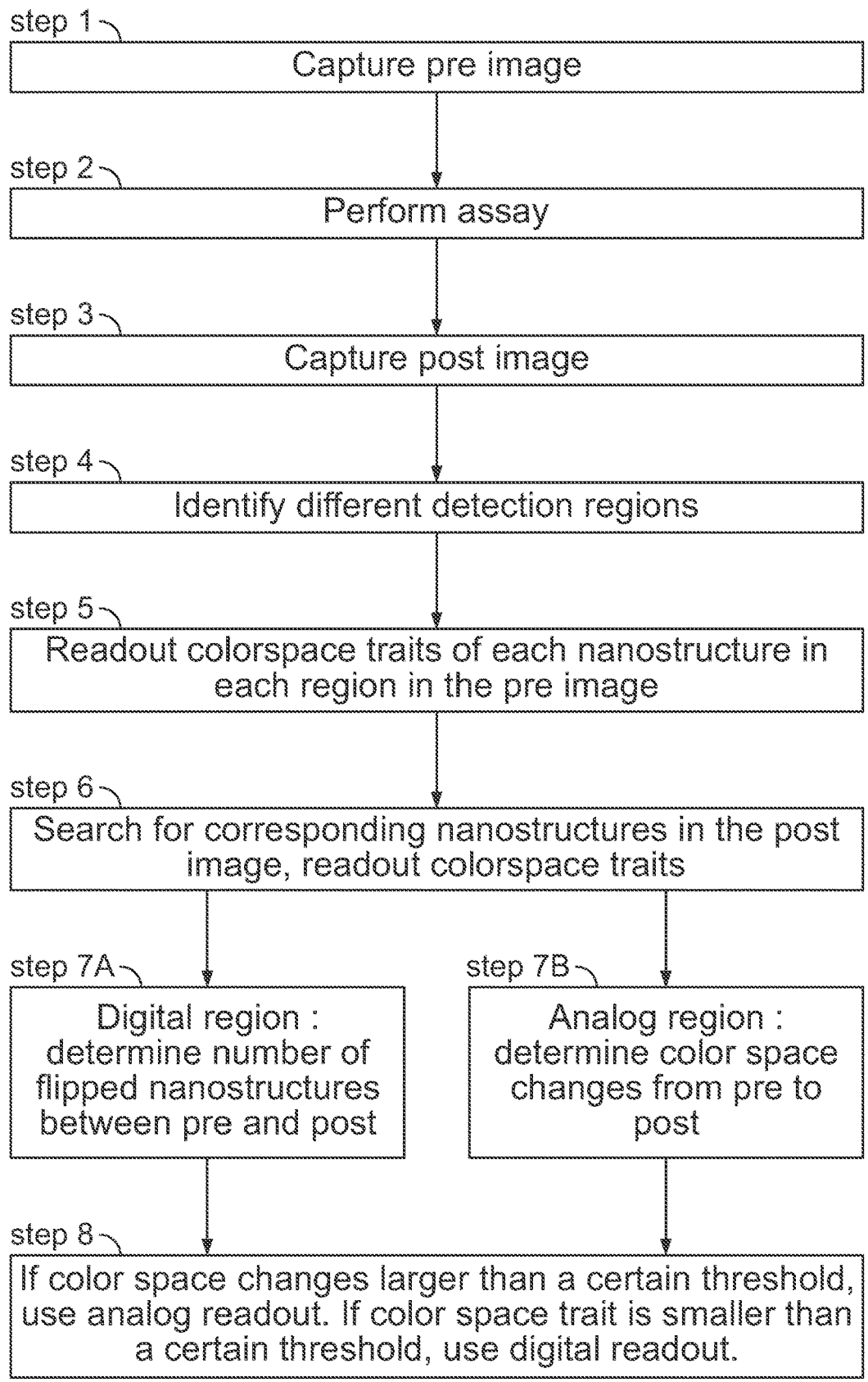
FIG. 22 is a flowchart illustrating an algorithm in accordance with an embodiment of the invention.

More specifically, FIG. 22 shows a flowchart of one approach for aggregating, at a system level, the detected output of the various digital and analog regions of one embodiment of a sensor, to reliably detect analyte concentration across the full dynamic range of the sensor. Use of this form of hybrid informatic engine algorithm permits the use of discrete digital and analog regions to reliably reject inaccurate higher concentration data from the digital regions and inaccurate lower concentration data from the analog regions.

In Step 1 of FIG. 22, the various digital and analog regions of a clean sensor are optically imaged as part of an overall image of the sensor, to provide a reliable baseline recording of the image status of each region and its associated nanostructures (e.g., presence or absence, initial color hue, etc.) for a particular sensor. In Step 2, the sensor is exposed to the sample, any analytes in the sample bind to associated sites on the nanostructures, and the sensor is subsequently conventionally prepared for subsequent imaging. In Step 3, the system captures the post exposure image of the sensor, that will be used to compare to the image of Step 1 to detect flipping in the digital regions and any color hue change in the analog regions. In Step 4, the algorithm identifies the different detection regions of the sensor (i.e., one or more digital regions and one or more analog regions) and their layout relative to the fiducial mark of the sensor. This permits the system to correlate and align the pre and post images to identify corresponding nanostructures in each image. Steps 5 and 6 entail individual, discrete analysis of the pre and post image data on a nanostructure-by-nanostructure basis in each corresponding region. For digital regions, Step 7A quantifies and counts the number of nanostructures with bound analyte by confirming a sufficiently large shift in the local image above a threshold to identify each nanostructure that has bound analyte. For analog regions, Step 7B detects color hue changes locally and across the analog region, evidencing a sufficiently large shift in the local image above the pre image color to deem the nanostructures locally and collectively to have bound analyte. In Step 8, assuming the color change in the analog region exceeds a predetermined threshold value, the analog region is deemed to have detected a concentration of analyte within its detectable range. The actual concentration of analyte corresponding to the color change is determined by comparison of the detected color change to a standard curve stored in system memory developed with known concentration control samples. If, however, the color change in the analog region fails to exceed a predetermined threshold value, the concentration of analyte is deemed to be below that reliably detectable by that analog region. If a lower concentration-configured analog region is available, a similar analysis can be performed. Otherwise, the system relies on the digital count of flipped nanostructures in the digital regions of the sensor. The actual concentration of analyte corresponding to the quantity or number of flipped nanostructures is determined by comparison of the number of flipped digital nanostructures to a standard curve stored in system memory developed with known concentration control samples.

In another embodiment, an exemplary algorithm for determining the transition between a digital quantification measurement and an analog comprises the steps of (a) measuring the nanostructures that have changed (flipped) from one state to another relative to the nanostructures in the first series upon application of the solution to be tested; (b) measuring the color space changes of nanostructures in the second series upon application of the solution to be tested; and (c) if the color space change of the second series is greater than a preselected threshold value then use the analog measurements identified in step (b) and if the color space changes of the second series is less than the preselected threshold value, then use the digital measurements identified in step (a).

Figure 23A:
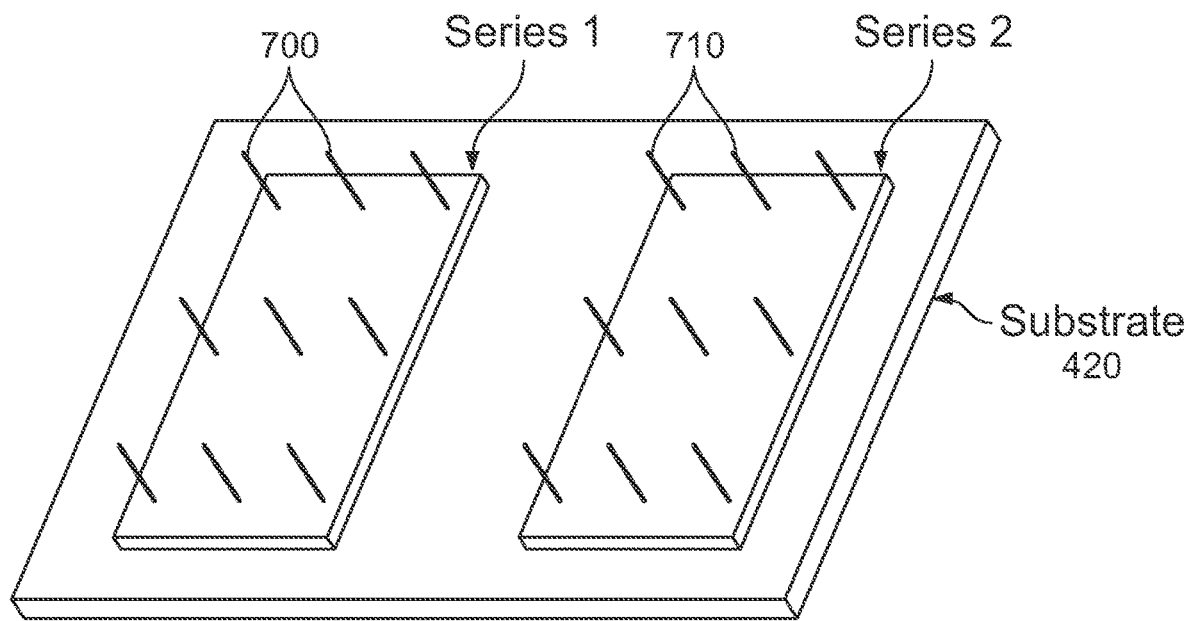
FIGS. 23A and 23B are schematic illustrations depicting series of nanostructures configured to detect and/or quantify multiple analytes at the same time, in accordance with an embodiment of the invention.
Figure 23B:
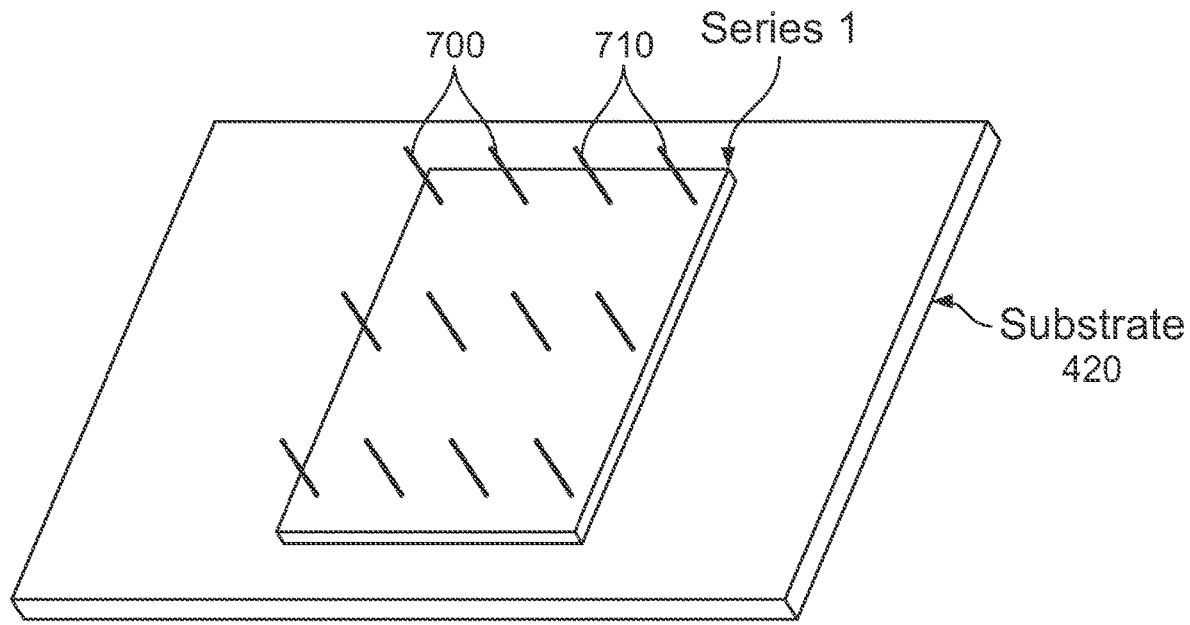

It is contemplated that, based on the choice of nanostructure and binding agent and other reagents, it is possible to detect and/or quantify multiple analytes at the same time. For example, as shown in FIG. 23A, a sensor can comprise a substrate 420 having disposed thereon a first series of nanostructures 700 and a second series of nanostructures 710 that can bind two separate and distinct analytes. It is contemplated that the substrate can contain a number of series of nanostructures, depending upon the number of analytes to be detected. Similarly, as shown in FIG. 23B, a sensor can comprise a substrate having disposed thereon a series of two different nanostructures 700, 710 that bind two separate and distinct analytes. It is contemplated that the series of nanostructures can contain nanostructures that bind to additional analytes.

IV. Assays

The invention also provides a method of detecting the presence, or quantifying the amount, of an analyte in a sample of interest. The method comprises: (a) applying at least a portion of the sample to any one or more of the foregoing sensors; and (b) detecting a change in an optical property of the first series and/or any second series and/or any third series of nanostructures thereby to detect the presence, or quantify the amount, of the analyte in the sample.

The sensor may detect the analyte is a variety of samples, for example, a body fluid, a tissue extract, and/or a cell supernatant. Exemplary body fluids include, for example, blood, serum, plasma, urine, cerebrospinal fluid, or interstitial fluid.

The method comprises combining at least a portion sample with a structure, sensor, cartridge, or system described herein, and detecting the presence and/or quantifying the amount of binding of the analyte to the structure, sensor, cartridge, or system. For example, following binding of an analyte to a nanostructure or a series of nanostructures described herein, the binding of the analyte may be detected by a change in an optically detectable property of the nanostructure or series of nanostructures. In certain embodiments, the optically detectable property is color, light scattering, refraction, or resonance (for example, surface plasmonic resonance, electric resonance, electromagnetic resonance, and magnetic resonance). In certain embodiments, electromagnetic radiation may be applied to the nanostructure or a series of nanostructures, and the applied electromagnetic radiation may be altered as the nanostructure or series of nanostructures interacts with the sample suspected of containing an analyte. For example, the presence of the analyte may result in a change of intensity, color, or fluorescence.

In another embodiment, the method includes applying a portion of the sample to a sensor comprising a first region and a second region. The first region comprises a first series of nanostructures capable of binding the analyte and producing a detectable signal indicative of a concentration of the analyte in the sample within a first concentration range. The second region comprises a second series of different nanostructures capable of binding the analyte and producing a detectable signal indicative of a concentration of the analyte in the sample within a second, different concentration range. The regions are interrogated, for example, using electromagnetic radiation to detect detectable signals from the first and second series of nanostructures, the signals being indicative of the presence and/or amount of analyte in the sample. The presence and/or amount of the analyte can then be determined from the detectable signals thereby to detect the presence, or to quantify the amount of, the analyte in the sample across both the first concentration range and the second concentration range.

In another embodiment, the method includes applying a portion of the sample to a sensor comprising a first region and a second region. The first region comprises a first series of nanostructures capable of binding the analyte and producing a detectable signal indicative of a concentration of the analyte in the sample within a first concentration range, wherein individual nanostructures of the first series that bind the analyte are optically detected upon binding the analyte, whereupon the concentration of analyte in the sample, if within the first concentration range, is determined from a number of individual nanostructures in the first series that have bound molecules of analyte. The second region comprises a second series of different nanostructures capable of binding the analyte and producing a detectable signal indicative of a concentration of the analyte in the sample within a second, different concentration range, wherein the concentration of analyte in the sample, if within the second concentration range, is determined by analog detection of a substantially uniform change in an optically detectable property of the nanostructures in the second region as a function of the concentration of the analyte. The regions are interrogated, for example, using electromagnetic radiation to detect detectable signals from the first and second series of nanostructures, the signals being indicative of the presence and/or amount of analyte in the sample. The presence and/or amount of the analyte can then be determined from the detectable signals thereby to detect the presence, or to quantify the amount of, the analyte in the sample across both the first concentration range and the second concentration range.

In an exemplary assay, a nanostructure or series of nanostructures is functionalized with a binding agent (for example, an antibody) that binds an analyte of interest. After functionalization, a sample (for example, a fluid sample) including the target analyte is added to the nanostructure or series of nanostructures under conditions to permit the binding agent to form a binding agent-analyte complex, if the analyte is present in the sample. The binding of analyte to the antibody results in a change in an optically detectable property of the nanostructure or series of nanostructures. It is contemplated that, for certain assays, for example, a label free assay, formation of the binding agent-analyte complex alone results in a change in an optically detectable property of the nanostructure or series of nanostructures. For other assays, for example, label-based assays, the second binding agent that forms a complex with the analyte may also include a label that directly or indirectly in the complex results in, or increases the change in, an optically detectable property of the nanostructure or series of nanostructures. It is contemplated that nanostructures can detect the presence and/or amount of an analyte without having a particle or bead attached to or otherwise associated with the nanostructure.

In an exemplary sandwich immunoassay, a nanostructure or series of nanostructures is functionalized with a first binding agent (for example, a first antibody) that binds the analyte of interest. After functionalization, a sample (for example, a fluid sample) to be analyzed for the presence and/or amount of a target analyte is added to the nanostructure or series of nanostructures under conditions that permit the first binding agent to form a first binding agent-analyte complex, if the analyte is present in the sample. Then a second binding agent (for example, a second antibody) that binds the analyte of interest is added to the nanostructure or series of nanostructures under conditions to permit the second binding agent to form a second binding agent-analyte complex. The binding of the analyte to the first and second binding agents results in a complex in a "sandwich" configuration. The formation of the sandwich complex can result in a change in an optically detectable property of the nanostructure or series of nanostructures. It is contemplated, however, that for certain assays for example, label free assays, formation of the sandwich complex alone results in a change in an optically detectable property of the nanostructure or series of nanostructures. For other assays, for example, label-based assays, the second binding agent in the sandwich complex can include a label that either directly or indirectly results in or increases the change in an optically detectable property of the nanostructure or series of nanostructures.

Figure 24:
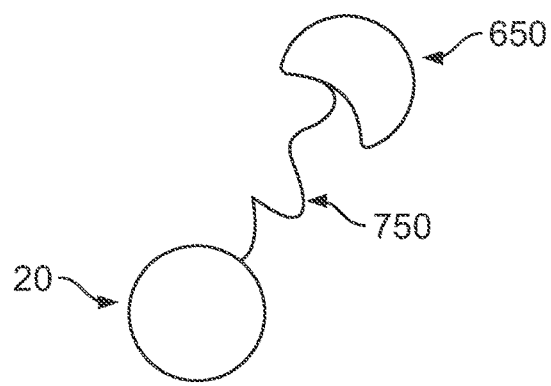
FIG. 24 is a schematic illustration depicting the interaction between an analyte and a nanostructure, in accordance with an embodiment of the invention.
Figure 25:
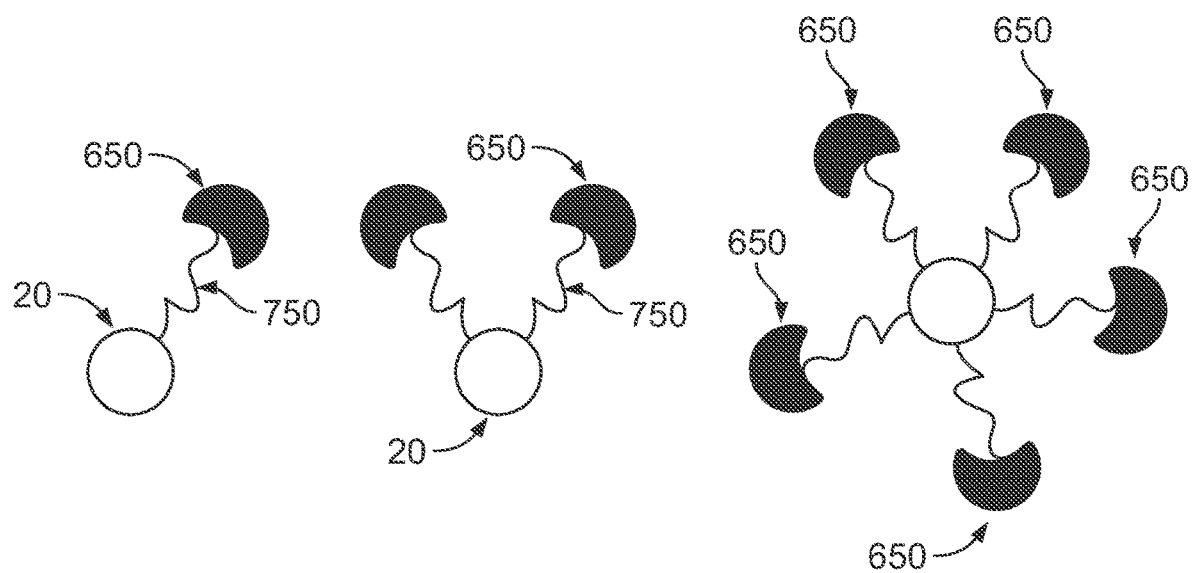
FIG. 25 is a schematic representation depicting the binding capacity of a nanostructure, by capturing, from left to right, 1, 2 and 5 analytes, in accordance with an embodiment of the invention.
Figure 26:
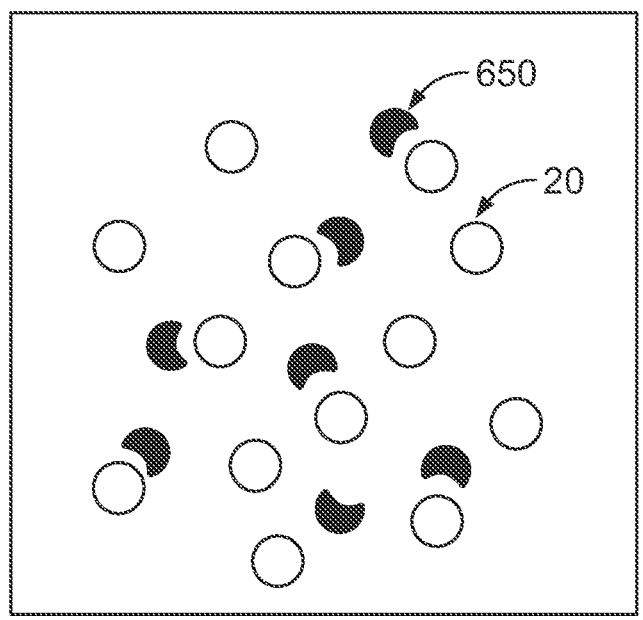
FIG. 26 is a schematic illustration depicting a non-saturating assay where there are fewer analytes than the number of nanostructures capable of capturing the analytes, in accordance with an embodiment of the invention.
Figure 27:
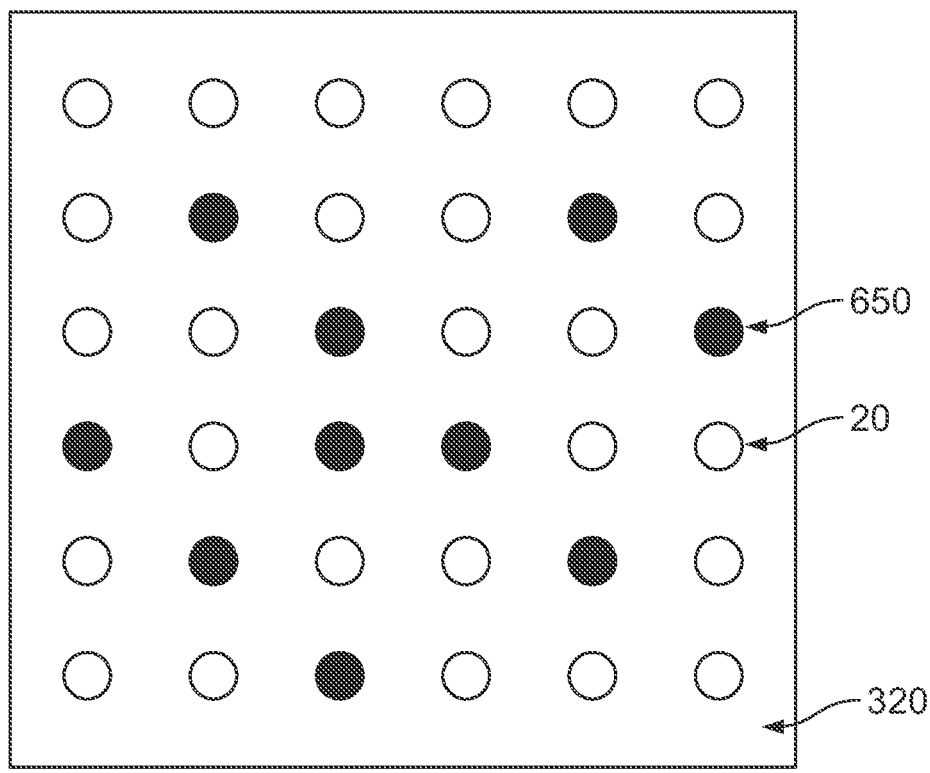
FIG. 27 is a schematic illustration depicting series of nanostructures in an array under non-saturating assay conditions where analytes are bound by a fraction of the nanostructures in the array, in accordance with an embodiment of the invention.

FIG. 24 depicts an exemplary assay whereby an analyte 650 interacts with a binding agent 750 immobilized on a nanostructure 20. The capturing capacity of the nanostructure is determined by both the dimensional relation between the nanostructure and the available capturing agent. FIG. 25 depicts an exemplary assay where there is a 1:1 ratio between nanostructure 20 and bound analyte 650 (left panel), a 1:2 ratio between nanostructure and bound analyte (center panel), and a 1:5 ratio between nanostructure and bound analyte (right panel). FIG. 26 depicts an exemplary assay where nanostructures 20 outnumber analytes 650, in which case, each nanostructure is likely to capture at most one analyte. The nanostructures 20 can be directly fabricated with nanofabrication technologies on a substrate, as discussed above. FIG. 27 depicts nanofabricated nanostructures 20 disposed on a silicon substrate 320, with analytes 650 bound to a portion of the nanostructures. The binding between analytes and nanostructures occur on a solid interface. The nanostructures may be measured to determine the number of binding analytes on its surface. FIGS. 24-27 depict examples of a label-free immunoassay wherein a single binding agent (for example, antibody or aptamer) is used to bind a target analyte. This method can be used to measure or otherwise quantify binding affinities, binding kinetics (on and off rate), etc.

FIG. 28 depicts an exemplary label-free immunoassay wherein a plurality of first antibodies (Ab 1) are immobilized upon the fluid exposed surface of a nanostructure 20. Thereafter, a sample including the analyte to be detected and/or quantified (0) is contacted with the nanostructures either alone or in combination with a second antibody (Ab1) that binds the analyte, preferably via a second, different epitope. The second antibody (Ab2) can be added after the analyte. The two antibodies (Ab1 and Ab2) and analyte (0), if present, form a complex that is immobilized on the surface of the nanostructure 20. The binding of the complex to the nanostructure may cause a change in a property of the nanostructures that can be detected with a detection system. FIG. 29 depicts an exemplary label-based immunoassay that is performed essentially as described above in connection with FIG. 28, except that, in this embodiment, the second antibody is labeled. The binding of the complex to the nanostructure 20 can be detected via the label 760, either directly (for example, via a gold label) or indirectly (for example, via an enzyme that creates a further product) to cause a change in a property of the nanostructures that can be detected with the detection system.

In an alternative assay, a sample (e.g., a fluid sample) to be analyzed for the presence and/or amount of a target analyte is incubated with (i) a first binding agent (e.g., an antibody) under conditions to permit the first binding agent to form a first binding agent-analyte complex, if the analyte is present in the sample, and (ii) a second binding agent (e.g., a second antibody) that binds the analyte of interest under conditions to permit the second binding agent to form a second binding agent-analyte complex. The binding of the analyte to the first and second binding agents results in a complex in a "sandwich" configuration, which occurs free in solution. Then, depending upon the assay, the first binding agent, second binding agent, and/or analyte, either complexed or uncomplexed, are added to a nanostructure or series of nanostructures, under conditions such that the complex or component thereof is bound by the nanostructure or series of nanostructures to create a change in a property (for example, an optically detectable property) of the nanostructure or series of nanostructures. In certain embodiments, one or both of the antibodies is labeled with biotin, and the sandwich complex can become immobilized on the surface if any nanostructure or a series of nanostructures that have been functionalized with, for example, avidin or biotin.

Typically, when the binding agent is an antibody, then between each assay step, the nanostructure with bound analyte can be washed with a mild detergent solution. Typical protocols also include one or more blocking steps, which involve use of a non-specifically-binding protein such as bovine serum albumin or casein to block or reduce undesirable non-specific binding of protein reagents to the nanostructure.

Exemplary labels for use in label-based assays include a radiolabel, a fluorescent label, a visual label, an enzyme label, or other conventional detectable labels useful in diagnostic or prognostic assays, for example, particles, such as latex or gold particles, or such as latex or gold sol particles. Exemplary enzymatic labels include, for example, horseradish peroxidase (HRP), alkaline phosphatase (AP), β-galactosidase (β-Gal), and glucose oxidase (GO). When the label is an enzyme, the assay includes the addition of an appropriate enzyme substrate that produces a signal that results in a change in an optically detectable property of the nanostructure or series of nanostructures. The substrate can be, for example, a chromogenic substrate or a fluorogenic substrate. Exemplary substrates for HRP include OPD (o-phenylenediamine dihydrochloride; which turns amber after reaction with HRP), TMB (3,3',5,5'-tetramethylbenzidine; which turns blue after reaction with HRP), ABTS (2,2'-azino-bis [3-ethylbenzothiazoline-6-sulfonic acid]-di-ammonium salt; which turns green after reaction with HRP), 2,2'-azino-bis(3-ethylbenzothiazoline-6-sulfonic acid (ABTS); 3-amino-9-ethylcarbazole (AEC); 3,3'Diaminobenzidine (DAB); StayYellow (AbCam™ product); and 4-chloro-1-napthol (4-CN, or CN). Exemplary substrates for alkaline phosphatase include PNPP (p-Nitrophenyl Phosphate, Disodium Salt; which turns yellow after reaction with alkaline phosphatase), 5-bromo-4-chloro-3-indolyl phosphate (BCIP) and p-nitroblue tetrazolium chloride (NBT); Stay Green (AbCam™ product); and 4-Chloro-2-methyl benzenediazonium (aka Fast Red). Exemplary substrates for β-Gal include o-nitrophenyl-β-D-galactopyranoside (ONPG) and 5-Bromo-4-Chloro-3-indolyl-B-D-Galactopyranoside (X-Gal). Exemplary substrates for GO include 2,2',5-5'-tetra-p-nitrophenyl-3,3'-(3,3'-dimethoxy-4,4'-biphenylene)-di tetrazolium chloride (t-NBT). A preferred enzyme has a fast and steady turnover rate.

When desirable, a label and a binding agent may be linked, for example, covalently associated, by a linker, for example, a cleavable linker, e.g., a photocleavable linker, an enzyme cleavable linker. A photocleavable linker is a linker that can be cleaved by exposure to electromagnetic radiation (for example, visible light, UV light, or infrared light). The wavelength of light necessary to photocleave the linker depends upon the structure of the photocleavable linker used. Exemplary photocleavable linkers include, but are not limited to, chemical molecules containing an o-nitrobenzyl moiety, a p-nitrobenzyl moiety, a m-nitrobenzyl moiety, a nitoindoline moiety, a bromo hydroxycoumarin moiety, a bromo hydroxyquinoline moiety, a hydroxyphenacyl moiety, a dimethozybenzoin moiety, or any combinations thereof. Exemplary enzyme cleavable linkers include, but not limited to, DNA, RNA, peptide linkers, β-glucuronide linkers, or any combinations thereof.

Figure 30:
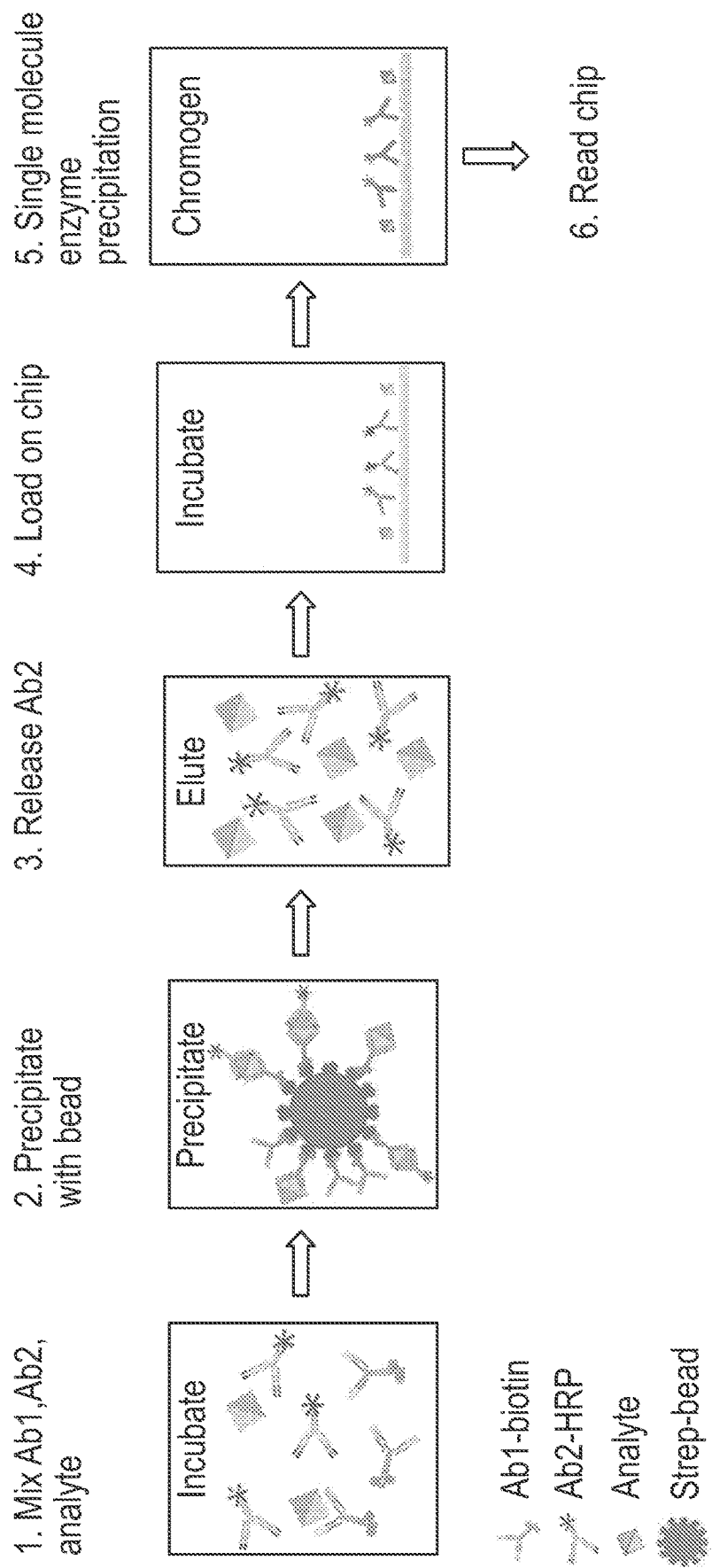
FIG. 30 is a schematic illustration of an exemplary particle-based assay for determining the presence and/or amount of analyte (antigen) using a pair of antibodies (Ab1 and Ab2) that bind the antigen, where binding occurs in solution prior to detection via (Ab2) antibody capture by an activated nanostructure, in accordance with an embodiment of the invention.

FIG. 30 illustrates an exemplary analyte quantification assay that includes a first antibody which is labeled with biotin (Ab1) and a second antibody that is labeled with HRP (Ab2). Neither antibody is immobilized on a nanostructure at this stage. Each antibody binds to the target analyte, for example, via separate epitopes on the analyte. Incubation of the first antibody, second antibody, and analyte results in the formation of a sandwich complex (see, Step 1). The sandwich complex is then captured by an avidin or streptavidin coated surface (e.g., streptavidin coated beads) that binds to the biotin conjugated to Ab1 (see, Step 2). It is contemplated that this capture strategy captures more analyte than would otherwise be captured by directly capturing the analyte with an antibody pre-immobilized (for example, coated) on a solid surface. After a washing step, if desired, the Ab2 is eluted from the streptavidin surface (see, Step 3) by changing the solution conditions (for example, by changing pH, salt concentration or temperature) and then applied to an activated (but not functionalized) nanostructure or series of activated nanostructures (see, Step 4) whereupon the eluted Ab2 molecules are captured by the activated nanostructures. A HRP substrate (for example, TMB) then is applied to the nanostructure or series of nanostructures, which is then catalytically converted into product (for example, a precipitate) formed on the nanostructure or series of nanostructures which creates a detectable signal (see, Step 5), which can then be detected by the system (see, Step 6).

Figure 31:
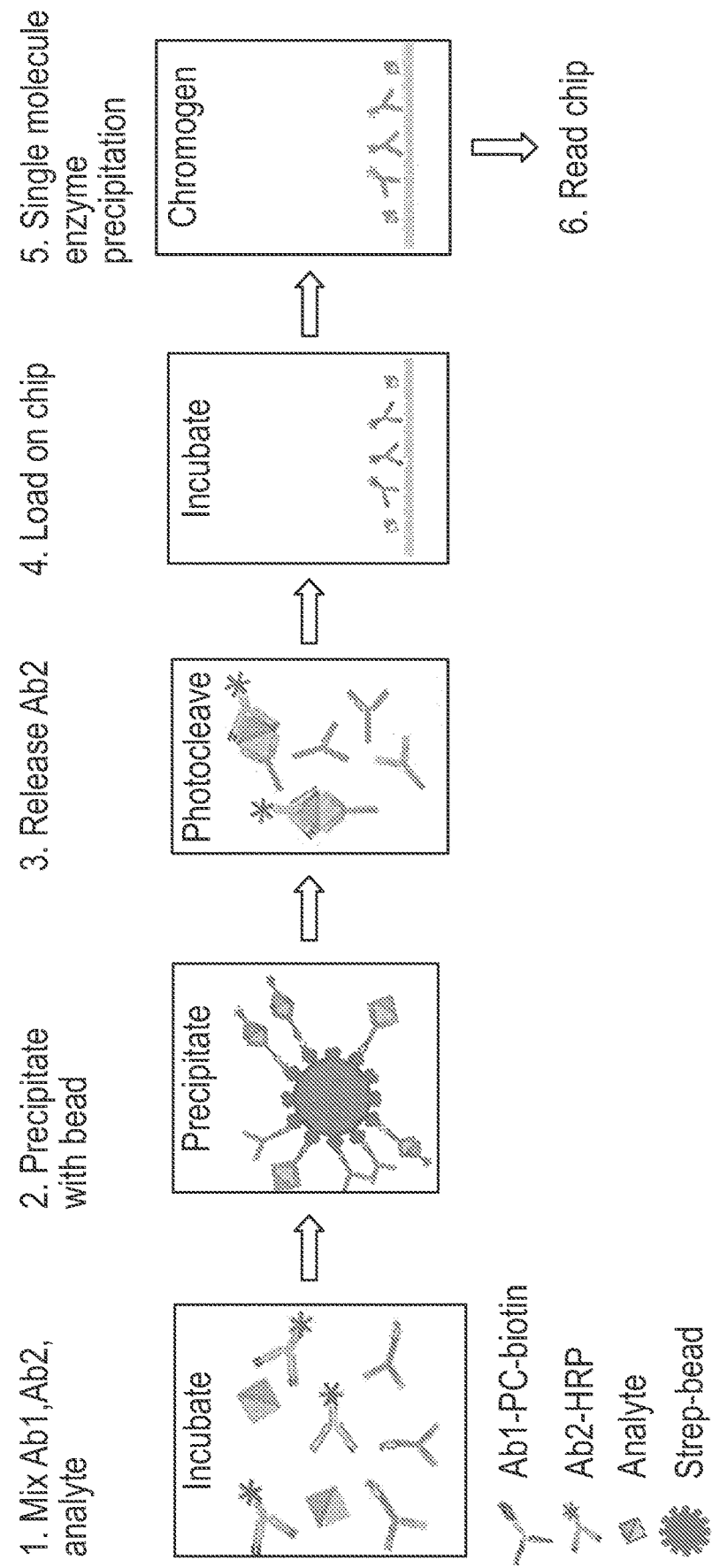
FIG. 31 is a schematic illustration of an exemplary particle-based assay for determining the presence and/or amount of analyte (antigen) using a pair of antibodies (Ab1 and Ab2) that bind the antigen, wherein binding occurs in solution prior to detection via (Ab2) antibody capture by an activated nanostructure, in accordance with an embodiment of the invention.

FIG. 31 illustrates another exemplary analyte quantification assay including a first antibody which is labeled with biotin (Ab1) and a second antibody which is labeled with HRP (Ab2). Ab1 is covalently linked to the biotin via a photocleavable linker. Each antibody binds to the target analyte. Incubation of the first antibody, second antibody, and analyte results in the formation of a sandwich complex (see, Step 1). The sandwich complex is then captured by an avidin or streptavidin coated surface (e.g., a streptavidin coated bead) that binds to the biotin on Ab1 (see, Step 2). After enrichment and washing, if desired, the photocleavable linker is then cleaved, removing the sandwich complex from the streptavidin surface (see, Step 3), and the complex is applied to an activated nanostructure or series of activated nanostructures (see, Step 4) whereupon the Ab2 or Ab2 containing complexes are captured by the activated nanostructure(s). A HRP substrate (for example, TMB) then is applied to the nanostructure or series of nanostructures, which is then catalytically converted into product (for example, a precipitate) formed on the nanostructure or series of nanostructures which creates a detectable signal (see, Step 5), which can then be detected by the system (see, Step 6).

Figure 32:
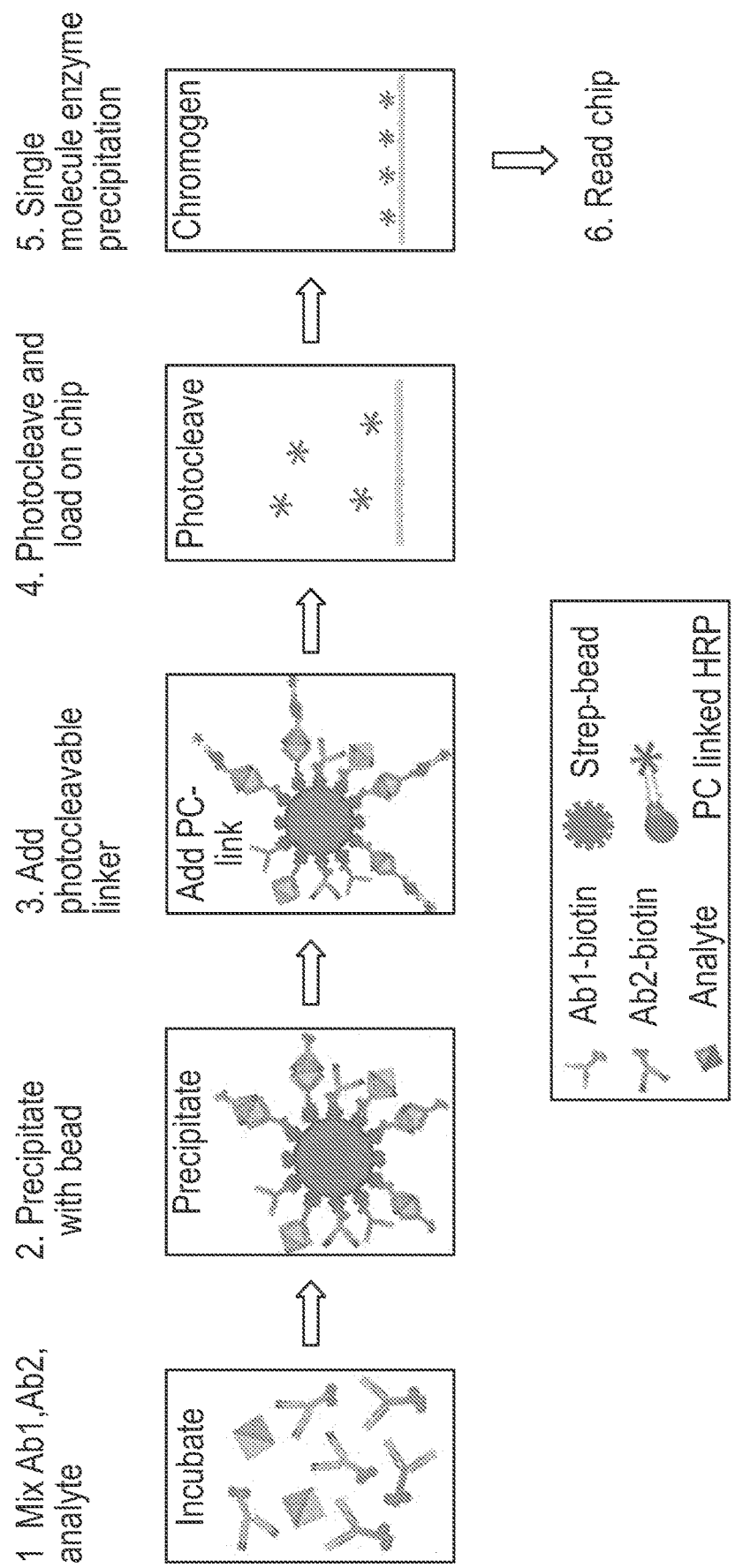
FIG. 32 is a schematic illustration of an exemplary particle-based assay for determining the presence and/or amount of analyte (antigen) using a pair of antibodies (Ab1 and Ab2) that bind the antigen, wherein binding occurs in solution prior to detection via enzyme (HRP) capture by an activated nanostructure, in accordance with an embodiment of the invention.

FIG. 32 illustrates an another exemplary analyte quantification assay that includes a first antibody that is labeled with biotin (Ab1) and a second antibody which is labeled with biotin (Ab2). Each antibody binds to the target analyte. Incubation of the first antibody, second antibody, and analyte results in the formation of a sandwich complex (see, Step 1). The sandwich complex is then captured by an avidin or streptavidin coated surface (e.g., a streptavidin coated bead) that binds to the biotin on Ab1 or Ab2 (see, Step 2). Then, HRP covalently linked to streptavidin via a photocleavable linker is added (Step 3), which binds to the free biotin on Ab 1 or Ab2. After enrichment and washing, if appropriate, the photocleavable linker is cleaved to release the HRP, which is then applied to and captured by an activated nanostructure or series of activated nanostructures (see, Step 4). The addition of a HRP substrate creates a product (for example, a precipitate) on the surface of a nanostructure or series of nanostructures which creates a detectable signal (see, Step 5), which can then be detected by the system (see, Step 6).

Figure 33:
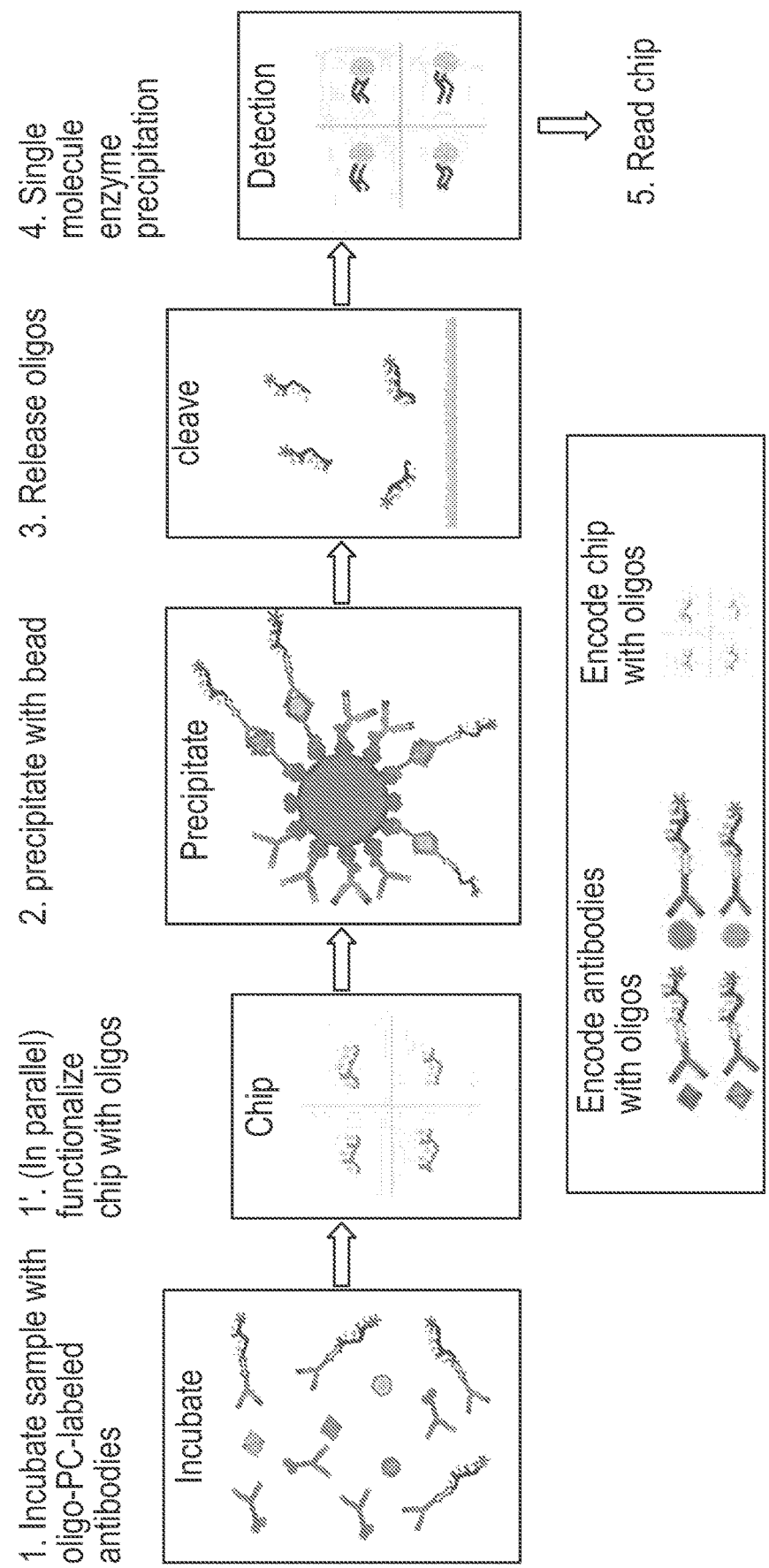
FIG. 33 is a schematic illustration of an exemplary particle-based assay for determining the presence and/or amount of analyte (antigen) using a pair of antibodies (Ab1 and Ab2) that bind the antigen, wherein binding occurs in solution prior to detection via oligonucleotide capture by a nanostructure functionalized with a complimentary oligonucleotide, in accordance with an embodiment of the invention.

FIG. 33 illustrates another exemplary analyte quantification assay that includes a first antibody that is labeled with (for example, covalently coupled to) biotin and a second antibody that is labeled with (for example, covalently coupled to) an oligonucleotide. The oligonucleotide is linked to the antibody by a cleavable linker located at one end of the oligonucleotide, and, the other end, optionally contains a detectable label (for example, a fluorophore or enzyme). The cleavable linker can be an uracil or a plural of uracil inserted at one end of the oligonuecleotide. The oligonucleotide can serve as a bar code to the target analyte in Step 1. This can be performed with antibodies that bind to different analytes to facilitate a multiplexing reaction. Each antibody binds to the target analyte if present in the sample. Incubation of the first antibody, second antibody, and analyte results in the formation of a sandwich complex (see, Step 1). In parallel, the nanostructure or series of nanostructures can be functionalized with oligonucleotides complimentary to the oligonucleotides that act as a bar code for each analyte to be detected (see, Step 1'). The sandwich complex is then captured by a streptavidin coated surface (e.g., a streptavidin coated bead) that binds to the biotin on the first antibody (see, Step 2). After enrichment, and washing, as appropriate, the oligonucleotides in each complex can be released by cleavage of the cleavable linkers (see, Step 3), which are applied to and captured by the complementary oligonucleotides attached to the nanostructure or series of nanostructures (see, Step 4), which is then detected by the system (Step 5). The identity and/or concentration of the analyte can be determined from the bar code oligonucleotides captured by the complementary oligonucleotides disposed on the surface of the nanostructure.

Figure 34A:
FIGS. 34A-34C are schematic illustrations depicting reagents for use in an exemplary multiplex assay.
Figure 34B:
Figure 34C:
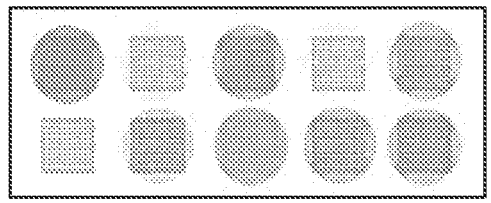

FIG. 34 illustrates reagents for an exemplary multiplex detection assay. For example, a plurality of individual beads are coated with a corresponding plurality of capture antibodies Ab 1, Ab2, Ab3 etc. that bind to a corresponding plurality of target analytes (FIG. 34A). A corresponding plurality of detection antibodies labeled with oligonucleotides (bar code for analyte) via a cleavable (for example, a photocleavable) linker (see, FIG. 34B) and then combined with the particles. FIG. 34C represents a sensor with 2×5 nanostructure array, where different regions contain capture oligonucleotides complementary to the corresponding bar code oligonucleotides. The beads are combined and mixed with sample. After the sandwich complexes are permitted to form, the beads are washed and the oligonucleotides are released by cleavage of the cleavable linker. The released bar code oligonucleotides (either with or without a label) are then applied to the sensor with the regions of the capture oligonucleotides (see, FIG. 34D), which are captured and detected as appropriate. The number of antibody coated beads, number of oligonucleotide labeled antibodies and number of oligonucleotide printed regions can be scaled depending upon the desired assay to be performed.

Throughout the description, where compositions (for example, sensors, cartridges or systems) are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition (for example, a sensor, cartridge or system) or a method described herein can be combined in a variety of ways without departing from the spirit and scope of the present invention, whether explicit or implicit herein. For example, where reference is made to a particular feature, that feature can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1—Creation and Testing of An Exemplary Sensor For Binding Tau Protein

This example describes the creation of a sensor useful in quantifying Tau protein in a sample over a dynamic range of about 6 logs in concentration.

A silicon wafer was cleaned and dehydrated. A thick layer of $SiO_2$ (25 nm) was deposited on the silicon wafer using chemical vapor deposition. Polymethylmethacrylate 950 A2 (PMMA 950 A2) was spun coated at 3,000 rpm for 45 seconds onto the $SiO_2$ layer. The wafer was heated at 180° C. for 90 seconds. Electron beam lithography was used to write nanostructure cross sections on the PMMA layer. The PMMA was developed with methyl isobutyl ketone/isopropyl alcohol (MIBK/IPA). A thermal evaporator was used to coat a thin layer (30 nm) of aluminum on the PMMA. The wafer was then immersed in acetone overnight for lift-off of the aluminum layer. Using aluminum as a hard mask, reactive ion etching was used to first etch the $SiO_2$ layer (25 nm) and then etch into silicon for about 150 nm to form the nanostructures. The pitch between each nanostructure was about 2 µm. The diameter of the digital nanostructures was about 95 nm. The diameter of the analog nanostructures grouped into three sizes was about 110 nm, 120 nm, and 130 nm.

To functionalize the nanostructures with antibodies, the nanostructures were immersed in 5% of (3-Aminopropyl) triethoxysilane (APTMS) in ethanol for 30 minutes on a rocking platform. Additional ethanol was used to thoroughly rinse the chip to wash off excessive ATPMS on the chip. The chip was cured on a hot plate for 6 hours. Dark field optical images of nanostructures were captured using a light microscope and these images were assigned as pre-images.

To activate the APTMS-modified sensor surface, 5% glutaraldehyde in phosphate buffered saline (PBS) was added for one hour. After rinsing in deionized water, 5 µg/mL Tau antibody in PBS was coated onto the sensor surface for two hours. Then 3% bovine serum albumin and 1% casein in PBS was applied for one hour to block non-specific binding to the surface. Different concentrations of recombinant Tau proteins were then applied to the sensor for two hours. Biotinylated Tau-antibody at 1 µg/mL was applied to the sensor for 1 hour to form a sandwich with the recombinant Tau proteins. Then, 0.5 µg/mL streptavidin-HRP was added and permitted to associate with biotin group on the Tau antibody for 30 minutes. Tetramethylbenzidine (TMB) was used to form a non-soluble mass on the sandwich. The change in mass induced a color change of the nanostructure having a Tau protein bound to it.

Figure 37:
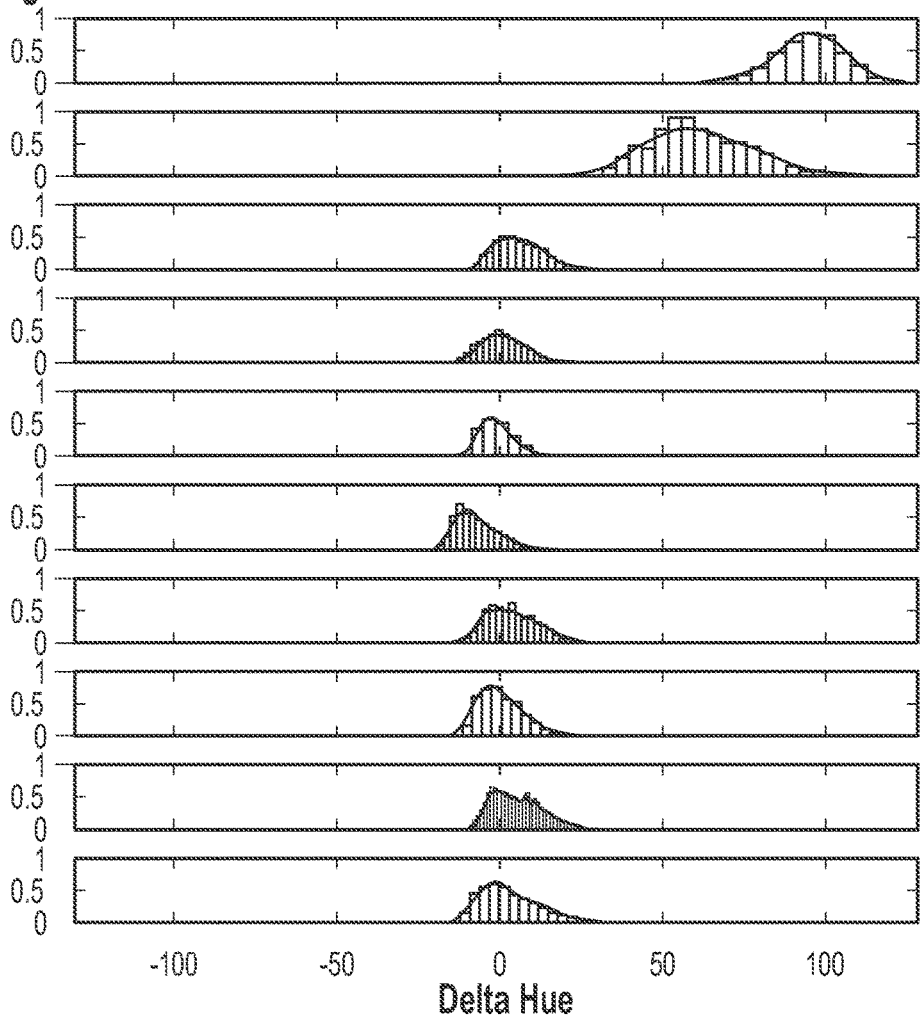
FIG. 37 is a histogram of delta hue created by an array of nanostructures in an analog array of a sensor at various concentrations of Tau protein.

After rinsing the chip, dark field images were taken of the nanostructure, which were assigned as post-images. Images of the resulting sensors (and data outputs) are shown in FIGS. 3B, 35 and 37.

Figure 35:
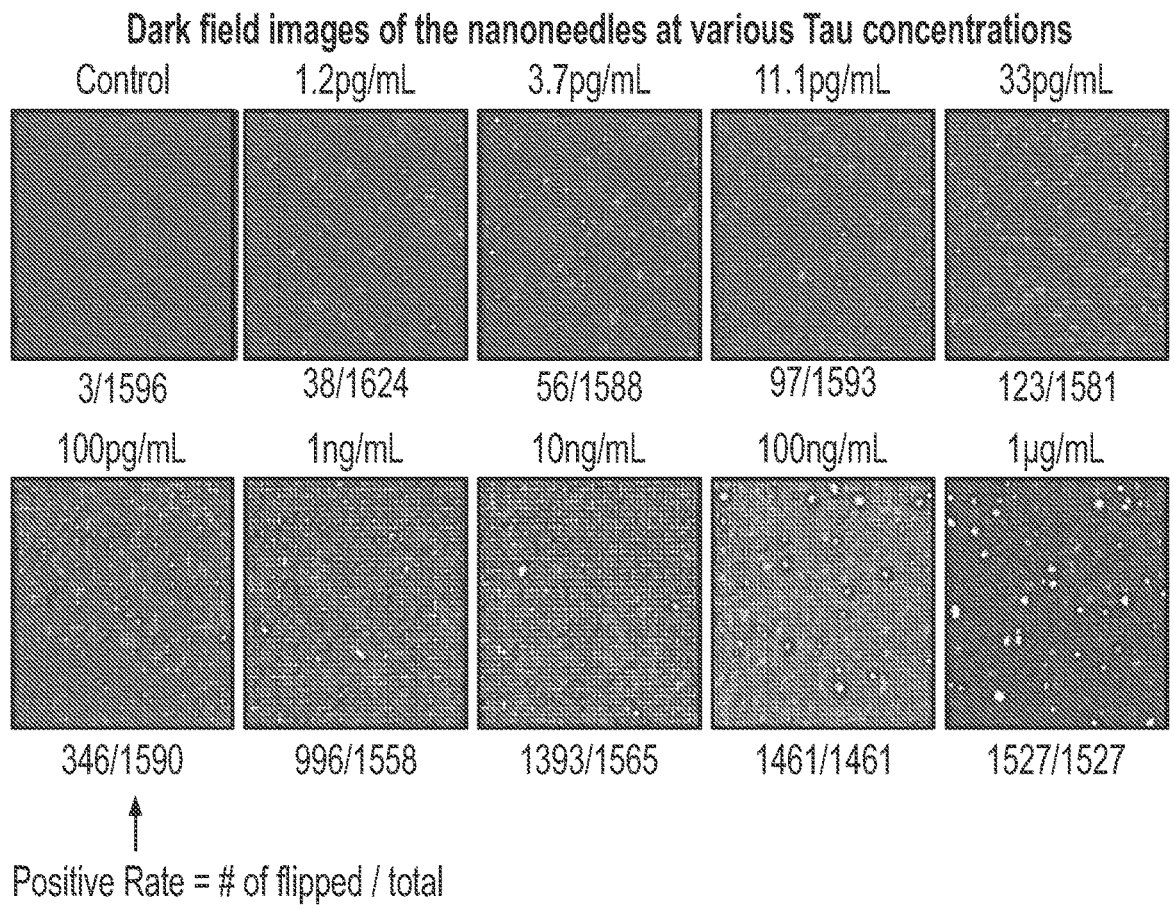
FIG. 35 is a pictorial representation of dark field images of nanostructures within a digital array at various concentrations of Tau protein.
Figure 36:
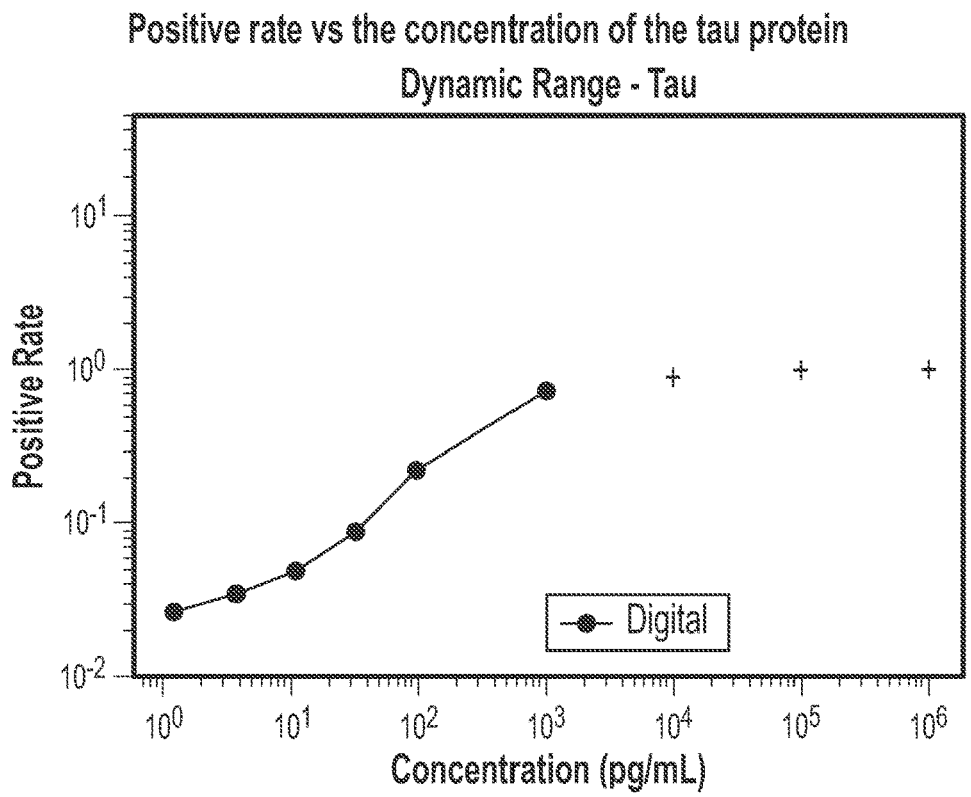
FIG. 36 is a graph illustrating the positive rate versus the concentration of the Tau protein in the sensor of FIG. 35, where the digital array of a sensor becomes saturated at concentrations greater than 1 ng/mL.

A series of post-images of nanostructures in the digital section are shown in FIG. 35 at different Tau concentrations. The positive rate is defined by the percentage of nanostructures that had flipped from one state to another. As the concentration increased, the positive rate also increased (see, FIG. 36). When the concentration reached about 1 ng/mL, most of the nanostructures had experienced color flips and therefore, increasing concentrations of analytes no longer changed the positive rate (as shown in FIG. 36).

Figure 38:
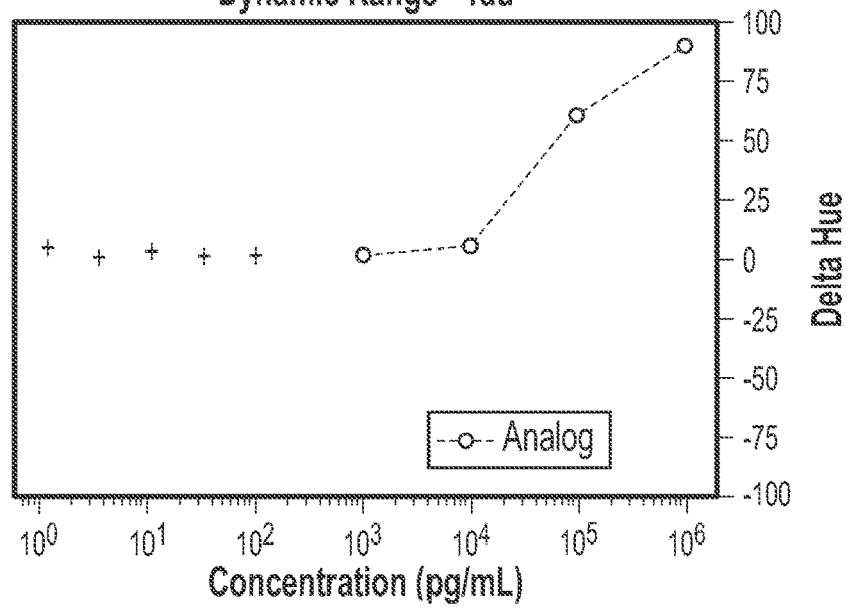
FIG. 38 is a graph of average delta hue as a function of Tau concentration of the analog counterpart of the sensor shown in FIG. 35, where the sensor does not detect concentration changes below 1 ng/mL.

The hue values of the nanostructures in the analog section were compared between the pre-image and post-image. The histogram of delta Hue is presented in FIG. 37. When the concentration of analyte is low (for example, less than 1 ng/mL), the delta Hue was close to zero. In these concentration ranges, positive flip from FIG. 36 was used as the indicator for analyte concentration. As the concentration increased above 1 ng/mL in FIG. 36, delta Hue started to increase, as shown in FIG. 38. Therefore, by combining both the digital and analog analysis, Tau protein concentration could be measured in a large dynamic range from 1 pg/mL to 1 µg/mL (about 6 orders of magnitude). In this assay, Tau protein was detected down to 1 pg/mL.

Example 2—Creation and Testing of An Exemplary Sensor For Binding IL-6

This example describes the creation and testing of nanostructures that bind IL-6.

A sensor was created as essentially as described in Example 1. However, the nanostructures were functionalized with IL-6 antibodies rather than Tau antibodies. A second IL-6 antibody (targeting a different epitope than the first antibody) labeled with HRP was used to form the sandwich. The reactions were performed essentially as described in Example 1 and the results are shown in FIG. 39.

Figure 39:
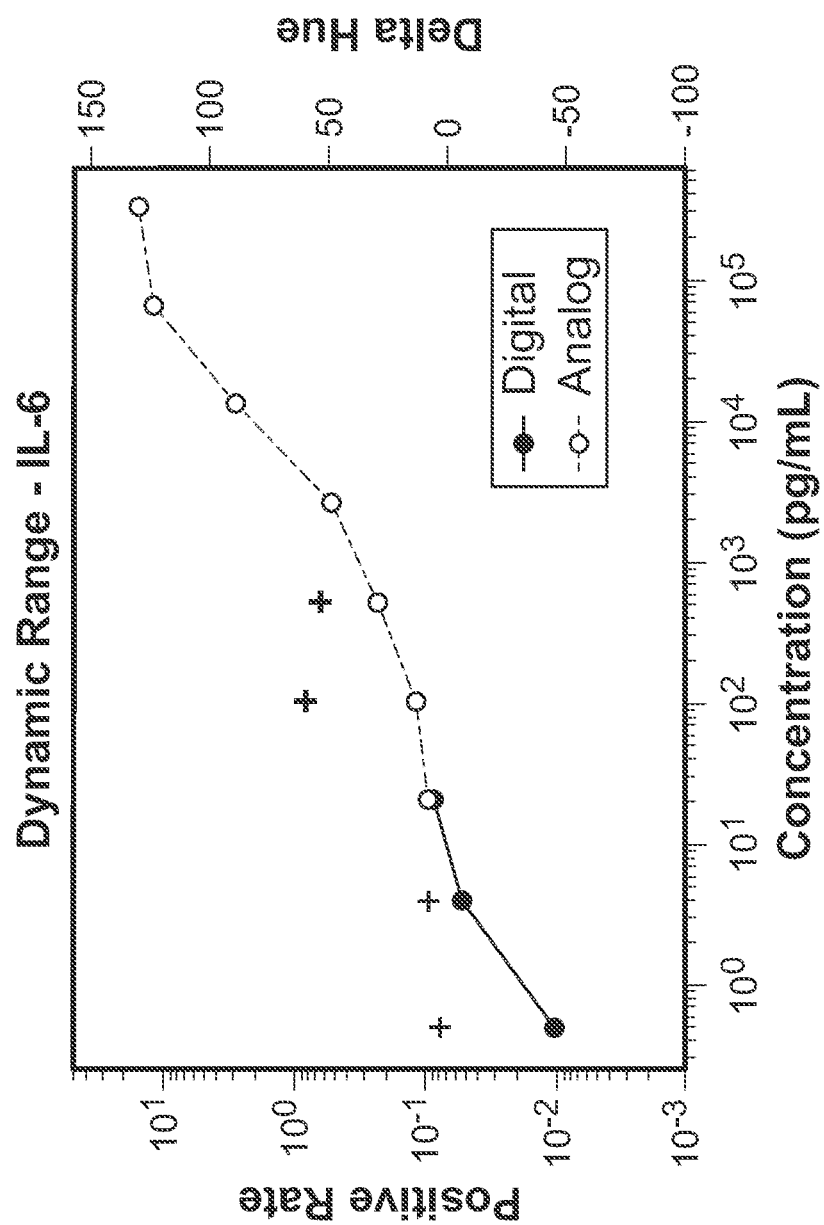
FIG. 39 is graph showing the detection and quantification of IL-6 using an exemplary sensor of the invention.

As shown in FIG. 39, a combination of digital and analog detection methods allows the quantification of IL-6 proteins in a range from 7 pg/mL to 1 µg/mL.

For a recovery analysis, IL-6 concentrations of 7 pg/mL, 25 pg/mL, 50 pg/mL, 75 pg/mL and 125 pg/mL were prepared and spiked into the buffer solution. The standard curve shown in FIG. 39 was used to quantify the molecules of IL-6 detected. The spike recovery rate was found to be at least 95%.

Example 3—Use of Exemplary Sensors to Detect IL-6, TNF and C Reactive Protein (CRP) in Different Media This example demonstrates that exemplary nanostructures can be used to detect IL-6 and TNF in plasma, and CRP in cell culture media.

Figure 40A:
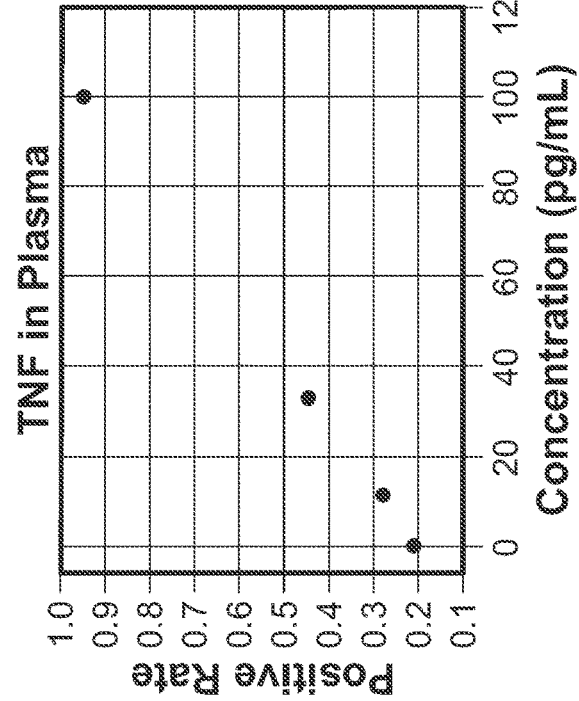
FIGS. 40A, 40B, and 40C are graphs showing the detection of IL-6 in plasma (FIG. 40A), TNF in plasma (FIG. 40B), and C reactive protein in cell culture medium (FIG. 40C) using exemplary sensors of the invention.
Figure 40B:
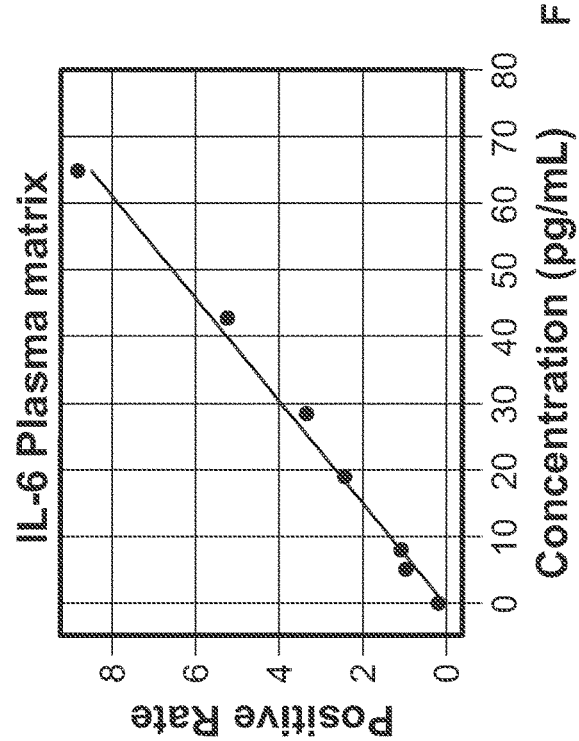
Figure 40C:
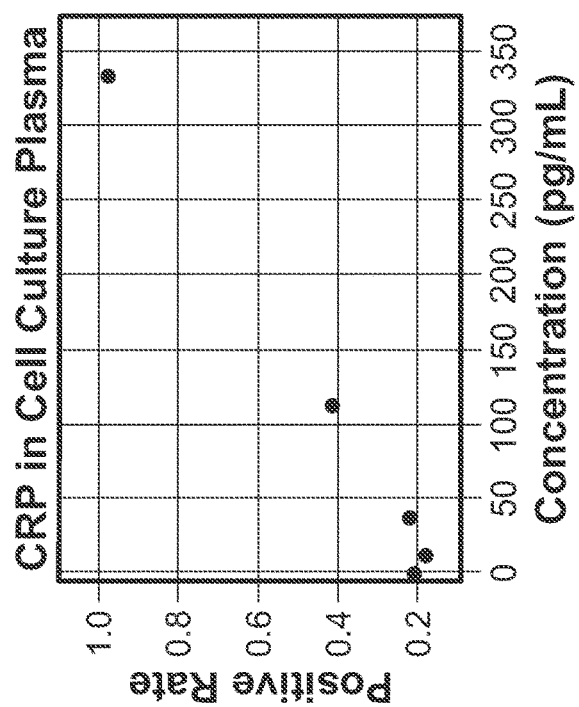

The sensors with functionalized nanostructures were created and tested essentially as described in Examples 1 and 2, except the capture and detection antibodies were selected for the given target analyte. The results are set forth in FIGS. 40A, 40B and 40C, which show that the nanostructures are capable of detecting IL-6 (in plasma), TNF (in plasma) and CRP (in cell culture media) with good linearity of each standard curve as a function of analyte concentration.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A sensor for detecting presence, or quantifying an amount, of an analyte in a sample of interest, the sensor comprising:
a first region and a second region,
the first region comprising a first series of nanostructures capable of binding the analyte and producing a detectable signal indicative of a concentration of the analyte in the sample within a first concentration range, and
the second region comprising a second series of different nanostructures capable of binding the analyte and producing a detectable signal indicative of a concentration of the analyte in the sample within a second, different concentration range,
wherein (i) the sensor is capable of quantifying the amount of analyte in a sample across both the first concentration range and the second concentration range and (ii) the nanostructures are integral with at least one of a planar support or a flexible substrate.

2. The sensor of claim 1, wherein individual nanostructures of the first series that bind the analyte are optically detected upon binding the analyte, whereupon the concentration of analyte in the sample, if within the first concentration range, is determined from a number of individual nanostructures in the first series that have bound molecules of analyte, and wherein the concentration of analyte in the sample, if within the second concentration range, is determined by analog detection of a substantially uniform change in an optically detectable property of the nanostructures in the second region as a function of the concentration of the analyte.

3. The sensor of claim 1, wherein the first concentration range has a lower detectable value than that of the second concentration range.

4. The sensor of claim 1, wherein the first region comprises one or more of:
(i) center-to-center spacing of adjacent nanostructures of at least 1 µm;
(ii) a minimum cross-sectional dimension or diameter of each nanostructure of at least 10 nm;
(iii) a maximum cross-sectional dimension or diameter of each nanostructure of no more than 200 nm; or
(iv) a height of each nanostructure in a range of 50 nm to 1000 nm; and
optionally, wherein the sensor further comprises a second region comprising one or more of:
(v) a fiducial marker; or
(vi) a nanostructure fabrication control feature.

5. The sensor of claim 1, further comprising a third region comprising a third series of further different nanostructures capable of binding the analyte and producing a detectable signal indicative of the concentration of the analyte in the sample within a third concentration range, wherein the sensor is capable of quantifying the amount of the analyte in the sample across the first, second and/or third concentration ranges.

6. The sensor of claim 5, wherein the third nanostructures are functionalized with a binding agent that binds the analyte.

7. The sensor of claim 1, wherein the nanostructures in any second series comprise one of more of (i) an average height, (ii) an average volume, (iii) an average surface area, (iv) an average mass, and (v) an average number of analyte binding sites, that is greater than that of the nanostructures in the first series.

8. The sensor of claim 1, wherein the first and second nanostructures are functionalized with a binding agent that binds the analyte.

9. The sensor of claim 1, wherein the analyte is a biological molecule.

10. The sensor of claim 1, wherein the sensor is capable of detecting the concentration of analyte in the sample across a range spanning at least 5, 6, 7, 8 or 9 orders of magnitude.

11. The sensor of claim 1, wherein the sample is a body fluid, tissue extract, and/or cell supernatant.

12. The sensor of claim 1, wherein the binding of analyte is detected by a change in an optically detectable property of at least one series of nanostructures.

13. The sensor of claim 1, wherein, in the first series of nanostructures, individual nanostructures that bind the analyte are detected upon binding either a single molecule of analyte or less than a predetermined number of molecules of the analyte, whereupon the concentration of analyte in the sample, if present in the first concentration range, is determined from a number of individual nanostructures in the first series that have bound molecules of the analyte.

14. The sensor of claim 1, wherein the concentration of analyte, if within the second concentration, is determined by analog detection of a substantially uniform change in an optically detectable property of the nanostructures in the second region as a function of the concentration of the analyte.

15. The sensor of claim 1, wherein the sensor comprises a plurality of different binding agents for detecting a corresponding plurality of different analytes in the test sample.

16. The sensor of claim 1, wherein the concentration of analyte in a sample across both the first concentration range and the second concentration range is determined from a number of individual nanostructures in each of the first series and/or the second series that have bound molecules of the analyte.

17. The sensor of claim 1, wherein the concentration of analyte in a sample across both the first concentration range and the second concentration range is determined by analog detection of a substantially uniform change in an optically detectable property of the nanostructures in each of the first region and/or the second region.

18. A cartridge for detecting a presence, or quantifying an amount, of an analyte in a sample of interest, the cartridge comprising a housing defining at least one well comprising a sensor of claim 1.

19. A system for detecting presence, or quantifying an amount, of an analyte in a sample of interest, the system comprising:
  (a) a receiving chamber for receiving a sensor of claim 1 or a cartridge for detecting a presence, or quantifying an amount, of an analyte in a sample of interest, the cartridge comprising a housing defining at least one well comprising a sensor of claim 1;
  (b) a light source for illuminating at least the first series and/or any second series and/or any third series of nanostructures;
  (c) a detector for detecting a change in an optical property in at least the first series and/or any second series and/or any third series of nanostructures; and
  (d) an optional computer processor implementing a computer algorithm that identifies an interface between the first concentration range and optionally any second concentration range and optionally an interface between any second concentration range and optionally any third concentration range.

20. The system of claim 19, wherein the algorithm comprises the steps of (a) measuring the number of nanostructures that have changed from one state to another relative to the number of nanostructures in the first series upon application of the solution to be tested; (b) measuring color space changes of nanostructures in the second series of nanostructures upon application of the solution to be tested; and (c) if the color space change of the second series is greater than a preselected threshold value, then use the analog measurements collected in step (b) and if the color space changes of the second series is less than the preselected threshold value, then use the digital measurements collected in step (a).

21. A method of detecting presence, or quantifying an amount, of an analyte in a sample of interest, the method comprising:
  (a) applying a portion of the sample to the sensor of claim 1; and
  (b) detecting a change in a property of the first series and/or any second series and/or any third series of nanostructures thereby to detect the presence, or quantify the amount, of the analyte in the sample.

22. The method of claim 21, wherein, in step (b), the property is an optical property.

23. The method of claim 21, wherein the method is capable of detecting analyte in a concentration range of at least 5, 6, 7, 8, or 9 logs.

24. The method of claim 21, wherein the sensor is capable of detecting analyte in a concentration range from less than 1 fg/mL to greater than 1 mg/mL.

25. The method of claim 21, wherein the sample is a body fluid, a tissue extract, or a cell supernatant.

26. A sensor for detecting presence, or quantifying an amount, of an analyte in a sample of interest, the sensor comprising:
  a first region comprising a first series of nanostructures capable of binding the analyte and producing a detectable signal indicative of a concentration of the analyte in the sample within a first concentration range, wherein (i) individual nanostructures of the first series that bind the analyte are optically detected upon binding the analyte, whereupon the concentration of analyte in the sample, if within the first concentration range, is determined from a number of individual nanostructures in the first series that have bound molecules of analyte and (ii) the nanostructures are integral with at least one of a planar support or a flexible substrate.

27. The sensor of claim 26, wherein the concentration of analyte in the sample is determined by digital counting of the number of individual nanostructures in the first series that have bound the analyte relative to either (i) a remaining number of individual nanostructures that have not bound analyte or (ii) a total number of nanostructures in the first series.

28. A sensor for detecting presence, or quantifying an amount, of an analyte in a sample of interest, the sensor comprising:
  a first region comprising a first series of nanostructures capable of binding the analyte and producing a detectable signal indicative of a concentration of the analyte in the sample within a first concentration range, wherein the concentration of analyte in the sample, if within the first concentration range, is determined by analog detection of a substantially uniform change in an optically detectable property of the nanostructures in the first region as a function of the concentration of the analyte, wherein (a) the nanostructures are integral with at least one of a planar support or a flexible substrate and (b) the first region comprises one or more of:
  (i) center-to-center spacing of adjacent nanostructures of at least 1 µm;
  (ii) a minimum cross-sectional dimension or diameter of each nanostructure of at least 100 nm;
  (iii) a maximum cross-sectional dimension or diameter of each nanostructure of no more than 300 nm; or
  (iv) a height of each nanostructure in a range of 50 nm to 1000 nm; and
  optionally, wherein the sensor further comprises a second region comprising one or more of:
  (v) a fiducial marker; or
  (vi) a nanostructure fabrication control feature.

29. A method of detecting presence, or quantifying an amount, of an analyte in a sample of interest, the method comprising:
  (a) applying a portion of the sample to a sensor comprising a first region and a second region, (i) the first region comprising a first series of nanostructures capable of binding the analyte and producing a detectable signal indicative of a concentration of the analyte in the sample within a first concentration range, and
(ii) the second region comprising a second series of different nanostructures capable of binding the analyte and producing a detectable signal indicative of a concentration of the analyte in the sample within a second, different concentration range;

(b) detecting the detectable signals from the first and second series of nanostructures; and (c) determining from the detectable signals the concentration of analyte in the sample across both the first concentration range and the second concentration range, wherein the nanostructures are integral with at least one of a planar support or a flexible substrate.

30. The method of claim 29, (i) wherein individual nanostructures of the first series that bind the analyte are optically detected upon binding the analyte, whereupon the concentration of analyte in the sample, if within the first concentration range, is determined from a number of individual nanostructures in the first series that have bound molecules of analyte, and (ii) wherein the concentration of analyte in the sample, if within the second concentration range, is determined by analog detection of a substantially uniform change in an optically detectable property of the nanostructures in the second region as a function of the concentration of the analyte.

* * * * *